United States Patent [19]
Iqbal et al.

[11] Patent Number: 5,990,083
[45] Date of Patent: Nov. 23, 1999

[54] MULTICATALYTIC PROTEASE INHIBITORS

[75] Inventors: Mohamed Iqbal, Malvern; James L. Diebold, Norristown, both of Pa.; Robert Siman, Wilmington, Del.; Sankar Chatterjee, Wynnewood; James C. Kauer, Kennett Square, both of Pa.

[73] Assignee: Cephalon, Inc., West Chester, Pa.

[21] Appl. No.: 08/816,510

[22] Filed: Mar. 13, 1997

Related U.S. Application Data

[62] Division of application No. 08/760,638, Dec. 4, 1996, Pat. No. 5,830,870, which is a division of application No. 08/552,794, Nov. 3, 1995, Pat. No. 5,614,649, which is a continuation-in-part of application No. 08/464,398, Jun. 5, 1995, abandoned, which is a continuation-in-part of application No. 08/337,795, Nov. 14, 1994, Pat. No. 5,550,262.

[51] Int. Cl.$^6$ .................... A61K 38/00; C07C 231/00; C07C 235/00; C07C 255/00
[52] U.S. Cl. ................... 514/9; 564/123; 554/36; 554/42; 554/51; 554/52; 554/54; 554/57; 558/432
[58] Field of Search ............... 514/19; 564/123; 554/36, 51, 54, 42, 57; 558/432

[56] References Cited

U.S. PATENT DOCUMENTS

| | | | |
|---|---|---|---|
| 4,499,082 | 2/1985 | Shenvi et al. | 514/2 |
| 4,518,528 | 5/1985 | Rasnick | 260/112.5 R |
| 4,636,492 | 1/1987 | Kettner et al. | 514/18 |
| 4,652,552 | 3/1987 | Kettner et al. | 514/18 |
| 5,024,994 | 6/1991 | Doherty et al. | 514/18 |
| 5,296,468 | 3/1994 | Hoeger et al. | 514/15 |
| 5,340,736 | 8/1994 | Goldberg | 435/226 |
| 5,550,262 | 8/1996 | Iqbal et al. | |
| 5,614,649 | 3/1997 | Iqbal et al. | |
| 5,830,870 | 11/1998 | Iqbal et al. | |

FOREIGN PATENT DOCUMENTS

| | | |
|---|---|---|
| 0275480 | 7/1988 | European Pat. Off. |
| 4-202170 | 7/1992 | Japan |
| WO 91/06543 | 5/1991 | WIPO |
| WO 91/13904 | 9/1991 | WIPO |
| WO 92/20804 | 11/1992 | WIPO |

OTHER PUBLICATIONS

Allen et al., "Differential Requirements for Antigen Processing by Macrophages for Lysozyme–specific T Cell Hybridomas", *J. Immunol.* 1984, 132, 1077–1079.

Amsterdam, A. et al., "Changes in intracellular localization of proteasomes in immortalized ovarian granulosa cells during mitosis associated with a role in cell cycle control", PNAS USA, 90:99–103 (1993).

Armon, T. et al., "Assembly of the 26 S complex that degrades proteins ligated to ubiquitin is accompanied by the formation of ATPase activity", J. of Biol. Chem., 265(34):20723–20726 (1990).

Arribas, J. et al., "Autoantibodies against the multicatalytic proteinase in patients with systemic lupus erythematosus", J. Exp. Med., 173:423–427 (1991).

Arrigo, A.–P., et al., "Identity of the 19S 'prosome' particle with the large multifunctional protease complex of mammalian cells (the proteasome)", Nature 331:192–194 (1988).

Azaryan, A. et al., "The presence of ATp+ubiquitin–dependent proteinase and multicatalytic proteinase complex in bovine brain", Neurochemical Res., 14(10):995–1001 (1989).

Baldwin, J. et al., "$^{11}$B NMR studies of an aryl boronic acid bound to chymotripsin and subtilisin", Bioorganic & Medicianl Chem. Letters, 1(1):9–12 (1991).

Bannister, J. et al., "Aspects of the structure, function, and applications of superoxide dismutase", CRC Critical Reviews in Biochemistry 22(2):111–179 (1987).

Bartel, B. et al., "The recognition component of the N–end rule pathway", The EMBO Journal 9(10):3179–3189 (1990).

Basak, A. et al., "Syntheses of argininal semicarbazone containing peptides and their applications in the affinity chromatography of serine proteinases", Int. J. Peptide Protein Res. 36:7–17 (1990).

Bewley, "cDNA and deduced amino acid sequence of murine Cu—Zn superoxide dismutase", Nucleic Acids Research 16(6):2728 (1988).

Borchelt, D. et al., "Superoxide dismutase 1 with mutations linked to familial amyotrophic lateral sclerosis possesses significant activity", PNAS USA, 91:8292–8296 (1994).

Bowling, A. et al., "Superoxide dismutase activity, oxidative damage, and mitochondrial energy metabolism in familial and sporadic amyotrophic lateral sclerosis", J. of Neurochemistry 61:2322–2325 (1993).

Brown, M. et al., "Structural and serological similarity of MHC–linked LMP and proteasome (multicatalytic proteinase) complexes", Nature 353:355–357 (1991).

Brown, R.H. "Clinical Implications of Basic Research. A Transgenic–Mouse Model of Amyotrophic Lateral Sclerosis", NEJM 1994, 331(16), 1091–1092.

(List continued on next page.)

*Primary Examiner*—Nita Minnifield
*Attorney, Agent, or Firm*—Woodcock Washburn Kurtz Mackiewicz & Norris LLP

[57] ABSTRACT

Disclosed herein are inhibitors of the multicatalytic protease enzyme which are represented by the general formula:

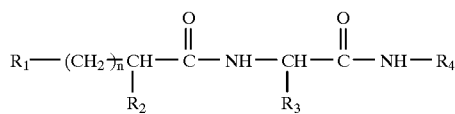

Constituent members and preferred constituent members are disclosed herein. Methodologies for making and using the disclosed compounds are also set forth herein.

11 Claims, 7 Drawing Sheets

OTHER PUBLICATIONS

Cardozo, C. et al., "Evidence that the nature of amino acid residues in the $P_3$ position directs substrates to distinct catalytic sites of the pituitary multicatalytic proteinase complex (proteasome)", Biochemistry 33:6483–6489 (1994).

Carrell and Boswell, Proteinase inhibitors, Barrett and Salvesen (eds.), Chap. 12, Elsevier Science Publishers BV (Biomedical Division) pp. 403–420 (1986).

Chau, V. et al., "A multiubiquitin chain is confined to specific lysine in a targeted short–lived protein", Science, 243:1576–1583 (1989).

Chen and Okayama, "Calcium phosphate–mediated gene transfer: a highly efficient transfection system for stably transforming cells with plasmid DNA", *Biotechniques* 1988, 6(7), 632–638.

Chu–Ping, M. et al., "Identification, purification, and characterization of a protein activator (PA28) of the 20 S proteasome (macropain)", The J. of Biol. Chem. 267(15):1015–10523, (1992).

Chu–Ping, M. et al., "Purification and characterization of a protein inhibitor of the 20S proteasome (macropain)", Biochimica et Biophysica Acta, 1119:303–311 (1992).

Ciechanover, A. et al., "Degradation of nuclear oncoproteins by the ubiquitin system in vitro", PNAC USA 88:139–143 (1991).

Ciechanover and Schwartz, "The ubiquitin–mediasted proteolytic pathway: mechanisms of recognition of the proteolytic substrate and involvement in the degradation of native cellular proteins", The FASEB Journal 8:182–191 (1994).

Collins, D. et al., "Processing of exogenous liposome–encapsulated antigens in vivo generates class I MHC–restricted T cell responses", The J. of Immunol. 148(11):3336–3341 (1992).

DeMartino, G. et al., "The primary structures of four subunits of the human, high–molecular–weight proteinase, macropain (proteasome), are distinct but homologous", Biochimica et Biophysica Acta 1079:29–38 (1991).

DeMartino, G. et al., "ATP–stimulated degradation of endogenous proteins in cell–free extracts of BHK 21/C13 fibroblasts A key role for the proteinase, macropain, in the ubiquitin–dependent degradation of short–lived proteins", Biochimica et Biophysica Acta 1073:299–308 (1991).

Deng, H.–X. et al., "Amyotrophic lateral sclerosis and structural defects in Cu, Zn Superoxide Dismutase", Science 261:1047–1051 (1993).

Dick, L. et al., "Degradation of Oxidized Insulin B Chain by the Multiproteinase Complex Macropain (Proteasome)", *Biochemistry* 1991, 30, 2725–2734.

Drechsel, D. et al., "Affinity chromatography of α–1–protease inhibitor using sepharose–4B–bound anhydrochymotrypsin", Anayltical Biochemistry 143:141–145 (1984).

Driscoll and Goldberg, "Skeletal muscle proteasome cna degrade proteins in an ATP–dependent process that does not require ubiquitin", PNAC USA 86:787–791 (1989).

Dubiel, W. et al., "Purification of 11 S regulator of the multicatalytic protease", The J. of Biol. Chemistry, 267(31):22369–22377 (1992).

Driscoll, J. et al., "An ATP–stabilized inhibitor of the proteasome is a component of the 1500–kDa ubiquitin conjugate–degrading complex", PNAS USA 89:4986–4990 (1992).

Driscoll, J. et al., "MHC–linked IMP gene products specifically alter peptidase activities of the proteasome", Nature 365:262–264 (1993).

Dubiel, W. et al., "Subunit 4 of the 26 S protease is a member of a novel eukaryotic ATPase family", The J. of Biological Chemistry 267(32):22699–22702 (1992).

Eytan, E. et al., "ATP–dependent incorporation of 20S protease into the 26S complex that degrades proteins conjugated to ubiquitin", PNAS USA 86:7751–7755 (1989).

Fagan and Waxman, "A novel ATP–requiring protease from skeletal muscle that hydrolyzes non–ubiquitinated proteins", The J. of Biological Chemistry 274(30) 17868–17872 (1989).

Fagan, J. et al., "Red blood cells contain a pathway for the degradation of oxidant–damaged hemoglobin that does not require ATP or ubiquitin", The J. of Biological Chemistry 261(13):5705–5713 (1986).

Falkenburg et al., "Drosophila small cytoplasmic 19S ribonucleoprotein is homologous to the rat multicatalytic proteinase", Nature 331:190–192 (1988).

Fruh, Klaus et al., "Alternative exon usage and processing of the major histocompatibility comoplex–encoded proteasome subunits", The J. of Biiological Chem., 267(31):22131–22140 (1992).

Fujiwara, T. et al., "Proteasomes are essential for yeast proliferation. cDNA cloning and gene disruption of two major subunits", 265(27):16604–16613 (1990).

Fujiwara, T. et al., "Molecular cloning of cDNA for proteasomes multicatalytic proteinase complexes from rat liver: primary structure of the largest component (C2)", Biochemistry 28:7332–7340 (1988).

Furuno, K. et al., "Role of different proteolytic systems in the degradation of muscle proteins during denervation atrophy", The J. of Biological Chemistry 265(15):8550–8557 (1990).

Gaczynska, M. et al., "γ–Interferon and expression of MHC genes regulate peptide hydrolysis by proteasomes", Nature 365:264–267 (1993).

Galloway and Likavec, "Ubiquitin in normal, reactive and neoplastic human astrocytes", Brain Research 500:343–351 (1989).

Ganoth, D. et al., "A multicomponent system that degrades proteins conjugated to the ubiquitin", The J. of Biological Chemistry, 263(25):12412–12419 (1988).

Garlick, P.J. et al., "A Rapid and Convenient Technique for Measuring the rate of Protein Synthesis in Tissues by Injection of ($^3$H)phenylalanine", *Biochem. J.* 1980, 192, 719–723.

Glynne, R. et al., "A proteasome–related gene between the two ABC transporter loci in the class II region of the human MHC", Nature 353:357–360 (1991).

Goldberg & St. John, "Intracellular Protein degradation in Mammalian and Bacterial Cells: Part 2" *Annu. Rev. Biochem.* 1976, 45, 747–803.

Goldberg, "The mechanism and functions of ATP–dependent proteases in bacterial and animal cells", Eur. J. Biochem. 203:9–23 (1992).

Goldberg and Rock, "Proteolysis, proteasomes and antigen presentation", Nature 357:375–379 (1992).

Greene & Wuts, "Protecting groups in organic synthesis", 2d Ed., Wiley & Sons, 1991.

Greenwald, "Superoxide dismutase and catalase as therapeutic agents for human diseases. A critical review", Free Radical Biology & Medicine 8:201–209 (1990).

Haas, et al., "The inactivation of ubiquitin accounts for the inability to demonstrate ATP, ubiquitin–dependent proteolysis in liver extracts", The J. of Biological chemistry 260(8):4694–4703 (1985).

Haass, C. et al., "The PROS–35 gene encodes the 35 kd protein subunit of Drosophila melanogaster proteasome", The EMBO Journal 8(8):2373–2379 (1989).

Halliwell and Gutteridge, "Role of free radicals and catalytic metal ions in human disease: an overview", Methods in Enzymology 186:1–75 (1990).

Harding III et al., "Electroporation of exogenous antigen into the cytosol for antigen processing and class I major histocompatibility complex (MHC) presentation: weak base amines and hypothermia (18° C.) inhibit the class I MHC processing pathway", Eur. J. Immunol. 22:1865–1869 (1992).

Harding, C. et al., "Liposome–encapsulated antigens engender lysososmal processing for Class II MHC presentation and cytosolic processing for Class I presentation", The J. of Immunol. 147(9):2860–2863 (1991).

Hegde, A. et al., "Regulatory subunits of cAMP–dependent protein kinases are degraded after conjugation to ubiquitin: A molecular mechanism underlying long–term synaptic plasticity", PNAC USA 90:7436–7440 (1993).

Heinemeyer, W. et al., "Proteinase yscE, the yeast proteasome/multicatalytic–multifunctional proteinase: mutants unravel its function in stress induced proteolysis and uncover its necessity for cell survival", The EMBO Journal 10(3):555–562 (1991).

Hershko, A. et al, "Components of ubiquitin–protein ligase system", The J. of Biological Chemistry 258(13):8206–8214 (1983).

Hershko & Crechanovh, "Mechanisms of Intracellular Protein Breakdown", Annu. Rev. Biochem. 1982, 51, 335–364.

Hershko and Heller, "Occurrence of a polyubiquitin structure in ubiquitin–protein conjugates", Biochemical and Biophysical Research Comm. 128(3):1079–1086 (1985).

Hershko and Rose, "Ubiquitin–aldehyde: A general inhibitor of ubiquitin–recycling processes", PNAC USA 84:1829–1833 (1987).

Hershko, A. et al., "ATP–dependent degradation of ubiquitin–protein conjugates", PNAC USA 81:1619–1623 (1984).

Ho, S. et al., "Site–directed mutagenesis by overlap extension using the polymerase chain reaction", Gene 77:51–59 (1989).

Hoffman, L. et al., "Multiple forms of the 20 S multicatalytic and the 26 S ubiquitin/ATP–dependent proteases from rabbit reticulocyte lysate", The J. of.

Holloway, S. et al., "Anaphase is initiated by proteolysis rather than by the inactivation of maturation–promoting factor", Cell 73:1393–1402 (1993).

Hough and Rechsteiner, "Effects of temperature on the degradation of proteins in rabbit reticulocyte lysates and after injection into HeLa cells", PNAC USA 81:90–94.

Hough, R. et al., "Purification of two high molecular weight proteases from rabbit reticulocyte lysate", The J. of Biol. Chem. 262(17):8303–8313 (1987).

Hough and Rechstiner, "Ubiquitin–lysozyme conjugates. Purification and susceptibility to proteolysis", The J. of Biol. Chem. 261(5):2391–2399 (1986).

Hudig, D. et al., "Selective isocoumarin serine protease inhibitors block RNK–16 lymphocyte granule–mediated cytolysis", Molecular Immunology 26(8):793–798 (1989).

Ishiura, S. et al., "Isolation of two forms of the high–molecular–mass serine protease, ingensin, from porcine skeletal muscle", FEBS Letters 189(1):119–123 (1985).

Ishiura, S. et al., "Addition of ATP increases the apparent molecular mass of the multicatalytic proteinase, ingensin", FEBS Letters 257(1):123–126 (1989).

Ishiura, S. et al., "Putative N–terminal splitting enzyme of amyloid A4 peptides is the multicatalytic proteinase, ingensin, which is widely distributed in mammalian cells", FEBS Letters 257(2):388–392 (1989).

Ishiura, S. et al., "Distribution of Alzheimer's disease amyloid A4–generating enzymes in rat brain tissue", Neuroscience Letters 115:329–334 (1990).

Jaspers and Tischler, "Atrophy and Growth Failure of rat Hindlimg Muscles in Tail–Cast Suspension", J. App. Phys. 1984, 57(5), 1472–1479.

Johnson, E. et al., "Ubiquitin as a degradation signal", The EMBO Journal 11(2):497–505 (1992).

Kamakura, K. et al., "Localization of ingensin in rat central nervous system and skeletal muscle", Journal of Neuroscience Research 20:473–478 (1988).

Kettner and Shenvi, "Inhibition of the serine proteases leukocyte elastase, pancreatic elastase, cathespin G, and chymotrypsin by peptide boronic acids", The J. of Biological Chemistry 259(24):15106–15114 (1984).

Kidd and Woo, Chapter 13, "Molecular analysis of the serine proteinase inhibitor gene family", Proteinase Inhibitors, Barrett and Salvesen (eds.), Elsevier.

Kloetzel, P.–M. et al., "The 19S Ring–type Particles of Drosophila", Experimental Cell Research 170:204–213 (1987).

Kojima and Omori, "Two–way cleavage of β–amyloid protein precursors by multicatalytic proteinase", FEBS Letters 304 (1):57–60 (1992).

Kopp, F. et al., "Size and shape of the multicatalytic proteinase from rat skeletal muscle", Biochimica et Biophysica Acta 872:253–260 (1986).

Kumatori, A. et al., "Abnormally high expression of proteasomes in human leukemic cells", PNAC USA 87:7071–7075 (1990).

Kwak, S. et al., "Multicatalytic proteinase is present in Lewy bodies and neurofibrillary tangles in diffuse Lewy body disease brains", Neuroscience Letters 128:21–24 (1991).

Laskowski and Kato, "Protein inhibitors of proteinaseses", Ann. Rev. Biochem. 49:593–626 (1980).

Lee, L. et al., "Relationships among the subunits of the high molecular weight proteinase, macropain (proteasome)", Biochimica et Biophysica Acta 1037:178–185 (1990).

Lowe, J. et al., "Ubiquitin Carboxyl–Terminal Hydrolase (PGP 9.5) is selectively present in ubiquitinated inclusion bodies characterisitic of human neurodegenerative diseases", J. of Pathology 161:153–160 (1990).

Lucas, J. et al., "Susceptibility of Myelin Proteins to a Neutral Endproteinase: the Degradation of Myelin Basic Protein (MBP) and $P_2$ Protein by Purified Bovine Brain Multicatalytic Proteinase Complex (MPC)", Neurochem. Research 17(12):1261–1266 (1992).

Mason, R., "Characterization of the active site of human multicatalytic proteinase", Biochem. J. 265:479–484 (1990).

Matthews, W. et al., "Involvement of the proteasome in various degradative processes in mammalian cells", PNAC USA 86:2597–2601 (1989).

McConnell, R. et al, "Inhibition studies of some serine and thiol proteinases by new leupeptin analogues", J. Med. Chem. 36(8):1084–1089 (1993).

McDermott and Gibson, "The activity of the High–$M_r$, multicatalytic protease in normal brain and brain from Alzheimer's disease patients", Neuroscience Res. Comm. 8(3):185–190 (1991).

McDermott, J.R. et al., "Multicatalytic, High–$M^4$ endopeptidase from postmortem human brain", J. of Neurochemistry 56(5):1509–1517 (1991).

McGuire, M. et al., "ATP–stimulated proteolysis in soluble extracts of BHK 21/C13 cells. Evidence for multiple pathways and a role for an enzyme related to the high–molecular–weight protease, macropain", Arch. of Biochem. and Biophysics 262(1):273–283 (1988).

McGuire, M. et al., "An enzyme related to the high molecular weight multicatalytic proteinase, macropain, participates in a ubiquitin–mediated, ATP–stimulated proteolytic pathway in soluble extracts of BHK 21/C13 fibroblasts", Biochimica et Biophysica Acta 967:195–203 (1988).

McGuire and DeMartino, "Purification and characterization of a high molecular weight proteinase (macropain) from human erythrocytes", Biochimica et Biophysica Acta 873:279–289 (1986).

Michalek, M. et al., "A role for the ubiquitin–dependent proteolytic pathway in MHC class I–restricted antigen presentation", Nature 363:552–554 (1993).

Monaco and McDevitt, "The LMP antigens: a stable MHC––controlled multisubunit protein complex", Human Immunology 15:416–426 (1986).

Monaco and McDevitt, "H–2 linked low–molecular weight polypeptide antigens assemble into an unusual macromolecular complex", Nature 309:797–799 (1984).

Munoz, K.M. et al., "Time Course of the Response of Myofibrillar and Sarcoplasmic Protein Metabolism to Unweighting of the Soleus Muscle", Metabolism 42(8):1006–1012 (1993).

Oleksyszyn and Powers, "Irreversible inhibition of serine proteases by peptide derivatives of ($\alpha$–aminoalkyl)phosphonate diphenyl esters", Biochemistry 30:485–493 (1991).

Orlowski, M., "The multicatalytic proteinase complex, a major estralysosomal proteolytic system", Biochemistry 29(45):10289–10297 (1990).

Orlowski and Michaud, "Pituitary multicatalytic proteinase complex. Specificity of components and aspects of proteolytic activity", Biochemistry 28:9270–278 (1989).

Orlowski, M. et al., "Evidence for the presence of five distinct proteolytic components in the pituitary multicatalytic proteinase complex. Properties of two components cleaving bonds on the carboxyl side of branched chain and small neutral amino acids", Biochemistry 32:1563–1572 (1993).

Pappolla, M.A. et al., "The "normal" brain. "Abnormal" ubiquitinilated deposits highlight an age–related protein change", Am. J. of Pathology, 135(4):585–591 (1989).

Pfeifer et al., "Phagocytic processing of bacterial antigens for class I MHC presentation to T cells", Nature 361:359–362 (1993).

Pickart, C. et al., "Murine erythroleukemia cells possess an active ubiquitin– and ATP–dependent proteolytic pathway", Archives of Biochem. and Biophysics, 272(1):114–121 (1989).

Powers and Harper, "Inhibitors of serine proteinases", Chapter 3, Proteinase Inhibitors, Barrett and Salvesen (eds.), Elsevier Science Publishers BV (Biomedical Division), 1986.

Ray and Harris, "Lens neutral endopeptidase occurs in other bovine and human tissues", Biochem. J. 248:643–648 (1987).

Rechsteiner, M. et al., "The multicatalytic and 26S proteases", The J. of Biol. Chem., 268(9):6065–6068 (1993).

Remington's Pharmaceutical Sciences (Mack Pub. Co., Easton, PA, (1980).

Rivett and Sweeney, "Properties of subunits of the multicatalytic proteinase complex revealed by the use of subunit–specific antibodies", Biochem. J. 278:171–177 (1991).

Rivett, A.J., "The Multicatalytic Proteinase. Multiple Proteolytic Activities", J. Biol. Chem. 1989, 264(21), 12215–12219.

Rivett, A.J., "Proteasomes: multicatalytic proteinase complexes", Biochem. J. 291:1–10 (1993).

Robertson, M. "Proteasomes in the pathway", Nature 353:300–301 (1991).

Rock, K. et al., "Inhibitors of the proteasome block the degradation of most cell proteins and the generation of peptides presented on MHC class I molecules", Cell 78:761–771 (1994).

Rosen, D. et al, "Mutations in Cu/Zn superoxide dismutase gene are associated with familial amyotrophic lateral sclerosis", Nature 362:59–62 (1993).

Saitoh, Y. et al., "Purification and characterization of multicatalytic proteinase form eggs of the ascidian *Halocynthia roretzi*", J. Biochem. 105:254–260 (1989).

Sato and Shiratsuchi, "'Chymotrypsin–like' activity of chicken liver multicatalytic proteinase resides in the smallest subunit", Chimica et Biophysica Acta 1041:269–272 (1990).

Schechter and Burger, "On the Size of the Active Site in Proteases. I. Papain", Biochem. Biophys. Res. Commun. 1967, 27(2), 157–162.

Silver and Haskell, "Acid–sensitive latent inhibitors for proteolytic enzymes: synthesis and characterization", J. Med. Chem. 32:1253–1259 (1989).

Sweeney and Rivett, "Immunological properties of the multicatalytic proteinase", Biochemical Society Transactions 17:1126–1127 631st Meeting, Guildford.

Tamura, T. et al., "Molecular cloning and sequence analysis of cDNAs for five major subunits of human proteasomes (multi–catalytic proteinase complexes)", Biochimica et Biophysica Acta, 1089:95–102 (1991).

Tamura, T. et al., "DNA cloning and sequencing of component C5 of proteasomes from rat hepatoma cells", FEBS Letters 264(1):91–94 (1990).

Tanaka, K. et al., "A high molecular weight protease in the cytosol of rat liver", The J. of Biol. Chem. 261(32):15197–15203 (1986).

Tanaka, K. et al., "Possible mechanism of nuclear translocation of proteasomes", FEBS Letters 271(1,2):41–46 (1990).

Tanaka, K. et al., "Proteasomes (multi–protease complexes) as 20 S ring–shaped particles in a variety of eukaryotic cells", The J. of Biol. Chem. 262(31):16209–16217 (1988).

Tanaka, K. et al., "Molecular cloning of cDNA for proteasomes from rat liver: primary structure of component C3 with a possible tyrosine phosphorylation site", Biochemistry 29:3777–3785 (1989).

Tanaka, K. et al., "Molecular organization of a high molecular weight multi–protease complex from rat liver", J. Mol. Biol. 203:985–996 (1988).

Tanaka, K. et al., "Role of substrate in reversible activation of proteasomes (multi–protease complexes) by sodium dodecyl sulfate", J. Biochem. 106:495–500 (1989).

Tischler, M.E., "Different Mechanisms of Increased Proteolysis in Atrophy Induced by Denervation or Unweighting of rat Soleus Muscle", Metabolism 39(7):756–763 (1990).

Tsubuki, S. et al., "Purification and characterization of a Z–Leu–Leu–Leu–MCA degrading protease expected to regulate neurite formation: a novel catalytic activity in proteasome", Biochem. and Biophys. Res. Comm. 196(3):1195–1201 (1993).

Tsukahara, T. et al., "An ATP–dependent protease and ingensin, the multicatalytic proteinase, in K562 cells", *Eur. J. Biochem.* 1988, 177(2), 261–266.

Vinitsky, A. et al., "Inhibition of the chymotrypsin–like activity of the pituitary multicatalytic proteinase complex", Biochemistry 31:9421–9428 (1992).

Wagner, B.J. et al., "Lens Neutral Proteinase Preparations Hydrolyze Glutamoyl Bonds", *Exp. Eye Res.* 1985, 40, 879–882.

Wagner, B.J. et al., "A synthetic endopeptidase substrate hydrolyzed by the bovine lens neutral proteinase preparation", Exp. Eye Res. 38:477–483 (1984).

Wagner, B.J. et al., "Differential inhibition of two proteolytic activities in bovine lens neutral–proteinase preparations", Biochem. J. 228:517–519 (1985).

Wagner and Margolis, "Common epitopes of bovine lens multicatalytic–proteinase–complex subunits", Biochem. J. 257:265–269 (1989).

Weitman and Etlinger, "A monoclonal antibody that distinguishes latent and active forms of the proteasome (multicatalytic proteinase complex)", The J. of Biol.

Wilk and Orlowski, "Evidence that pituitary cation–sensitive neutral endopeptidase is a multicatalytic protease complex", J. of Neurochem. 40(3):842–849.

Wilkinson, K., "Detection and inhibition of ubiquitin–dependent proteolysis", Methods in Enzymology 185:387–397 (1990).

Yamamoto, T. et al., "Purification of the two forms of the high–molecular–weight neutral proteinase ingensin from rat liver", Biochimica et Biophysica Acta 882:297–304 (1986).

Yang, Y. et al., "Proteasomes are regulated by interferon γ: Implications for antigen processing", PNAS USA 89:4928–4932 (1992).

Yewdell et al., "Cells Process Exogenous Proteins for Recognition by Cytotoxic T Lymphocytes", *Science* 1988, 239, 637–640.

Zhong, S. et al., "Observation of tightly bound $^{11}$B nuclear magnetic resonance signals on serine proteases. Direct solution evidence for tetrahedral geometry around the boron in the putative transition–state analogues", J. of the Am. Chem. Soc. 113(25):9429–9435 (1991).

Doherty, A. et al., "New Inhibitors of Human Renin That Contain Novel Replacements at the $P_2$ Site", *J. Med. Chem.* 1991, 34, 1258–1271.

Theobald, P. et al., "Novel Gonadotropin–Releasing Hormone Antagonists: Peptides Incorporating Modified $N^{\omega}$–Cyanoguanidino Moieties", *J. Med. Chem.* 1991, 34.

Theobald, P. et al., "General Method for Incorporation of Modified $N^{\omega}$–Cyanoguanidino Moieties on Selected Amino Functions During Solid–Phase Peptide Synthesis", *J. Am. Chem. Soc.* 1990, 112, 9624–9626.

Imperiali, B. an dAbeles, Inhibition of Serine Proteases by Peptidyl Fluormethyl Ketones, *Biochemistry* 1986, 25, 3760–3767.

Nakajima, K. et al., Mapping the Extended Substrate Binding Site of Cathespin G and Human Leukocyte Elastase, *J. Biochem.* 1979, 254, 4027–4032.

Morris et al, In: Robbins Pathologic Basis of Disease Eds: Cotran et al 4th Edition. WB Saunders Co. pp. 1429–1433, 1989.

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (xi) SEQUENCE DESCRIPTION: SEQ ID NO:1:

TCGATCGAAG CTTGCCGCCA CCATGGCGAT GAAAGC 36                                36

(2) INFORMATION FOR SEQ ID NO:2:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (xi) SEQUENCE DESCRIPTION: SEQ ID NO:2:

AGCTAGCCTC GAGCAGATTA CAGTTTAATG                                          30

(2) INFORMATION FOR SEQ ID NO:3:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (xi) SEQUENCE DESCRIPTION: SEQ ID NO:3:

TTAATCCTCA CTCTAAGAAA C                                                   21

(2) INFORMATION FOR SEQ ID NO:4:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (xi) SEQUENCE DESCRIPTION: SEQ ID NO:4:

TTGTACGGCC AGTGATGGAA TGCT                                                24

(2) INFORMATION FOR SEQ ID NO:5:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (xi) SEQUENCE DESCRIPTION: SEQ ID NO:5:

AGCATTCCAT CACTGGCCGT ACAA                                                24

(2) INFORMATION FOR SEQ ID NO:6:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (xi) SEQUENCE DESCRIPTION: SEQ ID NO:6:

```
TAATACGACT CACTATAGGG                                              20

(2) INFORMATION FOR SEQ ID NO:7:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:7:

GCACACCACT TTCATCGCCA TGGTGGCGGC AAGCTTCGAT C                      41

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

ATTAACCCTC ACTAAAGGGA                                              20

(2) INFORMATION FOR SEQ ID NO:9:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:9:

GATCGAAGCT TGCCGCCACC ATGGCGATGA AGTGGTGTG C                       41

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:10:

CTTCAGTTAA TCCTGTAA                                                18
```

MULTICATALYTIC PROTEASE INHIBITORS

This application is a division of U.S. application Ser. No. 08/760,638 filed Dec. 4, 1996, now U.S. Pat. No. 5,830,870, which is a division of U.S. application Ser. No. 08/552,794 filed Nov. 3, 1995, now U.S. Pat. No. 5,614,649, which is a continuation-in-part of U.S. application Ser. No. 08/464,398 filed Jun. 5, 1995, abandoned, which is a continuation-in-part of U.S. application Ser. No. 08/337,795 filed Nov. 14, 1994, now U.S. Pat. No. 5,550,262.

FIELD OF THE INVENTION

This invention relates to inhibitors of multicatalytic protease (MCP), to compositions including such inhibitors and to methods for the use of MCP inhibitors to, for example, retard loss of muscle mass incident to various physiological states.

BACKGROUND OF THE INVENTION

Eukaryotic cells constantly degrade and replace cellular protein. This permits the cell to selectively and rapidly remove proteins and peptides hasting abnormal conformations, to exert control over metabolic pathways by adjusting levels of regulatory peptides, and to provide amino acids for energy when necessary, as in starvation. See Goldberg, A. L. & St. John, A. C. *Annu. Rev. Biochem.* 45: 747–803 (1976). The cellular mechanisms of mammals allow for multiple pathways for protein breakdown. Some of these pathways appear to require energy input in the form of adenosine triphosphate ("ATP"). See Goldberg, A. L. & St. John, supra.

Multicatalytic protease (MCP, also typically referred to as "multicatalytic proteinase," "proteasome," "multicatalytic proteinase complex," "multicatalytic endopeptidase complex," "20S proteasome" and "ingensin") is a large molecular weight (700 kD) eukaryotic non-lysosomal proteinase complex which plays a role in at least two cellular pathways for the breakdown of protein to peptides and amino acids. See Orlowski, M. *Biochemistry* 29(45) 10289–10297 (1990). The complex has at least three different types of hydrolytic activities: (1) a trypsin-like activity wherein peptide bonds are cleaved at the carboxyl side of basic amino acids; (2) a chirmotrypsin-like activity wherein peptide bonds are cleaved at the carboxyl side of hydrophobic amino acids; and (3) an activity wherein peptide bonds are cleaved at the carboxyl side of glutamic acid. See Rivett, A. J. *J. Biol. Chem.* 264: 21 12215–12219 (1989) and Orlowski, supra.

One route of protein hydrolysis which involves MCP also involves the polypeptide "ubiquitin." Hershko, A. & Crechanovh, A. *Annu. Rev. Biochem.* 51: 335–364 (1982). This route, which requires MCP, ATP and ubiquitin, appears responsible for the degradation of highly abnormal proteins, certain short-lived normal proteins and the bulk of proteins in growing fibroblasts and maturing reticuloytes. See Driscoll, J. and Goldberg,, A. L. *Proc. Nat. Acad. Sci. U.S.A.* 86: 787–791 (1989). Proteins to be degraded by this pathway are covalently bound to ubiquitin via their lysine amino groups in an ATP-dependent manner. The ubiquitin-conjugated proteins are then degraded to small peptides by an ATP-dependent protease complex by the 26S proteasome, which contains MCP as its proteolytic core. Goldberg, A. L. & Rock, K. L. *Nature* 357: 375–379 (1992).

A second route of protein degradation which requires MCP and ATP, but which does not require ubiquitin, has also been described. See Driscoll, J. & Goldberg, A. L., supra. In this process, MCP hydrolyzes proteins in an ATP-dependent manner. See Goldberg, A. L. & Rock, K. L., supra. This process has been observed in skeletal muscle. See Driscoll & Goldberg, supra. However, it has been suggested that in muscle, MCP functions synergistically with another protease, multipain, thus resulting in an accelerated breakdown of muscle protein. See Goldberg & Rock, supra.

It has been reported that MCP functions by a proteolytic mechanism wherein the active site nucleophile is the hydroxyl group of the N-terminal threonine residue. Thus, MCP is the first known example of a threonine protease. See Seemuller et al., *Science* (1995) 268 579–582; Goldberg, A. L, *Science* (1995) 268 522–523.

The relative activities of cellular protein synthetic and degradative pathways determine whether protein is accumulated or lost. The abnormal loss of protein mass is associated with several disease states such as muscular dystrophy, cardiac cachexia, emphysema, leprosy, malnutrition, osteomalacia, child acute leukemia, and cancer cachexia. Loss of muscle mass is also observed in aging, long term hospitalization or long term confinement to bed, and in chronic lower back pain.

With denervation or disuse, skeletal muscles undergo rapid atrophy which leads to a profound decrease in size, protein content and contractile strength. This atrophy is an important component of many neuromuscular diseases in humans. Enhancement of protein breakdown has been implicated as the primary cause of muscle wasting in denervation atrophy. Furono, K. et al. *J. Biochem.* 265/15: 8550–8557 (1990). While the specific process or processes involved in protein hydrolysis in muscle has not been identified, evidence is available linking the involvement of MCP in the accelerated breakdown of muscle proteins. See, for example, Furono, supra., and PCT Published Application WO 92/20804 (publication date: Nov. 26, 1992).

MCP activity has been implicated in several disease states. For example, abnormally high expression of MCP in human leukemic cell lines has been reported. Kumatori, A. et al. PNAS 87: 7071 (1990). Autoantibodies against MCP in patients with systemic lupus erythematosus ("SLE") have also been reported. Arribas, J. et al. J. Exp. Med. 173: 423–427 (1990).

Agents which are capable of inhibiting the MCP complex are needed; such agents would provide a valuable tool for both those conducting research in the area of, for example, MCP activity, as well as those in the medical fields in order to, for example, control the deleterious effects of abnormal or aberrant MCP activity. The present invention is directed to these important ends.

SUMMARY OF THE INVENTION

The present invention is directed to novel multicatalytic protease ("MCP") inhibitors. The subject invention also comprises methods for inhibition of MCP associated with certain disorders, including the treatment of muscle wasting disorders.

In one aspect are provided compounds having formula:

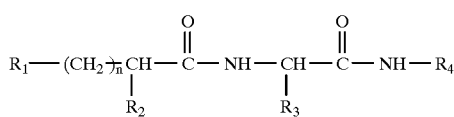

Consitutent members are defined infra, as well as preferred constituent members.

The compounds of the invention are useful in a variety of applications. For example, the compounds may be employed in research applications to further refine and develop in vitro and in vivo models for mechanistic understanding of the MCP pathway and for presentation of peptide antigens via the major histocompatibility complex class I (MHC I) pathway.

In a clinical setting, compositions comprising the claimed compounds can be used for inhibiting MCP activity, decreasing the loss of muscle mass, treating muscle wasting disorders, reducing superoxide dismutase degradation and treating disorders characterized by a reduction of superoxide dismutase activity.

Methodologies also are presented for making compounds of the invention.

These and other features of the compounds will be set forth in expanded form as the disclosure continues.

DETAILED DESCRIPTION OF THE PREFERRED EMBODIMENTS

Figure 1:
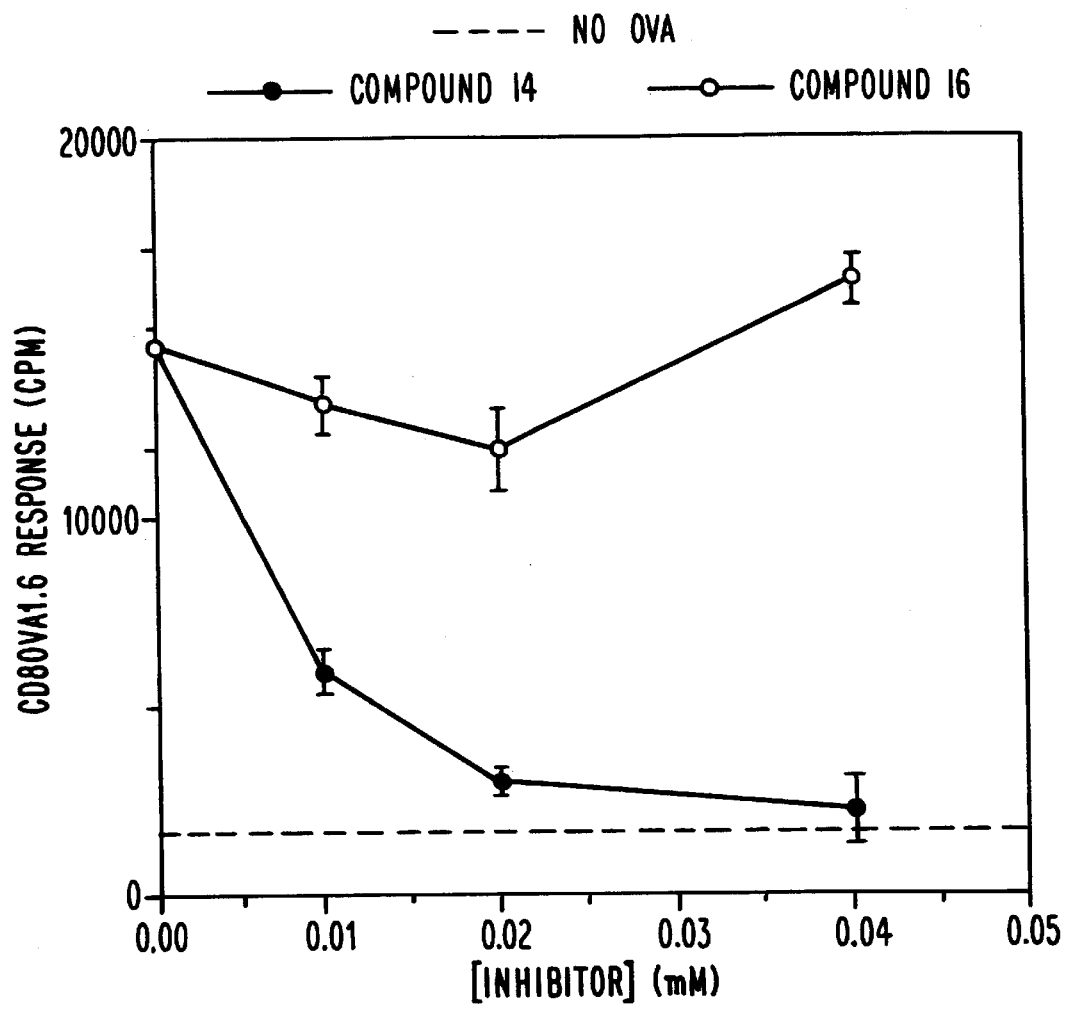
FIG. 1 shows the effect of embodiments of the disclosed MCP inhibitors on processing of electroporated OVA by M12.B6 cells.

This invention provides MCP inhibitors, compositions including these inhibitors and methods of using these inhibitors. The MCP inhibitors of the invention are represented, for example by the formula:

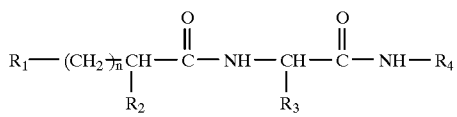

wherein:

$R_1$ is selected from the group consisting of —C≡N, —C(=O)OR$_9$, phthalimido, —NH—SO$_2$R$_9$, and —NH—J;

$R_2$ is selected from the group consisting of H, hydroxyl, alkyl having from one to ten carbons, and cycloalkyl having from three to seven carbons;

$R_3$ is selected from the group consisting of —(CH$_2$)$_m$—NH—C(=N—R$_5$)—NH$_2$, —R$_6$—NO$_2$, —R$_6$—J, and —R$_6$—CN;

$R_4$ is —CH(CH$_2$—R$_7$)—Q;

Q is selected from the group consisting of —CH—R$_8$, —C(=O)CH$_3$, —C(=O)CH$_2$Cl, —C(=O)CH$_2$Br, —C(=O)CH$_2$F, —C(=O)CHF$_2$, —C(=O)CF$_3$, —C(=O)C(=O)R$_7$, —C(=O)C(=O)NH—R$_7$, —C(=O)CO$_2$—R$_7$, —C(=O)CO$_2$H, —B(OH)$_2$,

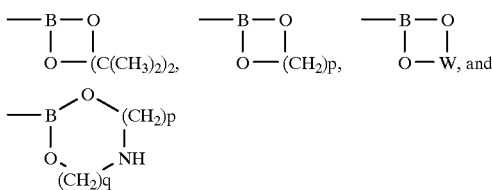

where p and q, independently, are 2 or 3;
W is cycloalkyl;
$R_5$ is selected from the group consisting of —NO$_2$, —CN, and —J;
$R_6$ is —(CH$_2$)$_m$—NH—C(=NH)—NH—;
$R_7$ is selected from the group consisting of phenyl, and alkyl having from one to eight carbons, said alkyl group being optionally substituted with one or more halogen atoms, aryl, or heteroaryl groups;
$R_8$ is selected from the group consisting of =CO, =N—NHC(=O)—NH$_2$, =N—OH, =N—OCH$_3$, =N—O—CH$_2$—C$_6$H$_5$, =NNH—C(=S)—NH$_2$ and =N—NH—J;
$R_9$ is selected from the group consisting of hydrogen and alkyl having from one to six carbons, said alkyl group being optionally substituted with one or more halogen atoms, aryl or heteroaryl groups;
J is a protecting group;
n is an integer from 3 to 10; and
m is an integer from 2 to 5.

In some preferred embodiments $R_1$ is —C≡N, —C(=O)OCH$_3$, phthalimido or —NH—SO$_2$CF$_3$, and in other preferred embodiments $R_2$ is H or cyclopentyl.

$R_3$ is preferably —(CH$_2$)$_3$—NH—C(=N—R$_5$)—NH$_2$.

Q is preferably —CH—R$_8$, —B(OH)$_2$, —C(=O)C(=O) NH—R$_7$, or has the structure:

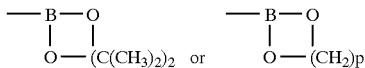

$R_5$ is preferably —NO$_2$, —CN, —PMC, —MTR, —MTS, or Tos.

$R_7$ is preferably —CH(CH$_3$)$_2$, —(CH$_2$)$_2$—CH$_3$, —CH$_2$—CH$_3$, or —C$_6$H$_5$.

$R_8$ is preferably =O, =N—OH, =N—O—CH$_2$—CH$_6$H$_5$, =NNH—C(=O)—NH$_2$ or =NNH—C(=OS)—NH$_2$.

In some preferred embodiments $R_1$ is —C(=)OCH$_3$, phthalimido or —NH—SO$_2$CF$_3$; $R_2$ is cyclopentyl; $R_3$ is —(CH$_2$)$_3$—NH—C(=N—NO$_2$)—NH$_2$; $R_7$ is —CH(CH$_3$)$_2$; and $R_8$ is =O.

In other preferred embodiments $R_1$ is —C≡N; $R_2$ is cyclopentyl; $R_3$ is —(CH$_2$)$_3$—NH—C(=N—NO$_2$)—NH$_2$ or —(CH$_2$)$_3$—NH—C(=N—J)—NH$_2$; $R_7$ is —CH(CH$_3$)$_2$; and $R_8$ is =O.

In further preferred embodiments $R_1$ is C≡N; $R_2$ is cyclopentyl; $R_3$ is —(CH$_2$)$_3$—NH—C(=N—NO$_2$)—NH$_2$ or —(CH$_2$)$_3$—NH—C(=N—J)—NH$_2$; $R_7$ is —CH(CH$_3$)$_2$; Q is —CH—R$_8$; and $R_8$ is =N—NHC(=O)—NH$_2$, =N—OH, =N—OCH$_3$, or =N—O—CH$_2$—C$_6$H$_5$.

As used herein, the term "alkyl" is; meant to include straight-chain, branched and cyclic hydrocarbons such as ethyl, isopropyl and cyclopentyl groups. Substituted alkyl groups are alkyl groups for which one or more hydrogen atoms have been replaced by halogen, other hydrocarbon groups (for example, a phenyl group), a heteroaryl group, or a group in which one or more carbon atoms are interrupted by oxygen atoms. Preferred alkyl groups have 1 to about 8 carbon atoms. As used herein, the term "halogen" has its usual meaning and includes fluorine, chlorine, bromine and iodine, with fluorine being a preferred halogen. The term "Arg" as used in the present invention has its normal meaning as the abbreviation for the amino acid "arginine."

In some embodiments compounds of thae invention contain protecting groups. As used herein, the phrase "protecting groups" is to be accorded a broad interpretation. Protecting groups are known per se as chemical functional groups that can be selectively appended to and removed from functionalities, such as hydroxyl groups, amino groups and carboxyl groups. These groups are present in a chemical compound to render such functionality inert to chemical reaction conditions to which the compound is exposed. Any of a variety of protecting groups may be employed with the present invention. One such protecting group is the phthalimido group. Other preferred protecting groups according to the invention have the following formulas:

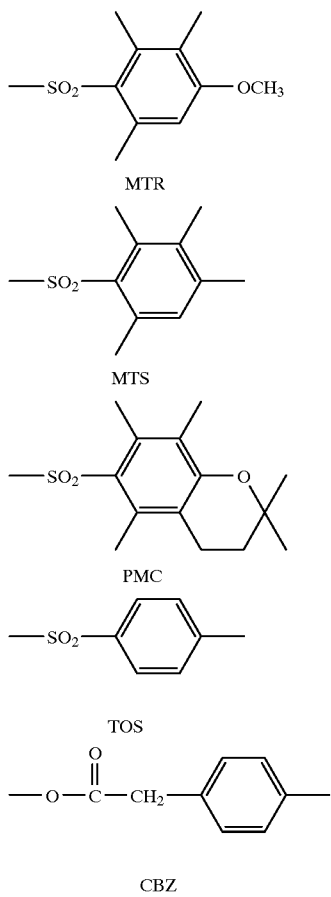

Further representative protecting groups suitable for practice in the invention may be found in Greene, T. W. and Wuts, P. G. M., "Protective Groups in Organic Synthesis" 2d. Ed., Wiley & Sons, 1991, the disclosures of which are hereby incorporated by reference in their entirety.

As previously indicated, MCP activity has been linked with a variety of disorders and diseases. Because compounds as disclosed herein are useful in inhibiting the activity of MCP, and because the usefulness of such compounds can be applied to both research and therapeutic settings, methodologies for inhibiting the activity of MCP by contacting the MCP with a compound of the invention include providing the compound to a mammal, including a human, as a medicament or pharmaceutical agent.

As used herein, the term "contacting" means directly or indirectly causing placement together of moieties to be contacted, such that the moieties come into physical contact with each other. Contacting thus includes physical acts such as placing the moieties together in a container, or administering moieties to a patient. Thus, for example, administering a compound of the invention to a human patient evidencing a disease or disorder associated with abnormal and/or aberrant activities of MCP which are associated with such disease or disorder, falls within the scope of the definition of term "contacting."

In preferred embodiments pharmaceutical compositions according to the invention are administered to patients suffering from a disorder, i.e., an abnormal physical condition, a disease or pathophysiological condition associated with abnormal and/or aberrant activities of MCP. The disorders for which the compositions of the invention are administered are preferably those which directly or indirectly produce a wasting (i.e., loss) of muscle mass, that is, a muscle wasting disorder. These include muscular dystrophies, cardiac cachexia, emphysema, leprosy, malnutrition, osteomalacia, child acute lukemia, AIDS cachexia and cancer cachexia.

In the context of the invention, "administering" means introduction of the pharmaceutical composition into a patient. Preferred methods of administration include intravenous, subcutaneous and intramuscular administration. Preferably the compound will be administered as a pharmaceutical composition comprising the compound in combination with a pharmaceutically acceptable carrier, such as physiological saline. Other suitable carriers can be found in Remington's Pharmaceutical Sciences (Mack Pub. Co., Easton, Pa., 1980).

The concentrations of the compounds described herein in a pharmaceutical composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 $\mu$g/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration. As used herein the term "patient" denotes any type of vertebrate. Preferably, the patient is a human.

The muscular dystrophies are genetic diseases which are characterized by progressive weakness and degeneration of muscle fibers without evidence of neural degeneration. In Duchenne muscular dystrophy (DMD) patients display an average of a 67% reduction in muscle mass, and in myotonic dystrophy, fractional muscle protein synthesis has been shown to be decreased by an average of 28%, without any corresponding decrease in non-muscle protein synthesis (possibly due to impaired end-organ response to anabolic hormones or substrates). Accelerated protein degradation has been demonstrated in the muscles of DMD patients.

Severe congestive heart failure (CHF) is characterized by a "cardiac cachexia," i.e., a muscle protein wasting of both the cardiac and skeletal muscles, with an average 19% body weight decrease. The cardiac cachexia is caused by an increased rate of myofibrillar protein breakdown.

Emphysema is a chronic obstructive pulmonary disease, defined by an enlargement of the air spaces distal to the terminal non-respiratory bronchioles, accompanied by destructive changes of the alveolar walls. Clinical manifestations of reduced pulmonary functioning include coughing, wheezing, recurrent respiratory infections, edema, and functional impairment and shortened life-span. The efflux of tyrosine is increased by 47% in emphysematous patients. Also, whole body leacine flux remains normal, whole-body leucine oxidation is increased, and whole-body protein synthesis is decreased. The result is a decrease in muscle protein synthesis, accompanied by a decrease in whole body protein turnover and skeletal muscle mass. This decrease becomes increasingly evident with disease progression and long term deterioration.

In diabetes mellitus, there is a generalized wasting of small muscle of the hands, which is due to chronic partial denervation (neuropathy). This is most evident and worsens with long term disease progression and severity.

Leprosy is associated with a muscular wasting which occurs between the metacarpals of the thumb and index finger. Severe malnutrition is characterized by, inter alia, severe muscle wasting.

Osteomalacia is a nutritional disorder caused by a deficiency of vitamin D and calcium. It is referred to as "rickets" in children, and "osteomalacia" in adults. It is marked by a softening of the bones (due to impaired mineralization, with excess accumulation of osteoid), pain, tenderness, muscle wasting and weakness, anorexia, and overall weight loss. It can result from malnutrition, repeated pregnancies and lactation (exhausting or depleting vitamin D and calcium stores), and vitamin D resistance.

In childhood acute leukemia there is protein energy malnutrition which results in skeletal muscle wasting. Studies have shown that some children exhibit the muscle wasting even before diagnosis of the leukemia, with an average 27% decrease in muscle mass.. There is also a simultaneous 33%–37% increase in adipose tissue, resulting in no net change in relative boded weight and limb circumference.

Cancer cachexia is a complex syndrome which occurs with variable incidence in patients with solid tumors and hematological malignancies. Clinically, cancer cachexia is manifested as weight loss with massive depletion of both adipose tissue and lean muscle mass, and is one cause of death which results from cancer. Cancer cachexia patients have shorter survival times, and decreased response to chemotherapy. In addition to disorders which produce muscle wasting, other circumstances and conditions appear to be linked in some fashion with a decrease in muscle mass. Such afflictions include muscle wasting due to chronic back pain, advanced age, long term hospitalization due to illness or injury, alcoholism and corticosteroid therapy.

Studies have shown that in severe cases of chronic lower back pain, there is paraspinal muscle wasting. Decreasing paraspinal muscle wasting alleviates pain and improves function.

It is also believed that general weakness in old age is due to muscle wasting. As the body ages, an increasing proportion of skeletal muscle is replaced by fibrous tissue. The result is a significant reduction in muscle power, but only a marginal reduction in fat-free mass.

Studies have shown that in patients suffering injuries or chronic illnesses, and hospitalized for long periods of time, there is long-lasting unilateral muscle wasting, with an average 31% decrease in muscle mass. Studies have also shown that this can be corrected with intensive physiotherapy. However, it may be more effective for many patients to effect improvement with drug therapy.

In alcoholics there is wasting of the anterior tibial muscle. This proximal muscle damage is caused by neurogenic damage, namely, impaired glycolytic and phosphorylase enzyme activity. The damage becomes apparent and worsens the longer the duration of the alcohol abuse. Patients treated with corticosteroids experience loss of muscle mass.

MCP has been shown to activate the intracellular mediator of inflammation referred to as $NF_{kappa}B$. See Baeuerle, P. A. and Henkel, T. (1994) Annu. Rev. Immunol. 12, 141–179. Inhibitors of MCP therefore potentially have use in the treatment of autoimmune and inflammatory diseases.

The compounds of the invention can be used to alleviate the muscle mass loss resulting from the foregoing conditions, as well as others. Additionally, the MCP inhibitors of the invention are useful in veterinary and animal husbandry applications to counter weight loss in animals, or to promote growth.

MCP has been implicated in the presentation of peptide antigens via the major histocompatibility complex class I (MHC I) pathway. See Goldberg and Rock, supra; see also Rock et al., Cell, 78: 761–771 (1994) hereinafter "Rock et al." Inhibitors of MCP therefore have utility as research reagents in studies where inhibition of the MCH I pathway is desired as well as in the alleviation of diseases and disorders which are associated with aberrant and/or abnormal MHC-I processing of antigens. Because the precise origin of most of the peptides presented on MHC-I molecules is still not clear and because evidence has recently accumulated that MCP may play a role in MHC-I presentation (see Rock et al. supra), reagents such as the disclosed MCP inhibitors which block the proteolytic processing of antigens for MHC-I presentation would be useful in resolving the importance of this pathway.

Surprisingly, it has also been found that MCP inhibitors of the invention are also useful in enhancing the activity of Cu/Zn superoxide dismutase-1 ("SOD-1") enzyme. Accordingly, these compounds are useful in both research settings for the investigation of SOD-1 deficient systems and in the treatment of neurodegenerative or other disorders characterized by a reduction in SOD-1 enzyme activity (i.e., wherein such a reduction has been implicated in the pathogenesis of the disorder). Such conditions include diseases involving oxidative stress such as Parkinson's disease, Alzheimers's disease, Huntington's disease, stroke, trauma, and ischemia.

SOD-1 is a homodimeric metalloenzyme that catalyzes the dismutation of the toxic superoxide anion $O_2$ to $O_2$ and $H_2O_2$. SOD-1 is a scavenger of free radicals and therefore acts as a first line defense in the detoxification of superoxide radicals, which are normal by-products of aerobic metabolism. SOD-1 occurs primarily in eukaryotes and is found in the cytoplasm of virtually all cell types. SOD-1 is an essential enzyme in the physiological response to oxygen toxicity and has been actively investigated as a therapeutic agent in pathological conditions related to oxidative stress. See Bannister et al., CRC Crit. Rev. Biochem. 22: 111–180 (1987); Halliwell et al., Methods in Enzymol., 186: 1–75 (1990); Greenwald, Free Rad. Biol. Med. 8: 201–209 (1990).

Features that have prevented the use of SOD-1 as a therapeutic agent are its poor intracellular access when supplied exogenously, and its extremely short half-life in serum. Therefore, compounds that enhance the activity of intracellular SOD-1 would provide a significant advancement in SOD-1 therapy.

ALS is a progressive paralytic disorder caused by degeneration of large motor neurons of the spinal cord and brain. Approximately 5–10% of ALS cases are familial (FALS) and are inherited as an autosomal dominant trait. Recently, sixteen different missense mutations have been identified in a subset of families with FALS and occur within the gene encoding SOD-1. See Rosen, D. R., et al., Science 261:1047–1051 (1993); Deng, H.-X., et al., Nature 362:59–62 (1993). These mutations lead to a decrease in SOD-1 activity in red blood cells and brain tissue, and have been shown to destabilize the SOD-1 protein resulting in increased turnover of the enzyme. See Bowling, A. C., et al., J. Neurochem. 61: 2322–2325 (1993); Borchelt, D. R., et al., Proc. Natl. Acad. Sci. 91: 8292–8296 (1994). Additionally, a transgenic-mouse model of ALS, based upon the implication of the connection between SDD-1 and ALS, has been described. Brown, R. H. 331/16 NEJM 1901 (1994).

We have discovered that our MCP inhibitors are potent positive effectors of SOD-1. A preferred MCP inhibitor, referred to herein as "Compound 14," specifically reduces wild-type and mutant SOD-1 degradation in a dose-dependent manner (compound number designations are based upon the Example number which discloses the synthesis of the compound, e.g., the synthesis of Compound 14 is set forth in Example 14, infra). As used herein, reduction of SOD-1 degradation means retarding the rate at which the SOD-1 protein is catabolized.

The invention is further illustrated by way of the following examples. These examples are intended to further elucidate the invention, and are not intended to limit the scope of the appended claims.

EXAMPLE 1

Isolation of multicatalytic protease from human tissues

Samples of human liver and brain obtained post-mortem were used for isolation and partial purification of MCP by ion-exchange chromatography, ammonium sulfate precipitation, and gel filtration (e.g., Driscoll and Goldberg, Proc. Natl. Acad. Sci. 86, 787–791 (1989); Yamamoto et al., Biochim, Biophys. Acta 882, 297–304 (1986). For either starting material, tissue was homogenized in 10 volumes of 20 mM Tris-HCl (pH 7.5) containing 20% glycerol. Following centrifugation at 40,000×g for 30 minutes, proteolytic activity of the chymotrypsin-like component of MCP could be detected in the supernatant (see below). The supernatant was fractionated on a DEAE-Sepharose Fast Flow column equilibrated in homogenization buffer. For each liter of supernatant, 250 ml of resin was used. Following sample loading, the column was washed with ~10 volumes homogenization buffer, and proteins were eluted with a linear NaCl gradient of from 0 to 400 mM (21 for 250 ml resin). Fractions were assayed for MCP activity, and the active fractions were pooled and subjected to precipitation with $(NH_4)_2SO_4$ at 80% saturation. Precipitated proteins were collected by centrifugation, resuspended in homogenization buffer, and loaded on a Sephacryl S300HR column (500 ml resin volume) that had been standardized using bovine serum albumin (68 kDa). A single peak of MCP activity was eluted with a molecular weight of ~650 kDa. This preparation was free of other measurable proteolytic activities and maintained its MCP activity upon storage at 4° C. for >6 months. This preparation was used for most of the experiments. Further fractionation of the preparation on an hydroxyapatite-Ultrogel column (Yamamoto et al., supra) yielded a more highly purified enzyme, which according to denaturing SDS-polyacrylamide gel electrophoresis was comprised of the expected >10 subunits ranging in $M_r$ from 20 to 35 kDa.

EXAMPLE 2

Assay for chymotrypsin-like and trypsin-like activities of MCP

The procedure for MPC isolation described above generated an enzyme complex whose proteolytic activities were latent, but which could be activated by addition of low concentrations (0.02–0.05%) of SDS (Yamamoto et al., supra). The chymotrypsin-like activity was assayed according to the following procedure: in 96 well microtiter plates, human MCP was diluted 4 to 10-fold in homogenization buffer containing 0.04% SDS. A calorimetric substrate MeOSuc-EVKM-para-nitroanilide (methoxysuccinyl-Glu-Val-Lys-Met-pNa), purchased from Bachem Bioscience Inc., King of Prussia, Pennsylvania was added to a final concentration of 100 μM from a stock solution of 10 mM in dimethylsulfoxide. Reaction volumes were 200 μl per well. After incubation for various periods of time at 37° C., the concentration of free pNa was determined on a Biotech EL-340 microplate reader, reading absorption at 490 nm. Protease activity was determined under conditions in which substrate hydrolysis increased linearly with time and the change in absorption was proportional to the concentration of free pNa. Alternatively, a fluorogenic substrate was used, methoxysuccinyl-Phe-Leu-Phe-amidomethylcoumarin (Enzyme Systems Products, Dublin, Calif.), and the change in fluorescence monitored at an excitation of 390 nm, and an emission at 460 nm.

The trypsin-like activity of human MCP was assayed as described above with the following modifications. Reactions were carried out in Tris-glycerol buffer (pH 9.5) supplemented with 1 mM 2-mercaptoethanol, and the substrate was a fluorogenic substrate, Benzyloxycarbonyl—Phe—Arg—AMC (100 μM).

After incubation for various periods of time at 37° C., the concentration of free AMC was determined on a Fluoroskan II spectrofluorimeter with an excitation filter of 390 nm and an emission filter of 460 nm. Protease activity was determined under conditions in which substrate hydrolysis increased linearly with time and the change in fluorescence was proportional to the concentration of free AMC.

EXAMPLE 3

Determination of $IC_{50}$ values for MCP Inhibitors $IC_{50}$ values are typically defined as the concentration of a compound (in this case, the disclosed MCP inhibitor) necessary to produce 50% inhibition of the enzyme's activity. $IC_{50}$ values are useful indicators of the activity of a compound for its designated use. Preferably, the inhibitors of the invention have $IC_{50}$ values of less than about 10 micromolar.

Inhibition of the chymotrypsin-like or trypsin-like activity of MCP was determined by incubating the enzyme with various concentrations of putative inhibitors for 15 minutes at 37° C. prior to the addition of substrate. Each experimental condition was evaluated in triplicate, and replicate experiments were performed for the inhibitors described herein.

EXAMPLE 4

Demonstration of Inhibition of Cellular Muscle Breakdown: Inhibition of Unweighting Atrophy in Juvenile Rats The effect of several inhibitors on the unweighting atrophy of the soleus muscle in juvenile rats was determined. See Tischler, M. E. (1990) Metabolism 39/7: 756–763 (hereinafter "Tischler—1990") for a general discussion of the procedure.

Juvenile female Sprague-Dawley rates (80–90 g) were tail-cast, hind limb suspended as in Jetspers, S. R. and Tischler, M. E., (1984) J. Appl. Physiol. 57: 1472–1479. The animal's hind limbs were elevated above the floor of the cage with each animal housed individually. Animals had free access to food and water, and were weighed at the time of suspension and at time of termination. During the suspension period the animals were checked daily to ensure that their toes were not touching the floor of the cage, and that there was no swelling of the tail due to the cast.

A. Experimental Design—Part 1

Each experiment began with the suspension of 20 rats which were randomly divided into 4 groups of 5 animals each. Group A was suspended for just 2 days and provided baseline data to approximate the soleus muscle size in other animals suspended for longer times. Average body weights for the groups at the outset of the study were compared and used as a correction factor for body size differences. Group B was a second control group which had the soleus of one limb treated with an aqueous solution of mersalyl after two days of unweighting, to demonstrate the ability to slow muscle atrophy during unweighting, for each group of animals. Mersalyl has been previously studied and demonstrated to prevent atrophy in an in vivo model substantially as described in the protocol utilized herein. See Tischler—1990. At 2 days after unweighting commenced, an aqueous solution of mersalyl (200 nM; 4 µl/100 g initial body wt) was injected into one soleus, as described previously. The contralateral muscle was injected with a similar volume of 0.9% saline ("Vehicle"). The animals were maintained under Innovar-vet (10 µl/100 g body wt) tranquilization during the in situ injection procedure. After the injections, the animals were suspended for an additional 24 hours and the soleus was removed. Groups C and D for each experiment were used for testing each of two different embodiments of the disclosed compounds.

Animals were treated as in group B, except that 1 mM MCP inhibitor, contained in dimethysulfoxide (DMSO), was injected into the soleus of one leg and DMSO only into the contralateral soleus. Thus each experiment consisted of two control groups and the testing of MCP inhibitors of the invention. The completion of five such experiments with different pairs of inhibitors provided for an "n" value of 10 for testing each MCP inhibitor and with each tested in two different shipments of animals.

B. Processing of the Soleus Muscle—Part 1

After the animal was sacrificed, the soleus was excised, trimmed of fat and connective tissue, and carefully weighed. The muscle was then homogenized in 10% trichloroacetic acid (TCA) and the precipitated protein pelleted by centrifugation. The pellet was then washed once with 10% TCA and once with ethanol:ether (1:1). The final pellet was solubilized in 4 ml of 1N sodium hydroxide. The sample was then analyzed for protein content by the biuret procedure, using albumin as a standard.

C. Data Analysis—Part 1

The effect of MCP inhibitors on total muscle protein content was examined primarily by paired comparison with the untreated contralateral muscle. The ratio of contents was calculated and then analyzed statistically by analysis of variance ("ANOVA"). The left leg was always the treated leg so that the protein content ratios could be compared to the non-treated control animals as well. In this way, a significant difference can be shown by comparing the protein content of the two legs, as well as the relative effectiveness of the tested MCP inhibitors. A paired student test was also performed for the effect of each separate treatment. The non-treated control data also provided an estimate of protein content of day 2. This allowed approximation of the protein changes over the 24 hours of treatment for each of the Groups B, C, and D.

D. Experimental Design—Part 2

Each experiment consisted of 10 animals with groups of 5 animals being tested with one of the inhibitors for its effect on protein synthesis. Control animals were not needed for this aspect of the study as the contralateral DMSO-treated muscle served as the paired control for the inhibitor-treated muscle. Each group was injected as described for groups C and D in part 1. Twenty-four hours after the in situ treatment the fractional rate of protein synthesis was analyzed in both soleus muscles. Each muscle was injected with a 0.9% saline solution (3.5 µl/100 g final body wt) containing $^3$H-phenylalanine (50 mM; 1 µCi/µl). Fifteen minutes later the middle two-thirds of the muscle was excised and the muscle was processed as described below.

E. Processing of the Soleus Muscle—Part 2

The muscle was first washed for 10 minutes in 0.84% saline containing 0.5 mM cycloheximide, to terminate protein synthesis, and 20 mM cycloleucine, to trap phenylalanine in the cell. The muscle was then homogenized in 2.5 ml of ice-cold 2% perchloric acid. The precipitated protein was pelleted by centrifugation. One aliquot of the supernatant was taken for liquid scintillation counting and another aliquot was processed for conversion of phenylalanine to phenethylamine to determine the soluble phenylalanine concentration fluorometrically. See Garlick, P. J. et al,, *Biochem. J.*, 192 719–723 (1980) and Munoz, K. M. et al., .1993 *Meatbolism*, in press. These values provide the intracellular specific activity. The specific activity of phenylalanine in the muscle protein was determined after hydrolyzing the protein by heating in 6N HCl. The amino acids released were solubilized in buffer. One aliquot was taken for scintillation counting and another for analysis of phenylalanine as for the supernatant fraction. The fractional rate of protein synthesis was calculated as: protein specific activity/intracellular specific activity x time.

F. Data Analysis—Part 2

Analyses of protein synthesis were on a paired basis for each MCP inhibitor. Student paired t test comparisons of the contralateral muscles determined whether there was any effect of the inhibitor on protein synthesis. Protein breakdown can be calculated approximately as the fractional rate of protein synthesis (from part 2) plus the fractional rate of protein accretion (from part 1), where protein loss yields a negative value for protein accretion.

Qualitatively the ability of MCP inhibitors to slow protein loss without affecting protein synthesis indicates a slowing of protein degradation.

G. Results

Table 1 shows the lack of effect of the MCP inhibitors on control muscle.

Table 2 shows the change in protein content during the third day of unweighting.

Table 3 shows the effect of the MCP inhibitors on unweighted muscle protein.

Table 4 shows the effect of the MCP inhibitors on unweighted muscle synthesis. In the Tables, the compound number refers to the Example number where the synthesis route for the compound is set forth.

TABLE 1

Lack of Effect of MCP Inhibitors on Control Muscle

| | Protein (mg/muscle) | |
|---|---|---|
| Treatment | Vehicle | Treatment |
| DMSO | 5.9 | 6.7 |
| Compound 34 | 6.1 | 6.3 |
| Compound 14 | 6.0 | 6.1 |
| Compound 20 | 5.7 | 5.9 |

TABLE 2

Change in Protein Content During Day 3 of Unweighting

| | Protein (mg/muscle) | | Effect | |
|---|---|---|---|---|
| Treatment | Start | End | (%) | P |
| Saline | 6.5 | 5.7 | −12 | <0.001 |
| DMSO | 6.5 | 5.9 | −10 | <0.001 |
| Mersalyl | 6.4 | 6.6 | +3 | <0.05 |
| Compound 34 | 6.3 | 6.6 | +5 | <0.05 |
| Compound 14 | 6.8 | 6.4 | 0 | >0.1 |
| Compound 20 | 6.5 | 6.2 | −4 | <0.07* |
| Compound 16 | 6.3 | 6.0 | −5 | <0.07* |

*marginally significant values

TABLE 3

Effect of MCP Inhibitors on Unweighted Muscle Protein

| | Protein (mg/muscle) | | Effect | |
|---|---|---|---|---|
| Treatment | Vehicle | Treatment | (%) | P |
| Mersalyl | 5.7 | 6.6 | 14 | <0.001 |
| Compound 34 | 5.9 | 6.6 | 12 | <0.001 |
| Compound 14 | 6.0 | 6.4 | 7 | <0.06* |
| Compound 20 | 5.9 | 6.2 | 5 | <0.95 |
| Compound 16 | 5.9 | 6.0 | 0 | >0.1 |

*marginally significant values

TABLE 4

Lack of Effect of MCP Inhibitors on Unweighted Muscle Synthesis

| | Protein (mg/muscle) | |
|---|---|---|
| Treatment | Vehicle | MCP Inhibitor |
| Compound 34 | 14.5 | 13.3 |
| Compound 14 | 13.1 | 13.8 |
| Compound 20 | 14.1 | 14.6 |

EXAMPLE 5
Demonstration of MCP Inhibition Using MHC-1 Processing

Compounds of the invention were assayed for the ability to inhibit the processing of exogenous OVA antigen by the class I major histocompatibility pathway (MHC-I). The MCP inhibitors were applied to a functional antigen processing system that allows inclusion of the inhibitor within the antigen processing cell during exposure to antigen, followed by fixation of the processing cell. T cell hybridomas are then added to the processing cells in the absence of inhibitor to determine the expression of peptide-MHC-I complexes, which reflects antigen processing prior to fixation.

A. Cell Culture

Cells were grown at 37° C. in a humidified atmosphere maintained at 5% $CO_2$ in a standard medium: DMEM (Gibco, St. Louis, Mo.) with 10% fetal calf serum (Hyclone, Logan Utah), $5 \times 10^{-5}$M 2-mercaptoethanol, antibiotics and the following supplements: L-arginine HCl (116 mg/L), L-asparagine (36 mg/L), $NaHCO_3$ (2 g/L), sodium pyruvate (1 mM). See also Harding, C. V., (1992) *Eur. J. Immunol.* 22: 1865–1869. M12.B6 cells (generous gift of Osami Kanagawa, Washington University, ST. Louis, Mo.) were used for antigen presentation; they were created by fusing M12.C3 murine B lymphoma cells with LPS-stimulated splenocytes (source of B lymphoblasts) from a C57BL/6 mouse. Accordingly, they express the H-$2^b$ antigens. DOWB T hybridoma cells are specific for the OVA (323–339) peptide bound to either I-A$^b$ or I-A$^d$. See Yewdell et al., *Science* 1988 239: 637. B3.1 T hybridoma cells respond to OVA (258–276)-K$^b$.

B. Electroporation and antigen processing studies

To be processed and presented by the MHC-1 pathway, the exogenous antigen (ovalbumin; OVA) must penetrate into the cytosol of the processing cells. OVA was introduced into the cytosol of processing cells (M12.B6 cells) by means of electroporation.

Electroporation was performed with a Gibco BEL Electroporator using 0.4 cm gap cuvette chambers. Capacitance was 800 μF and voltage was 50–300 V. Electroporation was performed in serum-free RPMI or PMEM (Gibco) with $1.5 \times 10^7$ M12.B6 cells/ml ($0.5 \times 10^7$–$4.0 \times 10^7$ range) in the presence of OVA at 4° C. The cells were immediately placed on ice. Various inhibitors were then added and the cells were transferred to 18° C. or 37° C. Finally the cells were lightly fixed for about 10 minutes with 1% paraformaldehyde and washed extensively at 37° C., preventing further processing. The extent of processing, (i.e., the level of specific peptide-MHC complexes expressed) was determined by the ability of the M12.B6 cells to stimulate IL-2 secretion by B3.1 or DOBW T hybridoma cells. T cells ($10^5$) were plated with the M12.B6 cells ($2 \times 105$ if fixed, $5 \times 10^4$ if viable) in 0.2 ml for 18–24 hours at 37° C. in a $10^2$ chamber. Both T hybridomas respond to antigen stimulation by the secretion of IL-2 (assayed in the supernatants by IL-2-dependent CTLL cell proliferation and [$H^3$] thymidine incorporation. See Allen et al., *J. Imunol.* 132: 1077).

Figure 2:
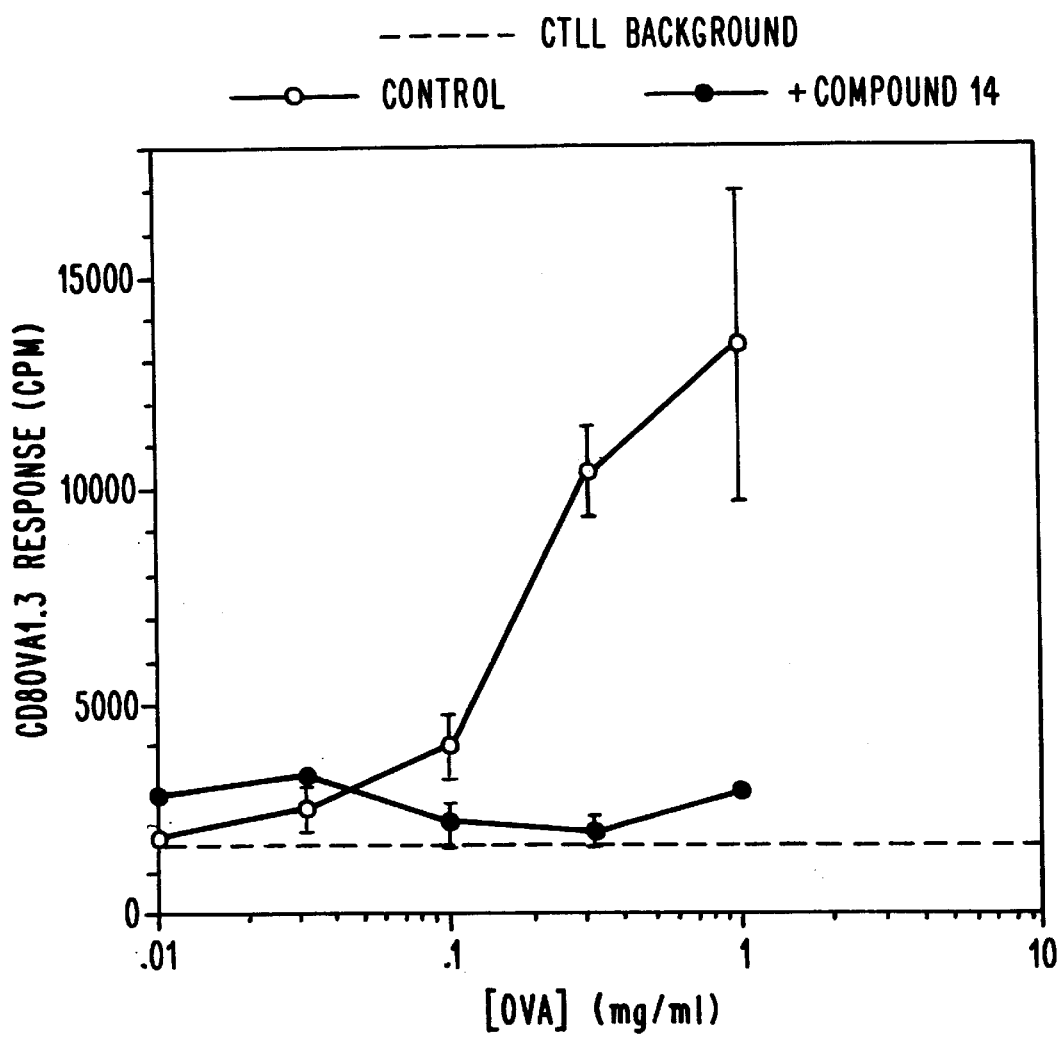
FIG. 2 shows the effect of OVA concentration on the inhibition of processing by an embodiment of the invention.
Figure 3:
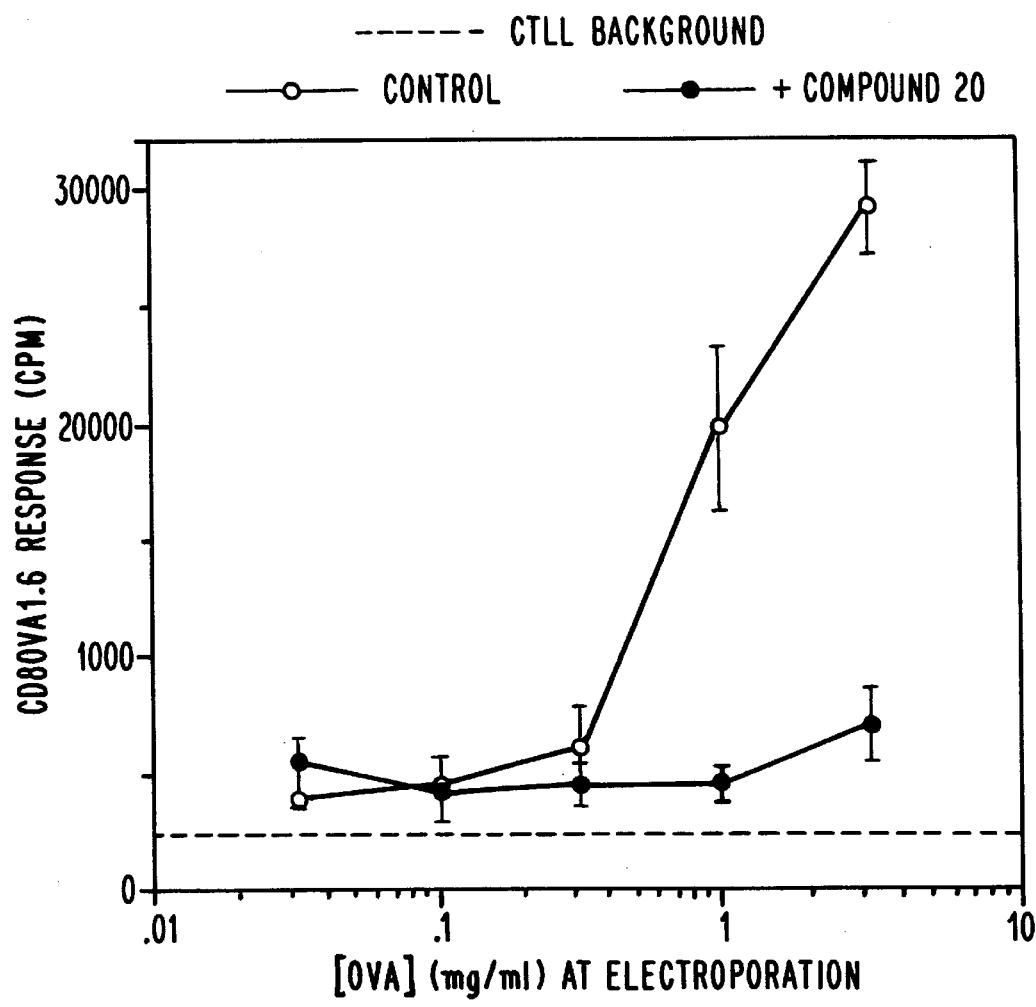
FIG. 3 shows the effect of OVA concentration on the inhibition of processing by an embodiment of the invention.

Results of these studies are shown in FIGS. 1–3. FIG. 1 shows the effects of Compounds 14 and 16 on the processing of electroporated OVA by M12.B6 cells. FIGS. 2 and 3 show the effect of Compounds 14 and 20 on MHC-1 OVA processing. Both compounds effectively inhibit OVA processing. These data provide additional support for MCP inhibitory effect of the compounds of the invention. It is accepted that the classical MHC-I pathway involves antigen degradation by proteasomes. See Goldberg et al., supra. Thus, the compounds can be utilized in further understanding the importance of the proteolytic processing of antigens.

EXAMPLE 6

A. Reduction of Cu/Zn Superoxide Dismutase (SOD-1) Degradation

I. Part 1—Cloning and mutagenesis.

A mouse SOD-1 cDNA clone was obtained from Jim Mahaffey (North Carolina State University, Raleigh, N.C.). This clone was modified by polymerase chain reaction (PCR) methodologies to incorporate 1) a Kozak translation initiation consensus signal (i.e., 5'-GCCGCCACC-3') directly upstream of the ATG start codon, 2) a Hind III restriction site 5' of this consensus signal and 3) an Xho I restriction site at the 3' terminus of the cDNA. The oligonucleotide primers used for the PCR procedures were: 5' primer (EH87)=5'-TCGATCGAAGCTTGCCGCCACCATGGCGATGAAAGC-3' (SEQ ID NO:1), 3' primer (EH88)=5'-AGCTAGCCTCGAGCAGATTACAGTTTAATG-3' (SEQ ID NO:2). The resulting PCR product was digested with the restriction enzymes Hind III and Xho I and cloned into the Hind III+Xho I digested vector pBluescript II SK+ (Stratagene Cloning Systems, La Jolla, Calif.) to yield pSK-HX2.

The FALS point mutations at amino acid 4 (Ala$^4$→Val) (GCG→GTG) and amino acid 113 (Ile$^{113}$→Thr) (ATT→ACT) were introduced into the SOD-1 cDNA clone pSK-HX2 using the overlap extension PCR mutagenesis procedure described by Ho et al., Gene 77: 51–59 (1989). The Ile$^{113}$→Thr mutant was constructed as follows: the 5' PCR fragment was generated using the 5' primer E.H78; consisting of the nucleotide sequence 5'-TTAATCCTCACTCTAAGAAAC-3' (SEQ ID NO:3) (nucleotides 193 to 213 of SOD1 cDNA where #1 is the A of the ATG; start codon) and the 3' primer EH84; consisting of the nucleotide sequence 5'-TTGTACGGCCAGTGATGGAATGCT-3' (SEQ ID NO:4) (nucleotides 351 to 328), the 3' PCR fragment was constructed using the 5' primer EH83; consisting of the nucleotide sequence 5'-AGCATTCCATCAfTGGCCGTACAA-3' (SEQ ID NO:5) (nucleotides 328 to 351) and the 3' primer EH42; consisting of the nucleotide sequence 5'-TAATACGACTCACTATAGGG-3' (SEQ ID NO:6) (nucleotides 626 to 645 of pBluescript II SK+). Fifty nanograms of both 5' and 3' PCR fragments were combined in the second step PCR reaction and amplified using primers EH78 and EH42. This PCR product was digested with Bal I and Xho I and cloned into Bal I+Xho I digested pSK-HX2 thus replacing the native 255 bp Bal I/Xho I fragment with the FALS mutant fragment (clone pSK-113).

Figure 4:
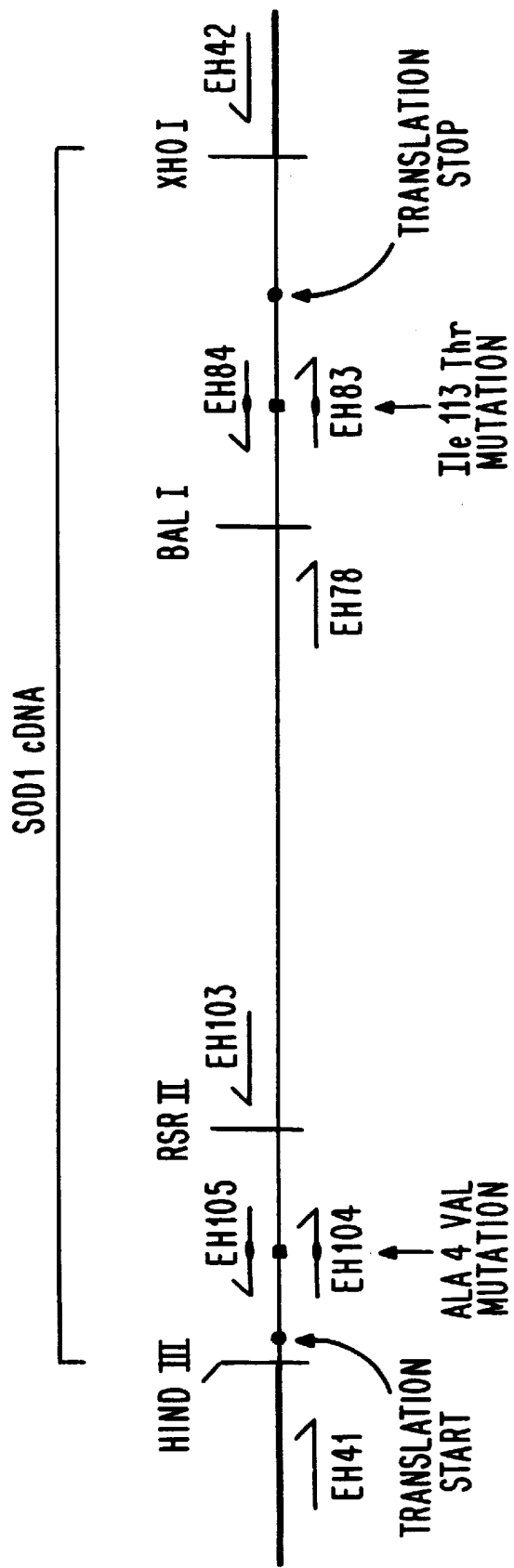
FIG. 4 shows a physical map defining the SOD-1 gene and the location of the FALS mutations, restriction sites and the PCR primers.

The Ala$^4$→Val mutant was constructed as follows: the 5' PCR fragment was generated using the 5' primer EH105; consisting of the nucleotide sequence 5'-GCACAC-CACTTTCATCGCCATGGTGGCGGCAAGCTTCGATC-3' (SEQ ID NO:7) (nucleotides +21 to –20) and the 3' primer EH41; consisting of the nucleotide sequence 5'-ATTAACCCTCACTAAAGGGA-3' (SEQ ID NO:8) (nucleotides 792 to 773 of pBluescript II SK+). The 3' PCR fragment was generated using the 5' primer EH104, consisting of the nucleotide sequence 5'-GATCGA-AGCTTGCCGCCACCATGGCGATGAAAGTGGTGTGC-3' (SEQ ID NO:9) (nucleotides –20 to +21) and the 3' primer EH103; consisting of the nucleotide sequence 5'-CTTCAGTTAATCCTGTAA-3' (SEQ ID NO:10) (nucleotides 123 to 106). As above, 50 ng of both 5' and 3' PCR fragments were combined in the second step PCR reaction and amplified using primers EH41 and EH103. This PCR product was digested with Hind III and Rsr II and cloned into Hind III+Rsr II digested pSK-HX2 thus replacing the native 51 bp Hind III/Rsr II fragment with the FALS matant fragment (clone pSK-A4V). All PCR products describes above were sequenced using the Sequenase method (US Biochemical, Cleveland, Ohio) to confirm the presence of the mutations and the absence of any PCR errors. An illustration of the SOD-1 gene defining the locations of the mutations, primers and restriction sites is shown in FIG. 4.

The SOD-1 cDNA expression vectors were constructed by digesting the wild-type (pSK-HX2) and mutant constructs (pSK-113 and pSK-A4V) with Hind III and Xho I. Each of the three resulting 546 bp fragments containing the SOD-1 CDNA sequences were separately cloned into Hind III+Xho I digested pcDNA I/Neo (Invitrogen Corp., San Diego, Calif.) to yield, respectively, pCMV-HX5 (wild-type SOD), pCMV-113 (Ile$^{113}$→Thr), and pCMV-A4V (Ala$^4$→Val).

II. Part 2.

Initial experiments were conducted to determine whether the reduced stability of the FALS mutant SOD-1 proteins was due to MCP-mediated proteolytic degradation. The human kidney cell line designated 293 (human 293 cells or 293 cells)was obtained from the American Type Culture Collection (ATCC), 12301 Parklawn Drive, Rockville, Md., 20852 (ATCC #CRL 1573) and grown in Dulbecco's modified Eagle's medium with 4.6 g/L glucose, 10% heat-inactivated horse serum (Gibco/Life Technologies Inc. Gaithersburg, Md.). The human 293 cells were maintained at 37° C. in an atmosphere of 5% $CO_2$. The 293 cells were transiently transfected using the calcium phosphate method (Chen, C. et al., Biotechniques 6: 632 (1988). The pCMV-113 SOD-1 expression vector was introduced into 293 cells and 24 hours later, the cells were incubated with either compound 34, compound 14, or compound 24, all at a concentration of 5 $\mu$M, for a duration of 24 hours. The known MCP and other protease inhibitory compounds were solubilized in dimethyl sulfoxide (DMSO). Other 293 cell cultures were incubated with an equal volume of DMSO or left in medium only as negative controls.

Figure 5:
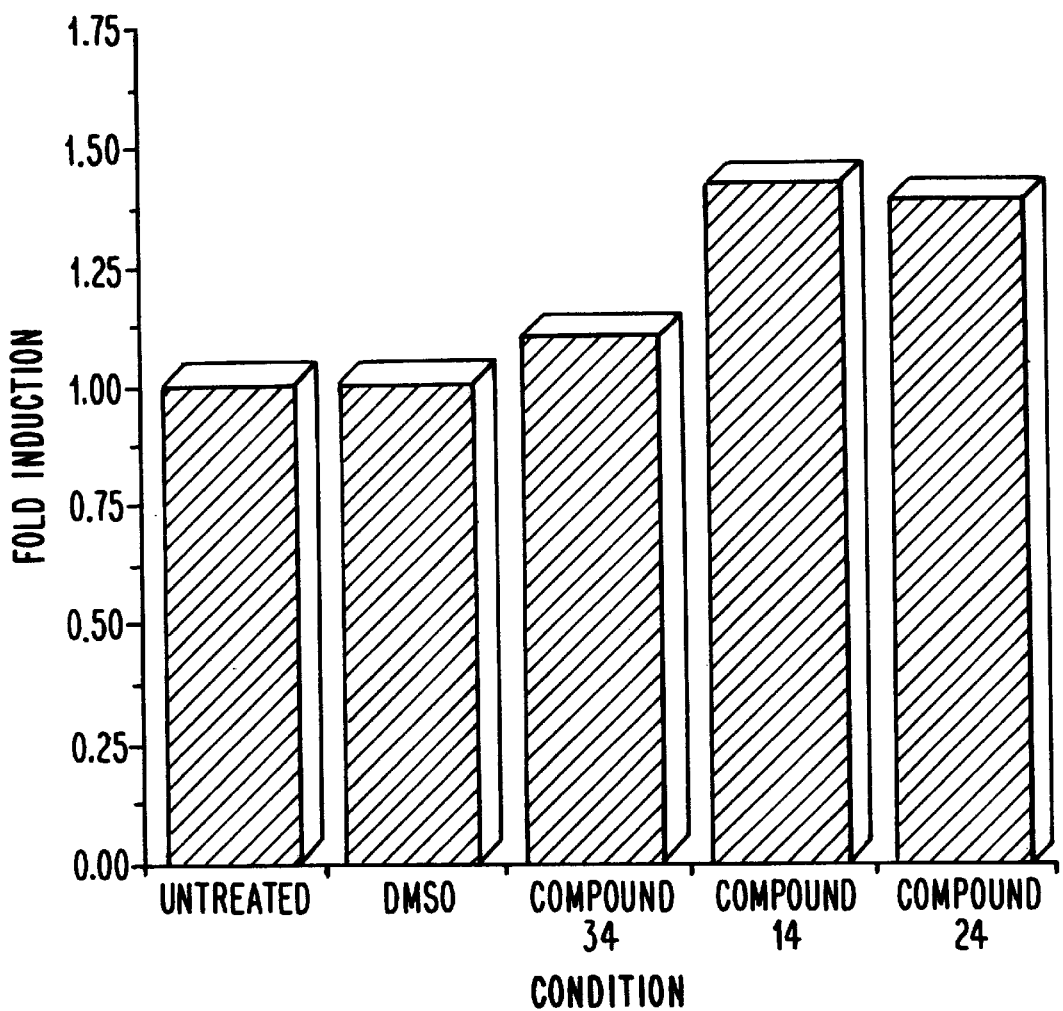
FIG. 5 shows the quantitation of SOD-1 levels in transiently transfected 293 cells after incubation with 5 $\mu$M of embodiments of the MCP inhibitors.

Approximately 48 hours prior to receiving test compounds, $5 \times 10^5$ 293 cells were seeded in 36 mm dishes and maintained at 37° C. in an atmosphere of 5% $CO_2$. Cells were incubated with MCP inhibitors (compound 34, 14 or 24) or with DMSO as a negative control for a duration of 24 hours. Cell lysates were prepared by lysing the cells in approximately 75 $\mu$l of phosphate-buffered saline (PBS) by freeze/thaw cycling. Protein concentrations of the cell lysates were determined using the BCA method (Pierce, Rockford, Ill.) and 2 to 2.5 $\mu$g of each sample was electrophoresed on a 4–20% polyacrylamide geol (Novex, San Diego, Calif.) using a Tris/glycine/SDS (25 mM Tris/192 mM glycine/0.1% SDS) buffer system. Proteins were transferred to nitrocellulose filters by electroelution and filters were blocked by incubation in blotto solution (5% dry milk in 25 mM Tris-buffered saline (1× TBS)) for 30 minutes. Filters were transferred to primary antibody solution (1:10, 000 dilution in blotto solution) and incubated for 2–18 hours. The primary antibody used in these studies was polyclonal rabbit antiserum raised against purified mouse SOD-1 produced in *E. coli* (Hazelton Research Products, Denver, Pa.). The filters were washed three times for 5 minutes each in 1×0 TBS and incubated in secondary antibody solution (1:2,000 dilution in blotto solution) for two hours. The secondary antibody was a goat anti-rabbit IgG conjugated to alkaline phosphatase (Bio-Rad, Richmond, Calif.). Filters were washed three times for 5 minutes each in 1× TBS and stained for alkaline phosphatase activity by incubation for 5–60 minutes in a commercially available alkaline phosphatase detection reagent (Bio-Rad, Richmond, Calif.). Stained bands corresponding to SOD-1 protein were quantitated using a DocuGel V image analysis system and RFLPscan software (Scanalytics, Billerica, Mass.). Levels of SOD-1 are expressed as units of induction relative to the negative control (i.e., units of experimental divided by units of control). Immunoblot analysis of cell lysates revealed that SOD-1 levels were modestly elevated compared to those of controls in each of the three samples incubated in the presence of MCP inhibitors (FIG. 5). These results show that inhibition of the MCP by the compounds of the invention leads to increased accumulation of SOD-1 protein in the Ile$^{113}$→Thr mutant and thereby implicates MCP as being responsible for the reduced levels of SOD-1 in the cells containing the FALS mutation.

III. Part 3.

To further show that MCP activity is responsible for SOD-1 turnover, studies were conducted on cell lines stably producing wild-type mouse SOD-1 or the FALS mutant proteins, i.e., Val in place of Ala$^4$ and Thr in place of Ile$^{113}$. Cell lines stably expressing mouse native SOD-1 and the two FALS mutant SOD-1 proteins mentioned above were derived by calcium phosphate transfection (Chen, C. et al., Biotechniques 6: 632 (1988)) of 293 cells with SOD-1 cDNA expression constructs (described above) followed by selection for neomycin resistance by growth in the presence of 1 mg/ml G418 (Geneticin™, Gibco/Life Technologies, Inc., Gaithersburg, Md.). Cells were maintained in G418 selection for three weeks at which time drug selection was removed and the G418-resistant colonies of each transformed cell type were pooled for further growth. Compound 14 was utilized in these studies.

Figure 6:
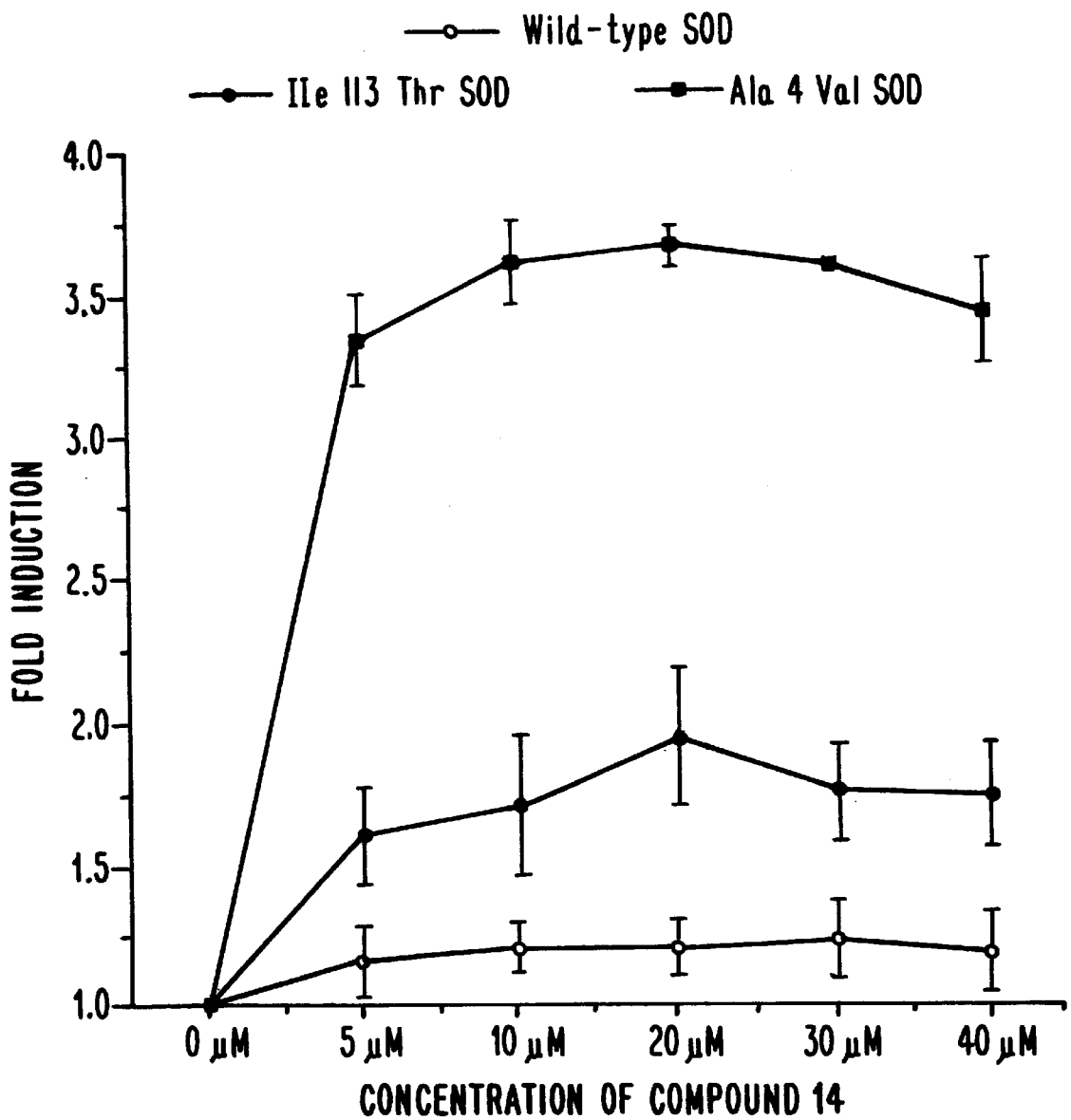
FIG. 6 shows the dose response of various SOD-1 isoforms to an embodiment of the invention.

Cell lines expressing the indicated SOD-1 isoforms were incubated with various concentrations of compound 14 for 24 hours at which time the SOD-1 levels were measured by densitometric scanning of immunoblots. Levels of SOD-1 are expressed as units of induction relative to the samples from negative controls (as above) and each data point is the average of three experiments. Dose response analysis of Compound 14 indicated that incubation of the transformed cells with this MCP inhibitor led to significant accumulations of SOD-1 protein levels with maximal accumulations occurring in those cells incubated with Compound 14 at a concentration of approximately 20 μM (FIG. 6). Moreover, the magnitude of SOD-1 accumulation correlates with the estimated half-lives of the various SOD proteins; wild-type SOD-1 being the most stable and Ala$^4$→Val the least stable (Borchelt D. R. et al., Proc. Natl. Acad. Sci. 91: 8292–8296 (1994)). These data are consistent with the hypothesis that the FALS mutations destabilize the SOD-1 proteins, possibly due to misfolding, and as a result of structural alterations resulting from the mutations target these proteins for degradation by MCP. These results also demonstrate that Compound 14 has a statistically significant effect on turnover of the wild-type SOD-1 protein further supporting the role of the MCP in SOD-1 degradation.

IV. Part 4.

To demonstrate the specificity of MCP activity in SOD-1 turnover (and rule out the possible involvement of other major proteolytic pathways such as the calcium-activated protease calpain and the lysosomal. proteases), experiments were performed in which two transformed cell lines (described above, one producing wild-type protein and the other SOD-1 protein, with the Ala$^4$→Val mutation), were incubated with various protease inhibitors each of which is specific for a unique proteolytic activity: Compound 14 inhibits MCP; "Calpeptin" (Novabiochem USA, La Jolla, Calif., cat no.03-34-0051; CBZ-Leu-Nle-aldehyde, Biochem. Biophys. Res. Comm. (1988) 153: 1201.), a cell penetrating "calpain" inhibitor (calpain is a cysteine protease); and DK-3 (Enzyme Systems Products, Dublin, Calif. CBZ-Phe-Ala-CHN$_2$) inhibits lysosomal protease activity. In addition, cells were incubated with Compound 16 which is a less potent MCP inhibitor compared to a particularly preferred compound of the invention, i.e. Compound 14. Cell lines expressing the indicated SOD-1 isoforms were incubated for 24 hours with the following protease inhibitors: Compound 14, 20 μM; Calpeptin, 10 μM; DK-3, 5 μM; Compound 16, 20 μM; or with DMSO as a negative control. After the 24 hours of incubation with the inhibitors, SOD-1 levels were measured by densitometric scanning of immunoblots. Levels of SOD-1 are expressed as units of induction relative to untreated samples, as above. Each data point is the average of results from three experiments.

Figure 7:
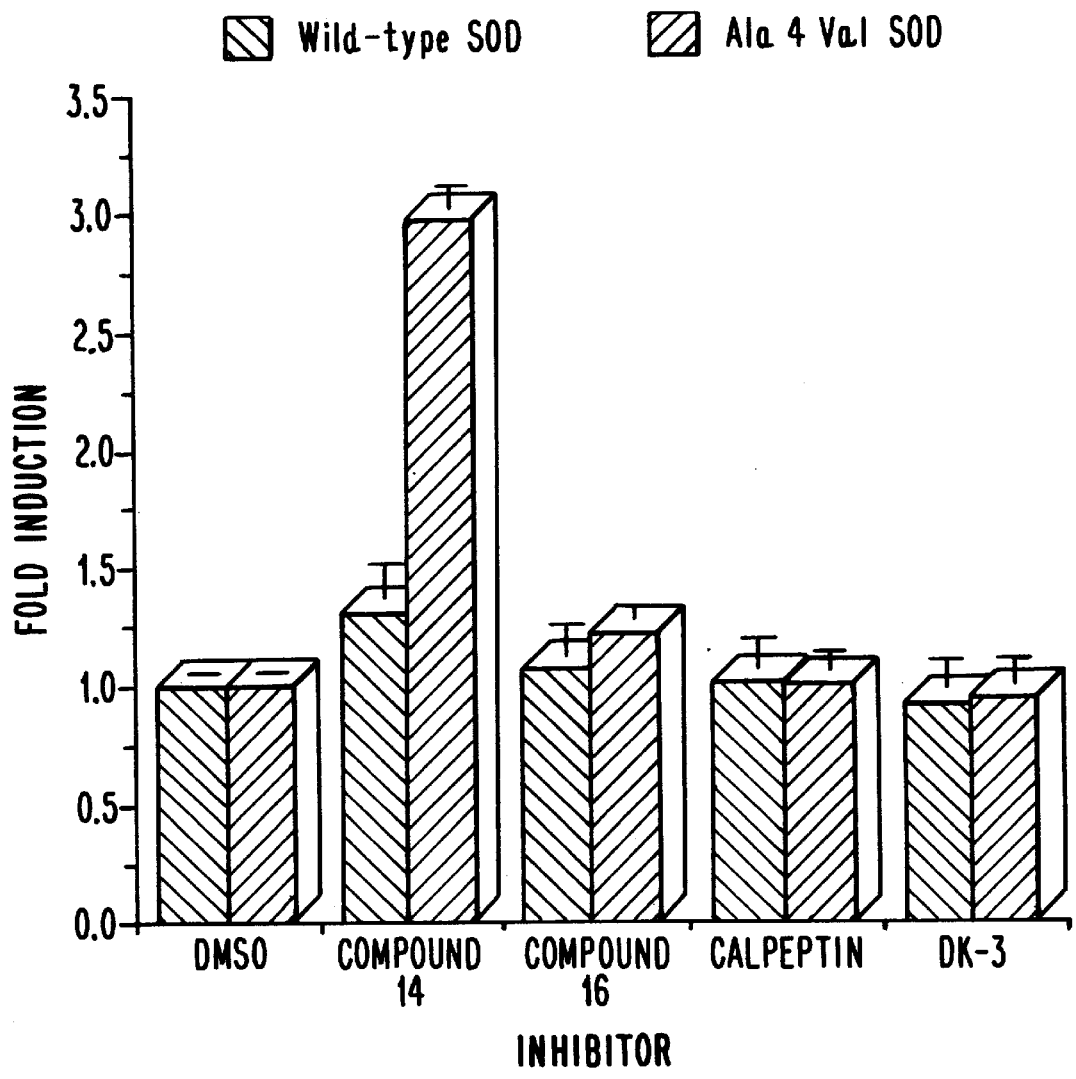
FIG. 7 shows that SOD-1 turnover is a function of MCP activity.

Results are presented in FIG. 7. It can be seen that the turnover of Ala$^4$→Val mutant SOD-1 is a function of MCP activity and only the specific inhibition of MCP by the preferred Compound 14 leads to a significant (three-fold) increase in the accumulation of SOD-1 protein. Incubation with the inhibitors of calpain or lysosomal proteases had no appreciable effect upon SOD-1 turnover. Further, Compound 14 treatment resulted in a slight increase in wild-type SOD-1 accumulation, a finding also observed previously in the dose response studies. Taken together, these studies demonstrate that MCP activity is critical for SOD-1 turnover in the transformed 293 cell lines, and that inhibition of MCP by Compound 14 leads to an elevation of SOD-1 protein within the cell.

Synthesis of Inhibitors

The following provides exemplary synthesis routes for the preparation of compounds of the present invention. Other synthesis protocols, as well as modifications of the following synthesis schemes will be readily apparent to those skilled in the art once armed with thee present disclosure.

The inhibitors of the invention incorporate amide bonds which may be introduced by well-known synthetic procedures using the solution-phase techniques described in The Peptides: Analysis, Synthesis, Biology, Volume I (1979), eds. Gross, et al, Academic Press and described in detail in Examples 8–11 below.

The inhibitors may be prepared by the separate synthesis and coupling of the fragments:

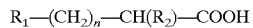

and

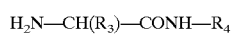

(Coupling Procedure I) as described in Examples 14–38.

Alternatively, they may be prepared by the separate synthesis and coupling of the fragments:

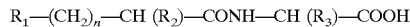

and

(Coupling Procedure II) as described in Examples 39–42 below.

When substituent Q contains an aldehyde group (i.e. when H$_2$N—R$_4$ is an aminoaldehyde derived from an aminoacid, e.g. H$_2$N—CH(CH$_2$R$_7$)—CHO) the requisite acetal-protected aminoaldehyde may be synthesized as described by Gacek, et al. Tetrahedron, 30, 4233 (1974) or by the procedures described in Example 12. After the coupling is completed (via Coupling Procedures I or II) the acetal protecting groups may be removed as described in Example 11 (Method E) to liberate the free aldehyde group.

When Q is a methylketone or a diazo-, bromo-, or chloromethyl ketone (i.e. when H$_2$N-R$_4$ is an alpha-amino-substituted methyl ketone or an alpha diazo-, bromo- or chloromethyl ketone derived from an amino acid), Coupling Procedure II is particularly convenient. The hydrochloride salt of the chloromethyl ketone may be purchased (Bachem Bioscience Inc., King of Prussia, Pa.) or can be prepared by conversion of the Boc-protected amino acid to a mixed carbonic anhydride followed by reaction with diazomethane to give the diazomethyl ketone. The bromo- and chloromethyl ketones are prepared by reaction of the diazomethyl ketone with hydrogen bromide or chloride as described by Kettner, et al. Arch. Biochem. Biophys. 162, 56(1974), Fittkau, J. Prakt. Chem. 315, 1037 (1973) or Zimmerman, et al. PCT WO 95/15749 published Jun. 15, 1995.

The corresponding methyl ketones may be prepared by hydrogenolysis of the chloromethyl ketones as described by Kettner, et al. U.S. Pat. No. 4,652,552.

When Q is an alpha-difluoromethyl ketone, the corresponding 1-amino-3,3-difluoro-2-propanol can be prepared and coupled by Coupling Procedure II, and the resulting difluoroalcohol oxidized to the difluoroketone by the procedure described by Trainor and Stein, U.S. Pat. No. 4,923,890.

When Q is a trifluoromethyl ketone (i.e. where $H_2N-R_4$ is an amino acid-derived trifluoromethyl ketone, e.g. $H_2N-CH(CH_2-R_7)-COCF_3$), the requisite ketone may be prepared as described by Imperiali and Abeles, *Biochemistry* 25, 3760 and supplementary pages (1986).

When Q is a monofluoromethyl ketonet (i.e. where $H_2N-R_4$ contains a fluoromethyl ketone group, e.g. $H_2N-CH(CH_2-R_7)-COCH_2F$) derived from an amino acid, the requisite ketone may be prepared by the procedure of Falmer in European Patent Application EP 442,754 using the Boc-protected amino acid and magnesium benzyl fluoromalonate. After removal of the Boc protecting groups, the amine can be coupled using Coupling Procedure II. Alternatively, the monofluoromethyl ketone can be prepared by oxidation of the corresponding alcohol as described in Example 42.

When Q is a boroamino acid derivative (i.e. $Q=-B(OH)_2$ or its cyclic ester), the cyclic ester is prepared essentially as described by Shenvi, U.S. Pat. No. 4,537,773, and after coupling by Coupling Procedure II, can optionally be converted to the free peptide boronic acid as described by Shenvi and Kettner in U.S. Pat. Nos. 4,499,082 and 5,187,157, and in *J. Biol. Chem.* 259, 15106 (1984).

When Q is an alpha-diketone or alp;ha-keto ester (i.e. $Q=-C(=O)C(=O)R_7$ or $-C(=O)CO_2R_7$) the requisite amino diketones or alpha-keto esters can be prepared as described by Angelastro, et al, *J. Med. Chem.* 33, 13 (1990) and references therein. The alpha-kimto esters may be hydrolyzed or amidated to produce the corresponding alpha-keto acids or amides. The alpha-keto amides may also be prepared from commercially available Boc-protected amino acids by a modification of the procedure of Harbeson, et al. *J. Med. Chem.* 37, 2918–2929 (1994). In this latter very useful procedure, the Boc-protected amino acid is sequentially converted to an N,O-dimethylhydroxylamide, an aldehyde, a cyanohydrin, an alpha-hydroxycarboxylate, and an alpha-hydroxycarboxamide:

$$R^1-COOH \rightarrow R^1-CON(CH_3)-OCH_3 \rightarrow R^1-CHO \rightarrow R^1-CH(OH)-CN \rightarrow R^1-CH(OH)-COOH \rightarrow R^1-CH(OH)-CONH-R$$

where $R^1=Boc-NH-CH(CH_2R_7)-$.

The Boc group is removed under acidic conditions and after neutralization, the free amino residue is coupled as in Coupling Procedure II to yield the alpha-hydroxycarboxamide which is then oxidized to give the alpha-ketocarboxamide inhibitor:

$$Boc-NH-CH(CH_2R_7)-CH(OH)-CONH-R_7 \rightarrow$$

$$H_2N-CH(CH_2R_7)-CH(OH)-CONH-R_7-(Coupling\ Procedure\ II) \rightarrow$$

$$R_1-(CH_2)_n-CHR_2-CONH-CH(R_3)-CONH-CH(CH_2R_7)-CH(OH)-CONHR_7 \rightarrow$$

$$R_1-(CH_2)_n-CH(R_2)-CONH-CH(R_3)-CONH-CH(CH_2R_7)-COCONH-R_7$$

EXAMPLE 7
Method A: Mixed anhydride method
Scheme

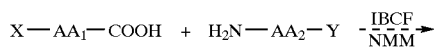

-continued

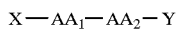

X=Fluorenylmethyloxycarbonyl (Fmoc)- or t-butyloxycarbonyl (Boc)- group; Y=Acetal or other protecting group for the amino aldehyde
AA$_1$=Amino acid
AA$_2$=Amino aldehyde N-methylmorpholine (NMM) (1 eq.) was added to a stirred solution of the protected amino acid in tetrahydrofuran (THF). The mixture was cooled to −15° C., treated with isobutyl chloroformate (IBCF) (1.1 eq.), and allowed to react for 10 min. Subsequently, the amino aldehyde component in the form of the free base was added followed by NMM (1.1 eq., 2.2 eq. if acid salt). Stirring proceeded for 30 min at −15° C., and then at room temperature for 3–4 h. The reaction mixture was dissolved in 150–200 mL of ethyl acetate (EtOAc). The resulting solution was successively washed with water, 5% sodium hydrogen carbonate (NaHCO$_3$), 2% aqueous citric acid and, finally, water. The organic layer was dried over anhydrous sodium sulfate (Na$_2$SO$_4$) or magnesium sulfate (MgSO$_4$), the solvent was removed under reduced pressure, and the product thus obtained was triturated with petroleum ether. The solid peptide thus obtained was filtered off, dried and characterized.

EXAMPLE 8
Method B: Fmoc-group deprotection procedure
Scheme

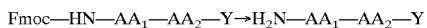

The Fmoc-protected peptide (0.2 to 1 mmol) in a mixture of 30% dimethylformamide (DMF) in ethyl acetate (EtOAc) was treated with a 50–60 fold excess of diethylamine (DEA) for 2 h at room temperature. The solvent was evaporated at reduced pressure at. 30° C., and petroleum ether was added to the residue. When a precipitate formed it was filtered and dried. In other cases, the resulting gum was repeatedly triturated with petroleum ether, and the gum was stored under vacuum.

EXAMPLE 9
Method C: Capping group or amino acid addition to the peptide
Scheme

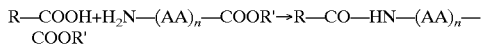

The capping group (as a free carboxylic acid) or protected amino acid (1 eq.), benzotriazol-1-yloxy-tris-(dimethyamino)-phosphonium hexafluorophosphate (BOP) (1.1 eq.) and 1-hydroxybenzotriazole (HOBt) (1 eq.) were dissolved in 5 mL of DMF followed by NMM (2.2 eq.). After 5 min, the deprotected basic component of the peptide or the carboxyl group protected amino acid was added, the pH was adjusted to 8 and the mixture was stirred for 3–4 h. It was then diluted with 150–300 mL of EtOAc and extracted consecutively with water, 2% NaHCO$_3$, water, 2% citric acid and water. The organic phase was dried and evaporated to dryness to yield a capped or N-protected peptide.

EXAMPLE 10
Method D: Carbobenzyloxy (CBZ-) group removal procedure

A solution of the CBZ-protected peptide or amino acid derivative (1 g) in ethyl acetate (15 mL) was mixed with 0.2 g of Pd/C on carbon (10% Pd on carbon containing 50% by weight of water) and hydrogenated for 4 h at 40 psi. The solution was filtered through Celitee (diatomaceous earth) and evaporated to dryness to yield the unprotected peptide or amino acid derivative.

EXAMPLE 11
Method E: Conversion of acetal to aldehyde

A solution of the peptide acetal (1. eq.) in 3 mL of THF was mixed with 3 mL of aqueous HCl (2M) and stirred for 0.5–2 h. The solvent was removed by evaporation and the final residue was diluted with water and lyophilized to give the peptide aldehyde.

EXAMPLE 12
Method F: Preparation of Leucinal diethylacetal

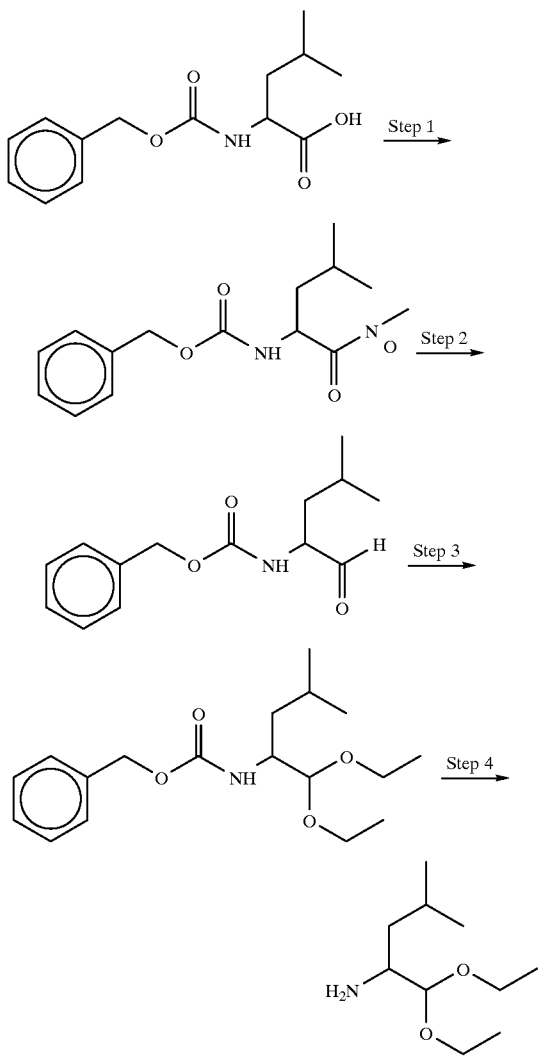

Step 1: NMM (10 mL) was added to a solution of CBZ-Leu-OH (25 g, 93 mmol) in 250 mL of THF. The solution was cooled to −15° C., treated with 13 mL of isobutyl chloroformate (IBCF), and allowed to react for 10 min. Subsequently, a suspension of N,O-dimethylhydroxylamine hydrochloride (9.36 g, 96 mmol) in 40 mL of DMF and 10 mL of NMM was added. After 4 h of stirring, the mixture was diluted with 400 mL of EtOAc and the solution was consecutively washed with water, 5% $NaHCO_3$ solution, water, 2% citric acid, and water. The organic layer was dried over $MgSO_4$ and evaporated to yield 19.0 g of a colorless oil.

Step 2: A solution of the oil (19 g) from step 1, in 200 mL of ether was cooled to −78° C., and 120 mL of a solution of lithium aluminium hydride ($LiAlH_4$) (1.0M) in ether was added dropwise over a period of 45 min. The solution was stirred for 30 min, and 200 mL of 1M potassium hydrogen sulfate ($KHSO_4$) was added dropwise under a nitrogen atmosphere. The organic layer was separated, washed with $KHSO_4$ (1M) solution, dried ($MgSO_4$) and evaporated to a colorless liquid (CBZ-Leu-H).

Step 3: 104 mL of triethyl orthoformate was added over a period of 30 min to a solution of CBZ-Leu-H (12 g) and p-toluenesulfonic acid (0.9 g) in 100 mL of anhydrous ethanol (EtOH). The mixture was stirred for 30 min, and then was evaporated and diluted with 500 mL of ether. The ether layer was washed consecutively with saturated solutions of $NaHCO_3$ and sodium chloride. The yellowish brown semisolid was recrystallized from cold hexane to yield off-white needles of CBZ-Leucinal diethylacetal. $^1$H NMR (300 MHz, $CDCl_3$) δ: 7.28(m, 5H), 5.03(s, 2H), 4.77(d, 1H), 4.27(d, 1H), 3.8(m, 1H), 3.63(m, 2H), 3.43(m, 2H), 1.6(dd, 2H), 1.30(m, 2H), 1.12(m, 6H), 0.83(d, 6H)

Step 4: The product (14.8 g) from step 3 was hydrogenated using method D, with 2.5 g of Pd/C to yield 4.09 g of leucinal diethylacetal as an oil. $^1$H NMR (300 MHz, $CDCl_3$) δ: 4.16(d, 1H), 3.70(m, 3H), 3.75(m, 2H), 2.87(m, 1H), 1.78(m, 1H), 1.33(m, 2H), 1.23(m, 6H), 0.935(dd, 6H)

EXAMPLE 13
Method G: Synthesis of P3 mimics (For nomenclature, see Schechter, I. and Burger, A. (1967) *Biochem. Biophys. Res. Commun.* 27: 157–162).

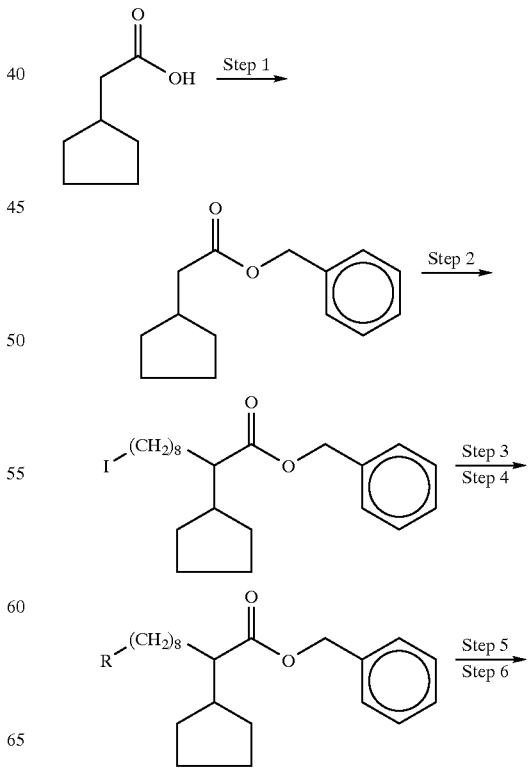

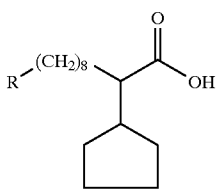

(Steps 3 and 5, R = ——CN; steps 4 and 6 R =

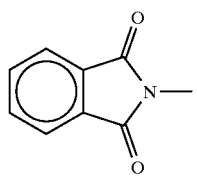

Step 1: Preparation of benzyl cyclopentaneacetate:

A mixture of cyclopentylacetic acid (10.02 g, 78.2 mmol), benzyl alcohol (8.45 g, 78.2 mmol) and p-toluenesulfonic acid monohydrate (1.48 g, 7.82 mmol) in benzene (60 mL) was refluxed using a Dean-Stark water separator for 2 h. After cooling, benzene was removed and the mixture was diluted with ether (50 mL) and washed successively with saturated NaHCO$_3$ solution, saturated brine solution, dried and evaporated to give the compound (15.40 g) as an oil; $^1$H NMR (300 MHz, CDCl$_3$) δ: 7.35(m, 5H), 5.10(s, 2H), 2.40(d, j=8 Hz, 2H), 2.26(m, 1H), 1.81(m, 2H), 1.6(m, 4H), 1.18(m, 2H).

Step 2: Preparation of benzyl 2-cyclopentyl-10-iododecanoate

To a cooled (–78° C.) solution of lithium diisopropylamide (20 mmol) in a mixture of THF (20 mL) and hexane (8 mL) (obtained in situ from the corresponding diisopropylamine and n-BuLi) was added slowly the compound obtained in step 1(3.96 g, 18 mmol) in anhyd. THF(10 mL). The mixture was stirred for 30 minutes and 1,8-diiodooctane (7.19g, 20 mmol) in hexamethylphosphoramide (3.50 g, 20 mmol), was added. The mixture was stirred at –78° C. for 30 minutes, slowly brought to 0° C. over a period of 2 h and quenched by the cautious addition of 50 mL of 12% aqueous sodium chloride solution. The mixture was extracted with ether, washed with brine, dried and the solvent was evaporated. The crude product was purified to an oil (3.23 g) by a flash chromatography over silica using hexane to 1% EtOAc in hexane as an eluant; $^1$H NMR (300 MHz, CDCl$_3$) δ: 7.35(m, 5H), 5.15(s, 2H), 3.20(t, 8 Hz, 2H), 2.20(m, 1H), 2.0(m, 1H), 1.2–1.8(m, 22H)

Step 3: Preparation of benzyl 10-cyano-2-cyclopentyldecanoate

A mixture of the iodoester from step 2, (3.99 g, 8.7 mmol) and sodium cyanide (0.47 g, 9.6 mmol) in 15 mL of anhyd. DMSO was heated at 70–75° C. for 30 min. After cooling, the reaction mixture was poured over ice (~40 g), extracted into ether and washed successively with water and saturated brine. The organic layer was concentrated to yield an oil (2.89 g). $^1$H NMR (300 MHz, CDCl$_3$). δ: 7.35 (m, 5H), 5.15 (s, 2H), 2.30(t, 8 Hz, 2H), 2.20(m, 1H), 2.00(m, 1H), 1.3–1.8 (m, 22H).

Step 4: Preparation of benzyl 10-N-phthalimido-2-cyclopentyldecanoate

A mixture of the compound from step 2(1.21 g, 2.6 mmol)and potassium phthalimide (0.536 g, 3 mmol) in 8 mL of DMF was heated at 70–750 for 30 min. After cooling, the reaction mixture was poured over ice (~40 g) and extracted into 60 mL of ether. The combined organic layer as washed with water and saturated brine and concentrated to a colorless oil (1.24 g). $^1$H NMR (300 MHz, CDCl$_3$) δ : 7.85(m, 2H), 7.70(m, 2H), 7.35(m, 5H), 5.10(s, 2H), 3.65(t, 8 Hz, 2H), 2.20(m, 1H), 2.00(m, 1H), 1.22–1.18(m, 22H).

Step 5: Preparation of 10-cyano-2-cyclopentyldecanoic acid

A mixture of the cyanoester from step 3 (2.89 g, 8 mmol) and 10%, Pd—C (0.6 g, DeGussa, H$_2$O content 50%) in anhyd MeOH (35 mL) was hydrogenated for 2 h (42–26 psi). The reaction mixture was filtered through a Celite® pad and concentrated to a colorless oil (2.02 g). $^1$H NMR (300 MHz, CDCl$_3$) δ 2.35(t, 8 Hz, 2H), 2.20 (m, 1H), 2.00 (m, 1H), 1.3–1.9(m, 22H).

Step 6: Preparation of 2-cyclopentyl-10-N-phthalimidodecanoic acid

Following the procedure of step 5, product (0.41 g) of step 4 was converted to the title compound (0.31 g). $^1$H NMR (300 MHz, CDCl$_3$) δ 7.85 (m, 2H), 7.70 (m, 2H), 3.70(t, 8 Hz, 2H), 2.15(m, 1H), 1.95(m, 1H), 1.10–1.85(m, 22H).

Step 7: Preparation of 10-trifluoromethanesulfonamido-2-cyclopentyl-decanoic acid benzyl ester

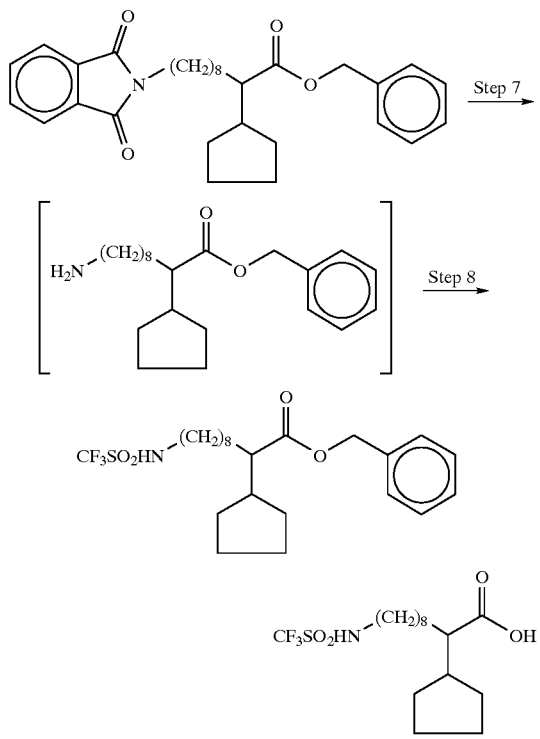

A mixture of the ester from step 4(0.874 g, 1.7 mmol) and hydrazine monohydrate (0.425 g, 0.41 mL, 8.5 mmol) in methanol (8 mL) was heated under reflux for 30 min, concentrated, and the residue was triturated with ether to give a white precipitate which was filtered off. The filtrate was concentrated to give an oil (0.540 g). The oil was dissolved in CH$_2$Cl$_2$ (8 mL) cooled to –10° C. and to it was added triethylamine (0.324 mL) followed by trifluoromethane sulfonylchloride (0.25 mL). The temperature was slowly brought to room temperature over a period of 1 h. The reaction mixture was then washed with water, 2% HCl, water and saturated brine. The organic layer was concentrated to an oil and was purified by flash chromatography over silica gel using 10% EtOAc in hexane as an eluant to yield 10-trifluoromethanesulfonamido-2-cyclopentyl-decanoic acid benzyl ester as an oil (0.25 g). $^1$H NMR (300 MHz, CDCl$_3$) δ 7.35(m, 5H), 5.15(s, broad, 1H), 5.10(s, 2H), 3.25(m, 1H), 2.20(m, 1H), 2.00(m, 1H), 1.10–1.7(m, 22H).

Step 8: Preparation of 2-cyclopentyl-10-trifluoromethanesulfonamido)-decanoic acid Following the same procedure as described in step 5, compound (0.25 g) obtained from step 7 was converted to the title compound (0.20 g) as an oil. $^1$H NMR (300 MHz, CDCl$_3$) δ 6.60–5.60 (b, 1H), 3.30 (d, 8 Hz, 2H), 2.15(m, 1H), 1.90 (m, 1H), 1.1–1.8 (m, 22H).

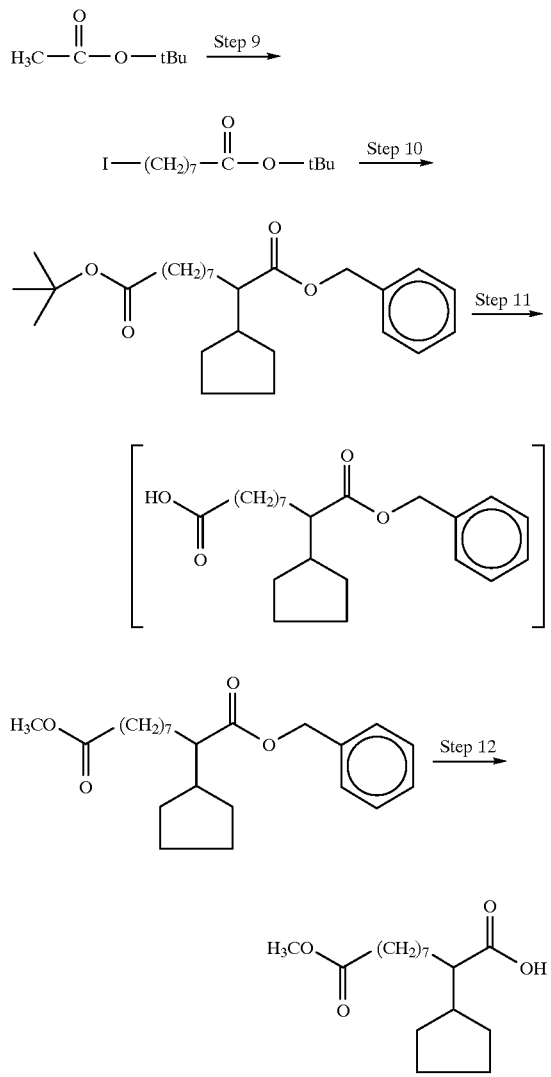

Step 9: Preparation of t-butyl 8-iodocaprylic acid

The title compound was synthesized following the procedure as described for the compound in step 2 from t-butyl acetate (1.16 g) and 1,6-diiodohexane (4.06 g) as an oil (2.13 g). $^1$H NMR (300 MHz, CDCl$_3$) δ 3.20(t, 8 Hz, 2H), 2.20(t, 8 Hz, 2H), 1.75–1.85(m, 2H), 1.55–1.65(m, 2H), 1.45(s, 9H), 1.25–1.43(m, 6H).

Step 10: Preparation of 2-cyclopentyldecan-1,10-dioic acid-1-benzyl-10-t-butyl ester Using the procedure as described in step 2, the ester (6.92 g) from step 1 and the iodoester (11.37 g) from step 9 were reacted to give the title compound (7.44 g) oil. $^1$H NMR (300 MHz, CDCl$_3$) δ 7.35 (m, 5H), 5.10 (s, 2H), 2.20(m, 3H), 2.00(m, 1H), 1.45 (s, 9H), 1.0–1.9 (m, 20H)

Step 11: Preparation of 2-cyclopentyldecan-1,10-dioic acid-1-benzyl-10-methyl ester A solution of the diester from step 10 (2.86 g, 7 mmol) in CH$_2$Cl$_2$(30 mL) and 10 mL of 90% TFA was stirred for 30 min. The product obtained after evaporation was dissolved in a mixture of CH$_2$Cl$_2$ (10 mL) and MeOH (6 mL). The solution was stirred at −20° C. and to it was slowly added thionyl chloride (6 mL) over a period of 2 h. The solvent was evaporated and the residue was dissolved in diethyl ether (20 mL). The organic layer was washed successively with saturated NaHCO$_3$ solution, water and brine, dried, evaporated and flash chromatographed on silica gel (eluant: 2% EtOAc-hexane) to furnish the product as an oil (2.05 g). $^1$H NMR (300 MHz, CDCl$_3$) δ 7.35 (m, 5H), 5.10(s, 2H), 3.65 (s, 3H), 2.30(t, 8 Hz, 2H), 2.20 (m, 1H), 02.00 (m, 1H), 1.10–1.90(m, 10H)

Step 12: Preparation of 2-cyclopentyldecan-1,10-dioic acid-10-methyl ester

Using the procedure as described in step 5, the compound (4.96 g) from step 11 was converted to the title compound (3.66 g) as an oil. $^1$H NMR (300 MHz, CDCl3) δ 3.65(s, 3H), 2.30(t, 8 Hz, 2H), 2.15(m, 1H), 2.00(m, 1H), 1.10–1.19 (m, 20H).

Step 13: Preparation of 6-cyanohexane-1-sulfinic acid sodium salt

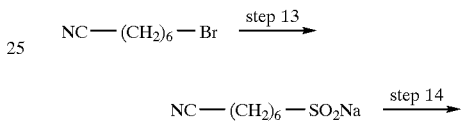

In a three necked flask, fitted with a water condenser, a mechanical stirrer and a dropping funnel a solution of 1-bromo-6-cyanohexane (8.04 g, 42.3 mmol) was placed in 75 mL of 95% EtOH. The mixture was heated to reflux and to it was slowly added a solution of sodium sulfite (8.00 g, 63.5 mmol) in 50 mL of H$_2$O over a period of 30 min. The mixture was heated for 2 h and then concentrated under reduced pressure. The residue was dissolved in 95% EtOH (200 ml), heated to boiling and filtered. The filtrate was concentrated and cooled in an ice bath. The precipitate was collected by filtration and dried to give 3.00 g of a white solid. The mother liquor on further concentration, produced another batch of 2.2 g of the product. $^1$H NMR (300 MHz, DMSO-d$_6$) δ 2.50 (t, j=8 Hz, 2H), 2.40(t, 8 Hz, 2H), 1.55(m, 4H), 1.3 (m, 4H).

Step 14: Preparation of 6-cyanohexane-1-sulfonyl chloride

A mixture of the product from step 13 (0.340 g, 1.6 mmol), thionyl chloride (0.95 g, 8 mmol) and a drop of DMF was heated at 75–80° C. for 30 min. After cooling, the solvent was removed and the residue was treated with ice-water (5 mL). The organic layer was extracted into 30 mL of ether and the combined organic layer was washed with 3% NaHCO$_3$ solution and water, dried (MgSO$_4$) and filtered. The filtrate was treated with active carbon (Darco), filtered and concentrated to give a colorless oil (0.240 g) which was used without further purification.

Examples 14–38 describe the syntheses of the MCP inhibitors listed in Table 5. The corresponding purification conditions are listed in Table 6.

TABLE 5

Multicatalytic Protease Inhibitors

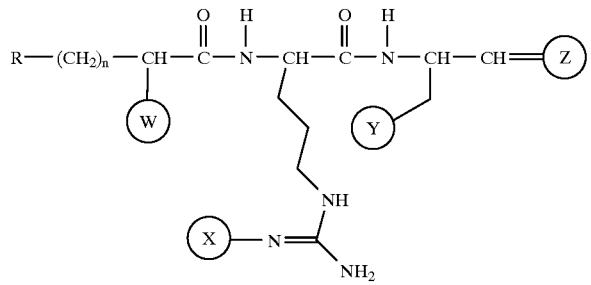

| Example No. | R | a | W | X | Y | Z | IC$_{50}$ nM |
|---|---|---|---|---|---|---|---|
| 14 | NC— | 8 | 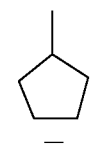 | NO$_2$ | (CH$_3$)$_2$CH— | O | 7/6 |
| 15 | NC— | 8 | " | PMC | (CH$_3$)$_2$CH— | O | 20 |
| 16 | NC— | 8 | " | NO$_2$ | (CH$_3$)$_2$CH— | N—NHCONH$_2$ | 100 |
| 17 | NC— | 8 | " | NO$_2$ | (CH$_3$)$_2$CH— | N—OH | ... |
| 18 | NC— | 8 | " | NO$_2$ | (CH$_3$)$_2$CH— | N—OCH$_3$ | 700 |
| 19 | NC— | 8 | " | NO$_2$ | (CH$_3$)$_2$CH— | N—O—CH$_2$C$_6$H$_5$ | ... |
| 20 | MeOOC— | 7 | " | PMC | (CH$_3$)$_2$CH— | O | 10 |
| 21 | MeOOC— | 7 | " | MTR | (CH$_3$)$_2$CH— | O | 30 |
| 22 | MeOOC— | 7 | " | PMC | CH$_3$—CH$_2$CH$_2$— | O | 110 |
| 23 | MeOOC— | 7 | " | NO$_2$ | (CH$_3$)$_2$CH— | O | 5 |
| 24 | C$_6$H$_4$(CO)$_2$N— | 8 | " | NO$_2$ | (CH$_3$)$_2$CH— | O | 2 |
| 25 | CF$_3$—SO$_2$NH— | 8 | " | NO$_2$ | (CH$_3$)$_2$CH— | O | 8/5 |
| 26 | MeOOC— | 6 | H | NO$_2$ | (CH$_3$)$_2$CH— | O | 40 |
| 27 | MeOOC— | 6 | H | NO$_2$ | C$_6$H$_5$ | O | 130 |
| 28 | MeOOC— | 6 | H | PMC | (CH$_3$)$_2$CH— | O | 20 |
| 29 | MeOOC— | 6 | H | PMC | (CH$_3$)$_2$CH— | O | >300 |
| 30 | MeOOC— | 6 | H | PMC | CH$_3$—CH$_2$CH$_2$— | O | >100 |
| 31 | MeOOC— | 6 | H | TOS | (CH$_3$)$_2$CH— | O | 75 |
| 32 | MeOOC— | 6 | H | MTR | (CH$_3$)$_2$CH— | N—NHCONH$_2$ | 220 |
| 33 | MeOOC— | 6 | H | MTR | (CH$_3$)$_2$CH— | N—NHCSNH$_2$ | 700 |
| 34 | MeOOC— | 6 | H | MTR | (CH$_3$)$_2$CH— | O | 80 |
| 35 | MeOOC— | 6 | H | MTS | (CH$_3$)$_2$CH— | O | 40 |

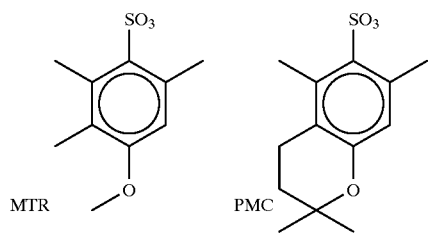

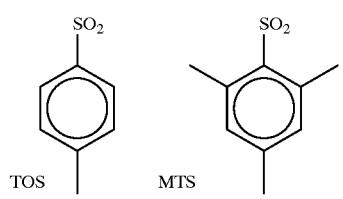

TABLE 5-continued

Multicatalytic Protease Inhibitors

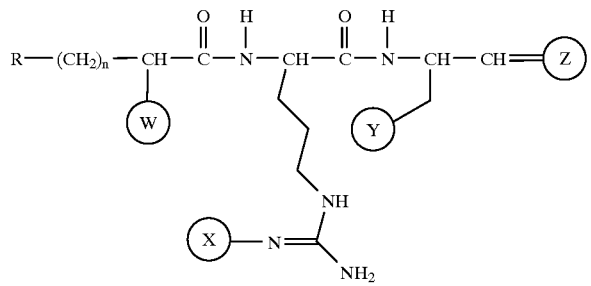

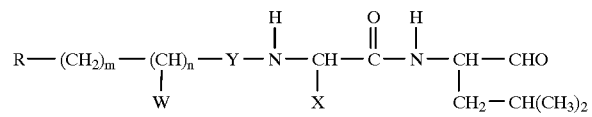

| Example No. | R | m | n | W | X | Y | IC$_{50}$ nm |
|---|---|---|---|---|---|---|---|
| 36 | NC— | 5 | 1 | H | PMC—NH—C(=NH)—NH—(CH$_2$)$_3$— | —SO$_2$— | >>100 |
| 37 | β-Naphthyl | 0 | 0 | — | O$_2$N—NH—C(=NH)—NH—(CH$_2$)$_3$— | —C(O)— | 250 |
| 38 | CBZ—NH— | 5 | 1 | H | O$_2$N—NH—C(=NH)—NH—(CH$_2$)$_3$— | —C(O)— | ... |

TABLE 6

| Example No. | COMPOUNDS | HPLC gradient (Ret. time of the peak collected) | Analyt. rt. time in min. | Mol. Wt | (M + H)$^+$ |
|---|---|---|---|---|---|
| 14 | 10-cyano-2-cyclopentyldecanoyl-N$^g$-nitro-L-arginyl-L-leucinal | 45–75% B (10.63) | 22.5 | 563.75 | 564 |
| 15 | 10-Cyano-2-cyclopentyl-decanoyl-N$^g$-(2,2,5,7,8-pentamethylchroman-6-sulfonyl)-L-arginyl-L-leucinal | 43–100% B (22.0) | 31.7 | 785.2 | 786 |
| 16 | 10-cyano-2-cyclopentyl-decanoyl-N$^g$-nitro-L-arginyl-L-leucinal semicarbazone | 30–35% B 60 min (A = 30.0, B = 32.0) | 22.2 22.7 | 621 | 621 |
| 17 | 10-cyano-2-cyclopentyl-decanoyl-N$^g$-nitro-L-arginyl-L-leucinal oxime | 45–65% B (12.3) | 24.8 | 578.7 | 579 |
| 18 | 10-cyano-2-cyclopentyl-decanoyl-N$^g$-nitro-L-arginyl-L-leucinal-O-methyloxime | 55–75% B (A = 8.9, B = 10.12) | 27.7 | 592.7 | 593 |
| 19 | 10-Cyano-2-cyclopentyl-decanoyl-N$^g$-nitro-L-arginyl-L-leucinal-O-benzyloxime | 65–75% B (A = 8.3, B = 9.5) | 31.3 | 668.7 | 669 |
| 20 | 9-Methoxycarbonyl-2-cyclopentyl-nonanoyl-N$^g$-(2,2,5,7,8-pentamethylchroman-6-sulfonyl)-L-arginyl-L-leucinal | 60–100% B (14.1) | 32.0 | 804.11 | 805 |
| 21 | 9-Methoxycarbonyl-2-cyclopentyl-nonanoyl-N$^g$-(4-methoxy-2,3,6-trimethyl-benzene-1-sulfonyl)-L-arginyl-L-leucinal | 40–60% B (29.9) | 28.9 | 749 | 750 |
| 22 | 9-Methoxycarbonyl-2-cyclopentyl-nonanoyl-N$^g$-(2,2,5,7,8-pentamethylchroman-6-sulfonyl)-L-arginyl-L-norleucinal | 60–70% B (18.8) | 32.2 | 804 | 804 |
| 23 | 9-Methoxycarbonyl-2-cyclopentyl-nonanoyl-N$^g$-nitro-L-arginyl-L-leucinal | 40–70% B (13.98) | 23.6 | 582.34 | 583 |
| 24 | 2-cyclopentyl-10-N-phthalimido-decanoyl-N$^g$-nitro-L-arginyl-L-leucinal | 50–80% B (12.66) | 27.89 | 683.86 | 684 |
| 25 | 10-(trifluoromethanesulfonyl)amino-2-cyclopentyl-decanoyl-N$^g$-nitro-L-arginyl-L-leucinal | 50–70% B (A = 12.1, B = 12.9) | 27.20 27.46 | 686.02 | 686 |
| 26 | Monomethylazelayl-N$^g$-nitro-L-arginyl-L-leucinal | 30–100% B (8.14) | 17.06 | 501 | 501 |

TABLE 6-continued

| Example No. | COMPOUNDS | HPLC gradient (Ret. time of the peak collected) | Analyt. rt. time in min. | Mol. Wt | (M + H)+ |
|---|---|---|---|---|---|
| 27 | Monomethylazelayl-N$^g$-nitro-L-arginyl-L-phenylalaninal | 10–100% B (16.9) | 17.3 | 534 | 535 |
| 28 | Monomethylazelayl-N$^g$-(2,2,5,7,8-pentamethylchroman-6-sulfonyl)-L-arginyl-L-leucinal | 10–100% B (11.7) | 26.5 | 722 | 723 |
| 29 | Monomethylazelayl-N$^g$-(2,2,5,7,8-pentamethylchroman-6-sulfonyl)-D-arginyl-L-leucinal | 40–70% B (16.2) | 26.3 | 722 | 723 |
| 30 | Monomethylazelayl-N$^g$-(2,2,5,7,8-pentamethylchroman-6-sulfonyl)-L-arginyl-L-norleucinal | 50–60% B (14.0) | 26.2 | 722 | 723 |
| 31 | Monomethylazelayl-N$^g$-(p-toluenesulfonyl)-L-arginyl-L-leucinal | 40–50% B (19.6) | 21.3 | 610 | 610 |
| 32 | Monomethylazelayl-N$^g$-(4-methoxy,2,3,6-trimethyl-1-sulfonyl)-L-arginyl-L-leucinal semicarbazone | — | 13.2 | 724 | 725 |
| 33 | Monomethylazelayl-N$^g$-(4-methoxy,2,3,6-trimethyl-1-sulfonyl)-L-arginyl-L-leucinal thiosemicarbazone | — | 23.4 | 741 | 741 |
| 34 | Monomethylazelayl-N$^g$-(4-methoxy,2,3,6-trimethylbenzene-1-sulfonyl)-L-arginyl-L-leucinal | 40–44% B (60 min) (16.9) | 23.3 | 668 | 669 |
| 35 | Methoxyazelaoyl-N$^g$-(2,4,6-trimethylbenzene-1-sulfonyl)-L-arginyl-L-leucinal | 40–60% B (14.1) | 32.0 | 638 | 638 |
| 36 | 6-Cyano-hexane-1-sulfonyl-N$^g$-(2,2,5,7,8-pentamethylchroman-6-sulfonyl)-L-arginyl-L-leucinal | 45–75% B (13.74) | 24.94 | 710.9 | 711 |
| 37 | 2-Naphthoyl-N$^g$-nitro-L-arginyl-L-leucinal | 35–55% B (9.16) | 18.10 | 470.51 | 471 |
| 38 | CBZ-7-aminoheptanoyl-N$^g$-nitro-L-arginyl-L-leucinal | 30–60% B (A = 13.3, B = 13.9) | 19.1 | 577 | 578 |

HPLC conditions:
Solvent A: Water containing 0.1% TFA
Solvent B: Acetonitrile containing 0.1% TFA
Detection: 215 nm.
HPLC gradients are in 40 min. unless noted otherwise.
Column Type:
Zorbax R$_x$—C$_8$
Dimension 4.6 mm × 250 mm
Pore Size 80 Angstroms
Particle Size 5 micron

EXAMPLE 14

10-cyano-2-cyclopentyldecanoyl-N$^g$-nitro-L-arginyl-L-leucinal

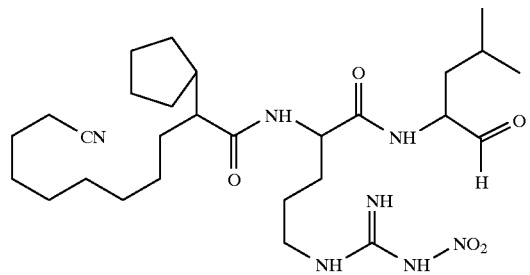

Step 1: Fluorenylmethyloxycarbonyl-N$^g$-nitro-L-arginyl-L-leucinal diethylacetal.

Fmoc-Arg(NO$_2$)-OH (4.41g, 10 mmol) was coupled with Leu-acetal (1.89g, 10 mmol) according to method A (Example 7), using 1.29 mL of IBCF, 2.2 mL of NMM and 10 mL of THF (in the place of DMF as in method A of Example 7). The crude peptide was obtained as amorphous solid. $^1$H NMR (300 MHz, CDCl$_3$) δ 7.75 (d, 2H), 7.55 (d, 2H), 7.4 (m, 2H), 7.29(m, 2H), 6.21(d, 1H), 5.91(d, 1H), 4.30(m, 5H), 3.66(m, 3H), 3.63(d, 2H), 3.32(m, 2H),1.72(m, 4H), 1.29(m, 2H), 1.17(b, 6H), 0.89 (m, 6H).

Step 2: N$^g$-nitro-L-arginyl-L-leucinal diethylacetal

The Fmoc group was removed from 3.5 g of the product from step 1 using deprotection method B (Example 8). The free base (2.5 g) was obtained as semisolid. $^1$H NMR (300 MHz, DMSO-d$_6$) δ 8.6 (b, 1H), 7.61(d, 1H), 4.27 (d, 1H), 3.90(m, 1H), 3.59(m, 1H), 3.45(m, 4H), 3.14(m,2H), 1.54 (m, 4H), 1.33(m, 3H), 1.10(tt, 6H), 0.83(dd, 6H).

Step 3: 10-cyano-2-cyclopentyl-decanoyl-N$^g$-nitro-L-arginyl-L-leucinal diethylacetal.

According to method C (Example 9), 10-cyano-2-cyclopentyl-decanoic acid (2 g, 7.5 mmol) from method G, in 16 mL of DMF was treated with product of Step 2 (2.15 g, 5 mmol) using BOP (3.34 g, 7.5 mmol) and HOBt (1.01 g, 7.5 mmol) to yield the crude peptide (3.85 g) as a pale yellow solid. $^1$H NMR (300 MHz, DMSO-d6) δ 8.31 (bd, 1H), 8.0 (bd, 1H), 7.83 (d, 1H), 4.34(m, 1H), 4.24(d, 1H), 3.91(m, 1H), 3.56(m, 4H), 3.43(m, 2H), 3.16(m, 2H), 2.47(t, 3H), 2.03(m, 1H), 1.76(m, 2H), 1.15–2.0(m, 25H), 1.07(m, 6H), 0.81(d, 6H)

Step 4: A solution of the product of step 3 (0.2 g) in 10 mL of acetonitrile (ACN) containing 30% TFA was stirred for 1 h, and the solvent was evaporated and Compound 14 was precipitated using diethyl ether. The HPLC purification conditions are given in Table 6. $^1$H NMR(300 MHz, DMSO-d$_6$) δ9.38(s, 1H), 8.56(b, 1H), 8.3(d, 1H), 7.99(dd, 1H), 4.38(m, 1H),4.17(m, 1H), 3.37(m, 4H), 3.17(m, 2H), 2.26(t, 3H), 1.0–2.0(m, 27H), 0.86(dd, 6H).

EXAMPLE 15

10-Cyano-2-cyclopentyl-decanoyl-N$^g$-(2,2,5,7,8-pentamethylchroman-6-sulfonyl)-L-arginyl-L-leucinal

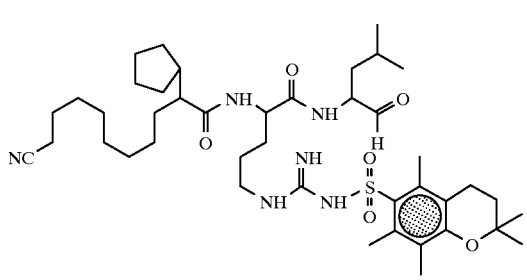

Step 1: 10-Cyano-2-cyclopentyl-decanoyl-N$^g$-(2,2,5,7,8-pentamethylchroman-6-sulfonyl)-L-arginyl-L-leucinal diethylacetal.

Following method C (Example 9), 10-cyano-2-cyclopentyl-decanoic acid (2 mmol, from step 5 in method G of Example 13) was coupled with N$^g$-(2,2,5,7,8-pentamethylchroman-6-sulfonyl)-L-arginyl-L-leucinal diethylacetal (1.8 mmol, from Step 2 in Compound 14) to obtain the compound as solid.

Step 2: 10-Cyano-2-cyclopentyl-decanoyl-N$^g$-(2,2,5,7,8-pentamethylchroman-6-sulfonyl)-L-arginyl-L-leucinal.

Following Method E (Example 11), the product from step 1(0.3 g) was converted to Compound 15 (0.2 g) and purified by HPLC. $^1$H NMR(300 MHz, DMSO-d6) δ 9.38(s, 1H), 8.23(d, 1H), 7.8(s, 1H), 7.72(d, 1H), 7.49(t, 1H), 7.48(s, 1H), 4.34(m, 1H), 4.14(m, 1H),3.05 (m, 2H), 2.60(t, 2H), 2.50(s, 3H), 2.46(s, 3H), 2.25(m, 4H), 2.00(s, 3H), 1.74(t, 2H), 1.6–1.0 (m, 25H), 1.13(s, 6H), 0.82 (dd, 6H)

EXAMPLE 16

10-cyano-2-cyclopentyl-decanoyl-N g-nitro-L-arginyl-L-leucinal semicarbazone

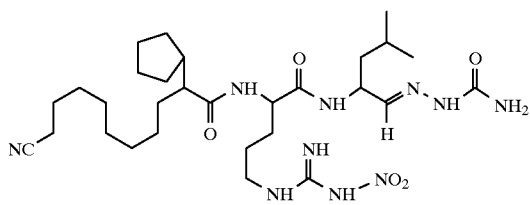

Semicarbazide hydrochloride (0.20 mmol), sodium acetate (0.3 mmol) and water (0.5 mL) were added to a solution of Compound 14 (0.050 g, 0.089 mmol) in 4.5 mL of ethanol and stirred overnight at room temperature. Solvent was removed and the resulting Compound 16 was purified by HPLC as indicated in Table 6. $^1$H NMR (300 MHz, DMSO-d$_6$) δ 9.91(s, 1H), 8.51(s, 2H) 8.04(d, 1H), 7.95(d, 1H)7.40(s, 1H), 7.09(d, 1H),6.29(s, 2H),4.44(m, 1H), 4.33(m, 1H), 3.16(s, 2H), 2.08–1.00 (m, 33H), 0.87(dd, 6H).

EXAMPLE 17

10-cyano-2-cyclopentyl-decanoyl-N$^g$-nitro-L-arginyl-L-leucinal oxime

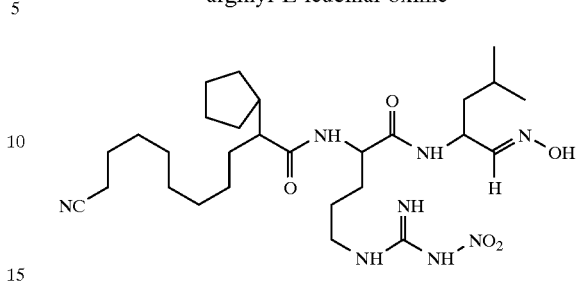

Hydroxylamine hydrochloride (0.037 g, 0.534 mmol) was added to a solution of the product of step 4 in Example 14 (0.05 g, 0.089 mmol) in pyridine (0.175 g, 2.2 mmol) at room temperature and then at 80° C. for 30 minutes. The product was isolated by HPLC as indicated in Table 6.

EXAMPLE 18

10-cyano-2-cyclopentyl-decanoyl-N$^g$-nitro-L-arginyl-L-leucinal-O-methyloxime

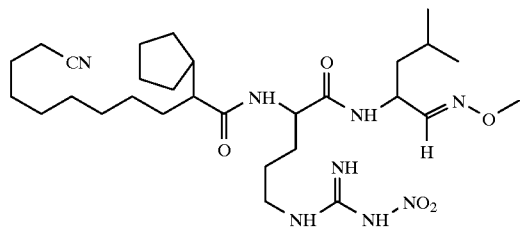

Following the procedure of Example 17, Compound 18 was prepared using O-methylhydroxylamine hydrochloride (0.031 g, 0.38 mmol) and isolated as a mixture of two peaks by HPLC as indicated in Table 6.

EXAMPLE 19

10-Cyano-2-cyclopentyl-decanoyl-N$^g$-nitro-L-arginyl-L-leucinal-O-benzyloxime

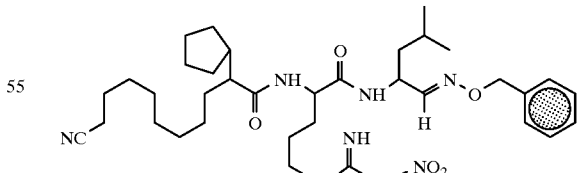

Following the procedure as in the preparation of Example 17, Compound 19 was made using Compound 14 (0.05 g, 0.089 mmol), O-benzyl hydroxylamine hydrochloride (0.043 g, 0.267 mmol) and pyridine (0.092 mL, 1.14 mmol). The compound was separated as two peaks in HPLC purifications.

EXAMPLE 20

9-Methoxycarbonyl-2-cyclopentyl-nonanoyl-N$^g$-(2,2,5,7,8-pentamethylchroman-6-sulfonyl)-L-arginyl-L-leucinal

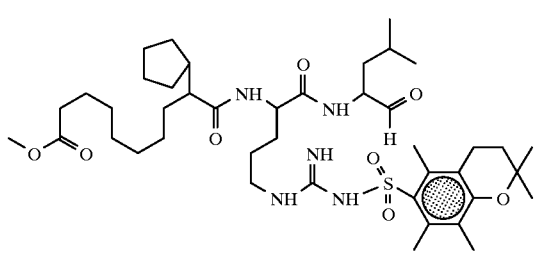

Step 1: Fmoc-N$^g$-(2,2,5,7,8-pentamethylchroman-6-sulfonyl)-L-argininyl-L-leucinal diethylacetal.

Following method C (Example 9), Fmoc-N$^g$-(2,2,5,7,8-pentamethylchroman-6-sulfonyl)-L-arginine (3.31 g, 5 mmol) was coupled with L-leucinal diethylacetal (0.85 g, from method F, Example 12) using BOP (2.21 g, 5 mmol), HOBt (0.67 g, 5 mmol) and NMM (0.7 mL) in 12 mL of DMF to yield the dipeptide acetal (3.24 g). $^1$H NMR (300 MHz, CDCl$_3$) δ 7.89(s, 1H), 7.78 (d, 2H), 7.6 (d, 2H),7.4(t, 2H), 7.31(t, 3H), 6.4(d, 2H),5.92(d, 1H), 4.58(m, 1H), 4.43(m, 1H), 4.35(m, 3H), 3.69(m, 2H), 3.53(m, 2H), 3.30 (m, 2H), 2.6(t, 2H), 2.58(s, 6H), 2.12(s, 3H), 1.80(tt, 2H), 1.64(m, 3H), 1.32(m, 10H), 1.18(q, 6H), 0.89(t, 6H).

Step 2: N$^g$-(2,2,5,7,8-pentamethylchroman-6-sulfonyl)-L-arginyl-L-leucinal.

Following method B (Example 8), the Fmoc group was removed from the product (1.6 g) from step 1, to yield a semi-solid (1.3 g). $^1$H NMR (300 MHz, DMSO-d$_6$) δ 7.6(d, 1H), 6.76(b, 1H), 6.46(b, 1H), 4.27(d, 1H), 3.9(m, 1H,), 3.58(m, 1H), 3.44(m, 4H), 3.11(t, 1H), 3.01(m, 2H), 2.58(t, 2H), 2.47(s, 6H), 2.03(s, 3H), 1.77(t, 2H), 1.5(m, 5H), 1.26(s, 6H),1.09(m, 6H), 0.83(dd, 6H)

Step 3: 9-Methoxycarbonyl-2-cyclopentyl-nonanoyl-N$^g$-(2,2,5,7,8-pentamethylchroman-6-sulfonyl)-L-arginyl-L-leucinal diethylacetal.

Following method C (Example 9), 9-methyloxycarbonyl-2-cyclopentyl-nonanoic acid (0.56 g) was coupled with N$^g$-(2,2,5,7,8-pentamethylchroman-6-sulfonyl)-L-arginyl-L-leucinal diethylacetal (0.7 g, 1.1 mmol) using BOP (0.66 g, 1.5 mmol), HOBt (0.202 g, 1.5 mmol) and NMM (2.2 mL, 2 mmol) in 5 mL of DMF to get the product (1.8 g) as solid. $^1$H NMR(300 MHz, MSO-d6) δ: 7.5–8.0(m, 2H), 6.66(m, 1H), 6.4(m, 1H), 4.32(m, 1H), 4.24(d, 1H), 3.93(m, 1H), 3.57(m, 6H), 3.44(m, 4H), 3.04(m, 2H), 2.59(t, 2H), 2.48(s, 6H), 2.28(m, 3H), 2.03(s, 3H), 1.77(t, 2H), 1.48(m, 22H), 1.26(s, 6H), 1.1(tt, 9H), 0.81(dd, 6H).

Step 4: 9-Methoxycarbonyl-2-cyclopentyl-nonanoyl-Ng-(2,2,5,7,8-pentamethylchroman-6-sulfonyl)-L-arginyl-L-leucinal.

According to the method E (Example 11), the product (0.2 g) from step 1 was converted to Compound 20 and purified by HPLC directly. $^1$H NMR(300 MHz, DMSO-d$_6$) δ 9.37(s, 1H), 8.2–7.4(m, 2H), 6.69(drm, 1H), 6.4(brm, 1H), 4.3(m, 2H), 3.58(s, 3H), 3.03 (m, 2H), 2.60(t, 2H), 2.48(s, 6H), 2.26(m, 4H), 2.03(s, 3H), 1.77(t, 2H), 1.47(brm, 28H), 1.24(s, 3H), 0.80 (dd, 6H).

EXAMPLE 21

9-Methoxycarbonyl-2-cyclopentyl-nonanoyl-N$^g$-(4-methoxy-2,3,6-trimethyl-benzene-1-sulfonyl)-L-arginyl-L-leucinal

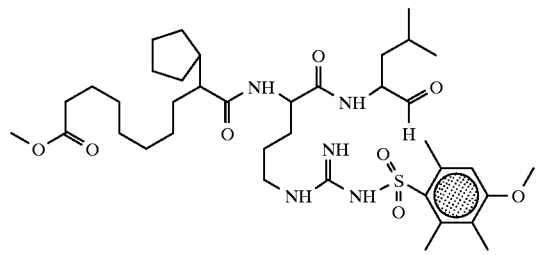

Step 1: 9-Methoxycarbonyl-2-cyclopentyl-nonanoyl-N$^g$-(4-methoxy-2,3,6-trimethylbenzene-1-sulfonyl)-L-arginyl-L-leucinal diethylacetal.

Following method C (Example 9), 9-Methoxycarbonyl-2-cyclopentyl-nonanoic acid (1.2 mmol, from step 12 in method G) was coupled with N$^g$-(4-methoxy-2,3,6-trimethylbenzene-1-sulfonyl)-L-arginyl-L-leucinal diethylacetal (1.0 mmol) to yield the peptide as solid.

Step 2: Following method E (Example 11), the acetal from step 1 was converted to Compound 21 and purified by HPLC. $^1$H (300 MHz, CDCl$_3$/DMSO-d$_6$) δ 9.42(s, 1H), 8.25(d, 1H), 7.92(d, 1H), 7.84(s, 1H), 6.4(m, 2H), 4.40(m, 1H), 4.20(m, 1H), 3.80(s, 3H), 3.57(s, 3H), 3.26(m, 2H), 2.64(s, 3H), 2.55(s, 3H), 2.36(m, 2H), 2.07(s, 3H), 1.8–1.0 (m, 30H), 0.87(dd, 6H)

EXAMPLE 22

9-Methoxycarbonyl-2-cyclopentyl-nonanoyl-N$^g$-(2,2,5,7,8-pentamethylchroman-6-sulfonyl)-L-arginyl-L-norleucinal

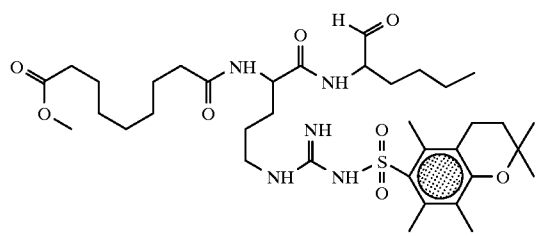

Step 1: 9-Methoxycarbonyl-2-cyclopentyl-nonainoyl-N$^g$-(2,2,5,7,8-pentamethylchroman-6-sulfonyl)-L-arginyl-L-norleucinal diethylacetal.

Using Method C (Example 9), 9-methoxycarbonyl-2-cyclopentyl-nonanoic acid (1 mmol) was coupled with N$^g$-(2,2,5,7,8-pentamethylchroman-6-sulfonyl)-L-arginyl-L-norleucinal diethylacetal (0.69 mmol, obtained from step 1 in Example 30 following method B) using BOP (1 mmol), HOBt (1 mmol) and NMM (2.5 mmol) in 5 mL of DMF. The reaction mixture was stirred for 4.5 hours and the peptide was isolated (0.37 g, 0.42 mmol).

Step 2: 9-Methoxycarbonyl-2-cyclopentyl-nonanoyl-N$^g$-(2,2,5,7,8,-pentamethylchroman-6-sulfonyl)-L-arginyl-L-norleucinal.

According to Method E (Example 11), the product (0.37 g, 0.42 mmol) from step 1 was converted to Compound 22 (0.33 g) and purified by HPLC. $^1$H NMR(300 MHz, DMSO-d6) δ: 9.29(s, 1H), 7.79(d, 1H), 7.89(d, 1H), 7.31(t, 1H), 7.26(s, 2H), 4.17(m, 1H), 3.94 (m, 1H), 3.49(s, 3H), 2.94 (m, 2H), 2.74(t, 2H), 2.51(t, 2H), 2.37(s, 6H), 2.20(m, 4H), 1.94(s, 3H), 1.14(s, 6H), 1.0–1.8 (m, 3H), 0.74 (t, 3H).

EXAMPLE 23

9-Methoxycarbonyl-2-cyclopentyl-nonanoyl-N$^g$-nitro-L-arginyl-L-leucinal

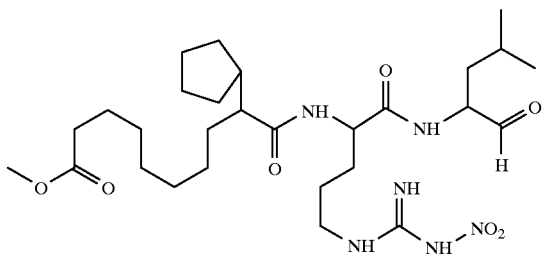

Step 1: 9-Methoxycarbonyl-2-cyclopentyl-nonanoyl-N$^g$-nitro-L-arginyl-L-leucinal diethylacetal.

Following Method C (Example 9), 9-methoxycarbonyl-2-cyclopentyl-nonanoic acid (0.66 g, 0.33 mmol) was coupled with the product from step 2 in Example 14 (0.109 g, 0.28 mmol) using BOP (0.146 g, 0.33 mmol), HOBt (0.0449 g, 0.33 mmol) and NMM (0.105, 0.95 mmol) in 7 mL of DMF to yield the title compound of Step 1 (0.124 g). $^1$H NMR(300 MHz, CDCl3 δ: 8.31(m, 2H), 6.69(br d, 1H), 6.15(br d, 1H), 4.5(m, 1H), 4.33(m, 1H), 4.18(m, 1H), 3.67(s, 3H), 3.53(m, 4H), 3.32(m, 2H), 2.68(m, 2H), 2.29(t, 3H), 2.0–1.0(b m, 34H), 0.90(dd, 6H).

Step 2: Following method E (Example 11), the peptide (from step 1, 0.124 g) was converted to Compound 23 (0.106 g). $^1$H NMR (300 MHz, DMSO-d$_6$). δ: 9.39(s, 1H), 8.54(m, 1H), 8.31(d, 1H), 7.99(br d,2H), 4.36(m, 1H), 4.15(m, 1H), 3.33(s, 3H), 3.16(m, 2H), 2.27(t, 2H), 2.03(m, 2H), 1.0–1.7 (m, 28H), 0.83(dd, 6H).

EXAMPLE 24

2-cyclopentyl-10-N-phthalimido-decanoyl-N$^g$-nitro-L-arginyl-L-leucinal

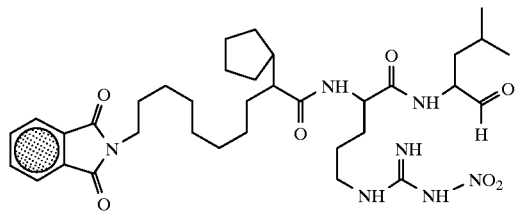

Step 1: 2-cyclopentyl-10-N-phthalimido-decanoyl-N$^g$-nitro-L-arginyl-L-leucinal diethylacetal.

Following Method C (Example 9), the product (0.25 g, 0.65 mmol) from step 6 in Method G (Example 13) was coupled to the product from step 2 in Example 14 (0.195 g, 0.5 mmol) using BOP (0.288 g, 0.65 mmol), HOBt (0.088 g, 0.65 mmol) and NMM (0.130 mL, 0.130 mmol) in 5 mL of DMF to obtain the title compound (0.557 g) as a solid. $^1$H NMR (300 MHz, DMSO-d6) δ: 8.57(br m, 1H), 7.91 (d, 1H), 7.85 (br d, 4H), 7.55 (d, 1H), 4.32 (m, 1H), 4.23 (dd, 1H), 3.90(m, 1H), 3.55 (t, 3H), 3.43 (m, 4H), 3.14(m, 2H), 2.0 (br m, 1H), 1.74 (br m, 2H), 2.0–1.15 (2 br m, 28H), 1.09(tt, 6H), 0.79 (dd, 6H).

Step 2: 2-cyclopentyl-10-N-phthalimido-decanoyl-N$^g$-nitro-arginyl-L-leucinal.

Using method E (Example 11), the product of step 1(0.45 g) was converted to Compound 24 (0.32 g). $^1$H NMR (300 MHz, DMSO-d$_6$) δ 9.38 (s, 1H), 8.31 (d, 1H), 8.00 (d, 1H), 7.85 (m, 4H), 4.38 (m, 1H), 4.15 (1, 1H), 3.57(tt, 3H), 3.15 (m, 2H), 2.00 (m, 1H), 1.9–1.0(br m, 30H), 0.86 (dd, 6H).

EXAMPLE 25

10-(trifluoromethanesulfonyl)amino-2-cyclopentyl-decanoyl-N$^g$-nitro-L-arginyl-L-leucinal

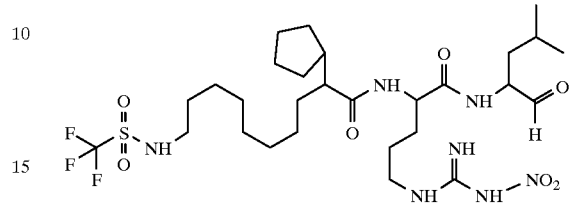

Step 1: (Trifluoromethanesulfonyl)10-amino-2-cyclopentyl-decanoyl-N$^g$-nitro-L-arginyl-L-leucinal diethylacetal.

Using Method C (Example 9), 10-(trifluoromethanesulfonyl)-amino-2-cyclopentyl-decanoic acid (0.199 g, 0.51 mmol) was coupled to the product from step 2 in Example 14 (0.175 g, 0.45 mmol) using BOP (0.22 g, 0.51 mmol), HOBt (0.069 g, 0.51 mmol) and NMM (0.052 mL, 0.47 mmol) in 5mL of DMF. The acetal was obtained as a solid (0.42 g). $^1$H NMR (300 MHz, CDCl$_3$) δ: 6.06(br m, 1H), 5.81(m, 1H), 4.53(m, 1H), 4.32(d, 1H), 4.13(m, 1H), 3.73(q, 4H), 3.53(m, 2H), 3.30(q, 3H), 2.0–1.0(2 br m, 36H), 0.9(dd, 6H).

Step 2: 10-(trifluoromethanesulfonyl)amino-2-cyclopentyl-decanoyl-N$^g$-nitro-L-arginyl-L-leucinal.

Following Method E (Example 11), the product from step 1 (0.35 g) was converted to Compound 25 (0.17 g). $^1$H NMR (300 MHz, DMSO-d$_6$) δ: 9.27(s, 1H), 8.46(br m, 1H), 4.30(m, 1H), 3.87(m, 1H), 3.09(m, 5H), 2.8–1.0(2 br m, 30H), 0.78(dd, 6H).

EXAMPLE 26

Monomethylazelayl-N$^g$-nitro-L-arginyl-L-leucinal

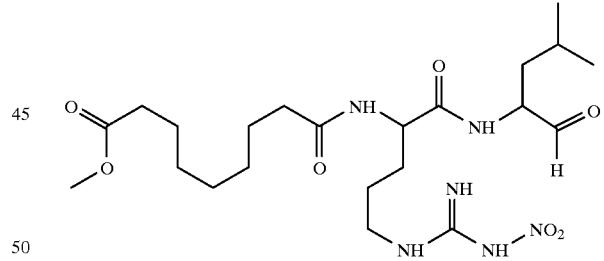

Step 1: Monomethylazelayl-N$^g$-nitro-L-arginyl-L-leucinal diethylacetal:

Following Method C (Example 9), the title compound was made using azelaic acid monomethyl ester (0.708 g, 3.5 mmol), BOP (1.55 g, 3.5 mmol), HOBt (0.47 g, 3.5 mmol), NMM (0.38 mL, 3.5 mmol), N$^g$-nitro-L-arginyl-L-leucinal diethylacetal (obtained from step 2 in Example 14 following method B, Example B) (1.306 g, 3.5 mmol) in 12 mL of DMF. The peptide was obtained as an amorphous solid (2.17 g). $^1$H NMR (300 MHz, CDCl$_3$) δ: 6.58(d, 1H), 6.04(d, 1H), 4.47(m, 1H), 4.30(d, 1H), 4.17(m, 1H), 3.67(s, 3H), 3.53(m, 2H), 3.2–3.4(t, d, 2H), 2.3(m, 3H), 2.2 (t, 1H), 1.83(m, 1H), 1.2–1.8(m, 24H), 1.2(m,3H), 0.9(d, 3H).

Step 2: Monomethylazelayl-N$^g$-nitro-L-arginyl-L-leucinal:

Using the Method E (Example 11), the peptide acetal (from step 1) (250 mg) was converted to Compound 26 (0.22 g). ¹H NMR (300 MHz, DMSO-d₆) δ: 9.38(s, 1H), 7.73(d, 1H), 4.30(m, 1H), 4.09(m, 1H),3.57(s, 3H), 3.15(m, 2H), 3.01(q, 1H), 2.75(m, 1H), 2.24(m, 7H),1.50(m, 12H), 1.24 (b, 14H), 0.86(m, 6H)

EXAMPLE 27

Monomethylazelayl-N$^g$-nitro-L-arginyl-L-phenylalaninal

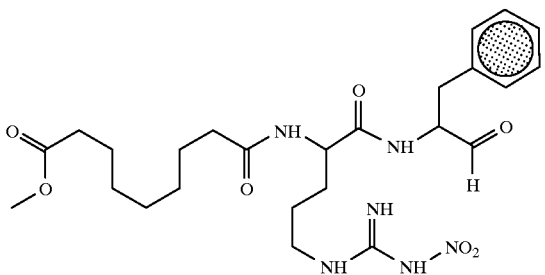

Step 1. Phenylalaninal diethylacetal.

CBZ-Phe-OH (6.0 g, 2 mmol) was converted to phenylalaninal-diethyl acetal following the same procedure used in Leucinal diethylacetal (method F, Example 12).

Step 2: Fmoc-Arg(NO₂)-OH.

A solution of fluorenylmethyloxycarbonyl-N-hydroxysuccinimidyl ester (32 mmol) in 60 mL of THF was added to a stirred solution of N$^g$-nitro-L-arginine (35 mmol) and NaHCO₃(70 mmol) in 70 mL of H₂O. The milky solution cleared after 1 h and the solution was acidified with solid citric acid to pH 2–3 and extracted with 300 mL of EtOAc. The organic layer was washed once with water, dried and evaporated to yield the compound as white solid (26.8 mmol).

Step 3: Fmoc-Arg(NO₂)-Resin.

A solution of 9-fluorenylmethyloxycarbonyl-N$^g$-nitro-L-arginine (from step 2, 26.8 mmol), BOP (30 mmol), HOBt (30 mmol) and NMM (55 mmol) in 40 mL of DMF was mixed with 10 g of PAC resin (α-methylphenacyl linker attached to polystyrene-1% divinylbenzene, substitution 0.97 mmol/g, supplied by Bachem Bioscience, Inc, King of Prussia, Pa.) and stirred for 4 h. The resin was filtered off, washed with DMF, DCM and MeOH and dried to yield the final product Fmoc-Arg(NO₂)-Resin (11.1 g). The resin, Fmoc-Arg(NO₂)-Resin (11.1 g) was treated with 100 ml of a solution containing piperidine (30%), DMF (35%) and toluene (35%) and stirred for 2.5 hours. The Fmoc removed resin was filtered and consecutively washed with DCM/DMF (50:50) and MeOH to yield the product (9.2 g)

Step 4: MeOAz:Arg(NO₂)-Resin.

Monomethyl azelate (20 mmol) was added to a stirred slurry of the Arg(NO₂)-Resin (9.2 g), BOP (20 mmol), HOBt (20 mmol) and NMM (to adjust the pH to 8). After overnight stirring, a mixture of monomethylazelate(10 mmol), BOP (10 mmol), HOBt (10 mmol), and NMM (20 mmol) was added and stirred for 24 hours. The resin was washed with DMF, DCM and methanol to yield 10.56 g of the resin.

Step 5: Monomethylazelayl-N$^g$-nitro-L-arginine:

The product from step 4(10.56 g) was stirred for 5 h in a solution of 100 mL of 67% DCM (30%) TFA and (3%) anisole. The slurry was filtered and the solvent was evaporated and triturated with ether to yield the peptide (1.11 g, 2.75 mmol).

Step 6: Monomethylazelayl-N$^g$-nitro-L-arginyl-L-phenylalaninal diethylacetal.

Following Method C (Example 9), methoxyazelaoyl-N$^g$-nitro-L-arginine (1 mmol) was coupled with L-phenylalaninal diethylacetal (1.3 mmol) using BOP (1.3 mmol), HBOt (1.3 mmol) and NMM (to adjust the pH to 8) to yield the title peptide (0.82 mmol).

Step 7: Monomethylazelayl-N$^g$-nitro-L-arginyl-L-phenylalaninal.

Using Method E (Example 11), product (0.82 mmol) from step 6 was converted to the title compound (0.81 mmol). ¹H NMR (300 MHz, CDCl₃) δ 9.59(s, 1H), 8.36(s, 1H), 7.49(s, 1H), 7.31–7.09 (m, 7H), 6.71 (d, 1H), 4.69 (m, 1H), 4.60 (m, 1H), 3,66 (s, 3H), 3.41 (m, 2H), 3.27 (m, 2H), 2.31 (t, 2H), 2.2 (t, 2H), 1.80–1.2 (m, 14H)

EXAMPLE 28

Monomethylazelayl-N$^g$-(2,2,5,7, 8-pentamethylchroman-6-sulfonyl)-L-arginyl-L-leucinal

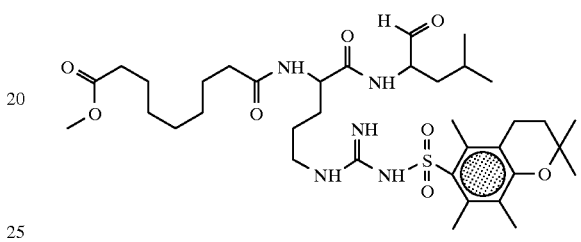

Step 1: Monomethylazelayl-N$^g$-(2,2,5,7,8-pentamethylchroman-6-sulfonyl)-L-arginyl-L-leucinal diethylacetal.

Following Method C (Example 9), monomethylazelate (1.42 g, 7.0 mmol) was coupled with N$^g$-(2,2,5,7,8-pentamethylchroman-6-sulfonyl)-L-arginyl-L-leucinal diethylacetal (3.06 g, 5.0 mmol, obtained from step 2 in Example 20), using 7.0 mmol each of BOP, HOBt and NMM to obtain the compound (3.43 g) as solid. ¹H NMR (300 MHz, CDCl₃) δ: 6.58(d, 1H), 6.04(d, 1H), 5.4(br, 1H), 5.06(br, 1H), 4.47 (m, 1H), 4.30 (d, 1H), 4.17 (m, 1H), 3.67 (s, 3H), 3.53 (m, 4H), 3.23 (d, 1H), 3.19 (t, 2H), 2.30 (m, 2H), 2.2 (tt, 2H), 2.0–1.25 (2 br m, 17H), 1.20 (tt, 6H), 0.90 (dd, 6H).

Step 2: Monomethylazelayl-N$^g$-(2,2,5,7,8-pentamethylchroman-6-sulfonyl)-L-arginyl-L-leucinal.

Using Method E (Example 11), the product (0.30 g) from step 1 was converted to Compound 28 (0.22 g). ¹H NMR (300 MHz, DMSO-d₆) δ: 9.38 (s, 1H), 8.5 (br, 1H), 4.30 (m, 1H), 4.09 (m, 1H), 3.57 (s, 3H), 3.15 (m, 2H), 3.00 (t, 2H), 2.75 (m, 2H), 2.12 (t, 2H), 1.8–1.20 (2 br m, 17H), 0.86 (dd, 6H)

EXAMPLE 29

Monomethylazelayl-N$^g$-(2,2,5,7,8-pentamethylchroman-6-sulfonyl)-D-arginyl-L-leucinal

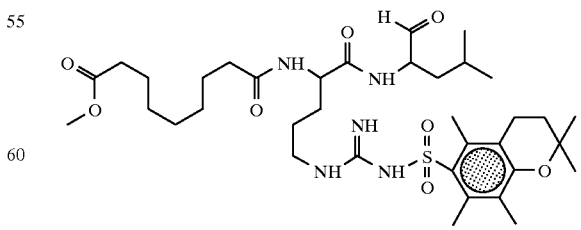

Step 1: 9-Fluorenylmethoxycarbonyl-N$^g$-(2,2,5,7,8-pentamethylchroman-6-sulfonyl)-D-arginyl-L-leucinal diethylacetal.

Following Method C (Example 9), 9-Fluorenylmethyloxycarbonyl-N$^g$-(2,2,5,7,8-pentamethylchroman-6-sulfonyl)-D-arginine (3 mmol) was coupled with leucinal diethylacetal (2.5 mmol) using BOP (3 mmol), HOBt (3 mmol) and NMM (5 mmol) in 5mL of DMF to yield the peptide (1.72 g, 2 mmol) as a solid.

Step 2: MeOAz-D-Arg(PMC)-Leucinal diethylacetal.

Using Method C (Example 9), monomethylazelate (1.0 mmol) was coupled with N$^g$-(2,2,5,7,8-pentamethylchroman-6-sulfonyl)-D-arginyl-L-leucinal diethylacetdal (0.54 g, 0.88mmol) obtained from title product of Step 1 following method B (Example 8), using BOP (1 mmol), HBOt (1 mmol) and NMM (3 mmol) in 5 mL of DMF to yield the product (0.735 g).

Step 3: Monomethylazelayl-N$^g$-(2,2,5,7,8-pentamethylchroman-6-sulfonyl)-D-arginyl-L-leucinal.

Using method E (Example 11), the product (0.1 g) from step 2 was converted to Compound 29 and purified by HPLC. $^1$H NMR(300 MHz, CDCl$_3$) δ: 9.49 (s,1H), 7.74 (t, 1H), 7.43 (d, 1H), 6.43 (d, 1H), 6.34 (s, 2H), 4.60 (m, 1H), 4.51 (s, 3H), 4.54 (s, 3H), 4.37 (m, 1H), 3.66 (s, 3H), 3.31 (m, 2H), 2.63 (t, 2H), 2.26 (m, 4H), 2.09 (s, 3H), 1.80 (t, 2H), 1.57 (m, 7H), 1.26 (m, 16H), 0.90 (dd, 6H)

EXAMPLE 30

Monomethylazelayl-N$^g$-(2,2,5,7,8-pentamethylchroman-6-sulfonyl)-L-arginyl-L-norleucinal

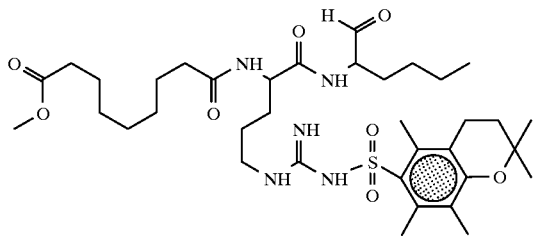

Step 1: Fmoc-N$^g$-(2,2,5,7,8-pentamethylchroman-6-sulfonyl)-L-arginyl-L-norleucinal.

Fmoc-Arg(PMC)-OH (2 mmol) was coupled with norleucinal diethylacetal (2 mmol, obtained from CBZ-Nle-OH following the procedures in the preparation of Leu-acetal) using BOP (2 mmol), HOBt (2 mmol) and NMM (6 mmol) in 6 mL of DMF, according to the Method C (Example 9), to yield the peptide (1.37 g, 1.64 mmol).

Step 2: MeOAz-Arg(PMC)-L-norleucinal diethyl azetal.

Following Method C (Example 9), monomethyl azelate (2 mmol) was coupled with Arg(PMC)-norleucinal diethyl acetal (1.39 mmol, obtained from step 1 following Method B, Example 8) using BOP (2 mmol), HOBt (2 mmol) and NMM (6 mmol) and stirred overnight. The next day, 1 mmol each of monomethylazelate, BOP, HOBt and NMM were added and stirred for 4 hours. The reaction mixture was worked-up as in Method C, Example 9), to yield the peptide (0.37 g, 0.84 mmol)

Step 3: Following Method E (Example 11), the product from step 2 (0.94 g, 0.84 mmol) was converted to Compound 30 (0.58 g) $^1$H NMR(300 MHz, CDCl$_3$) δ: 9.54 (s, 1H), 7.49 (t, 1H), 6.74 (d, 1H), 6.26 (s, 2H), 6.23 (d,1H), 4.58 (m, 1H), 4.31 (m, 1H), 3.66 (s, 3H), 3.34 (m, 2H), 2.63 (t, 2H), 2.58 (s, 3H), 2.56 (s, 3H), 2.29 (t, 2H), 2.23 (t, 2H), 1.9–1.5 (m, 22H), 1.30 (s, 6H), 0.86 (t, 3H)

EXAMPLE 31

Monomethylazelayl-N$^g$-(p-toluenesulfonyl)-L-arginyl-L-leucinal

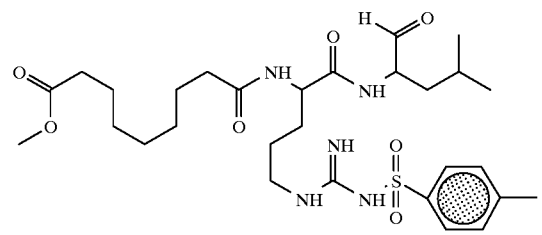

Step 1: Fmoc-N$^g$-(p-toluenesulfonyl)-L-arginyl-L-leucinal diethylacetal.

Using Method C (Example 9), Fmoc-N$^9$-(p-toluenesulfonyl)-L-arginine (5 mmol) was coupled with leucinal diethylacetal (5.5 mmol) using HBTU (5. 5 mmol), HOBt (5.5 mmol) and NMM (11 mmol) in 15 mL of DMF. The peptide was isolated as a solid (2.86 g, 3.96 mmol).

Step 2: Monomethylazelayl-N$^g$-(p-toluenesulfonyl)-L-arginyl-L-leucinal diethylacetal.

Following Method C (Example 9), monomethyL azelate (6 mmol) was coupled with N$^g$-(p-toluenesulfonyl)-L-arginyl-L-leucinal diethylacetal (2.7 g, 4.7 mmol, obtained from Step 1 using Method B, Example 8), using 1-benzotriazol-1-yl-1,1,3,3-tetramethyluronium hexafluorophosphate (HBTU) (6 mmol), HOBt (6 mmol) and NMM (12 mmol) in 15 mL of DMF and stirring overnight. The reaction yield was boosted by adding monomethyl azelate (3 mmol) and diphenylphosphoryl azide (3 mmol) and stirred for 4 hours to yield the peptide as solid (1.92 g).

Step 3: Monomethylazelayl-N$^g$-(p-toluenesulfonyl)-L-arginyl-L-leucinal

According to Method E (Example 11), the product from step 2 (1.92 g, 2.8 mmol) was converted to Compound 31 (1.64 g) $^1$H NMR (300 MHz, DMSO-d6) δ: 9.37 (s, 1H), 8.97 (d, 1H), 8.37 (d, 1H), 7.66 (d, 2H), 7.37 (m, 1H), 7.29 (d, 2H), 7.03 (s, 1H), 6.63 (s, 1H), 4.09 (m, 1H), 3.57 (s, 3H), 3.44 (m, 1H), 3.04 (m, 2H), 2.26 (s, 3H), 2.33 (t, 2H), 2.13 (t, 2H), 2.80–1.09 (m, 7H), 0.86 (dd, 6H).

EXAMPLE 32

Monomethylazelayl-N$^g$-(4-methoxy,2,3,6-trimethyl-1-sulfonyl)-L-arginyl-L-leucinal semicarbazone

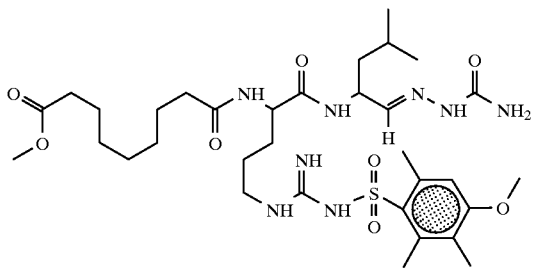

See Basak, A. et al., *Int. J. Peptide Protein Res.* 36 7–17 (1990). A mixture of MeOAz-Arg(MTR)-Leu-H (Example 34) (67 mg, 0.10 mmol), semicarbazide hydrochloride (11 mg, 0.1 mmol) and sodium acetate (9 mg, 0.11 mmol) in 3 mL of 90% EtOH was heated to 70° C. for 18 h. The reaction mixture was concentrated to afford a light yellow solid (Compound 32) which was subsequently purified by HPLC as in Table 6. $^1$H NMR (300 MHz, CDCl$_3$) δ: 7.91 (t, 1H), 7.09 (d, 1H), 6.68 (s, 1H),6.22 (s, 1H), 4.37–4.46 (m, 1H), 4.2–4.3 (m, 1H), 4.04 (d, 1H), 3.7 (s, 3H), 3.58 (s, 3H), 2.6 (s, 3H), 2.27 (dd, 2H), 2.05, 2.12 (s, 3H), 1.2–1.64(m, 12H), 0.85(t, 6H)

EXAMPLE 33

Monomethylazelayl-N$^g$-(4-methoxy,2,3,6-trimethyl-1-sulfonyl)-L-arginyl-L-leucinal thiosemicarbazone)

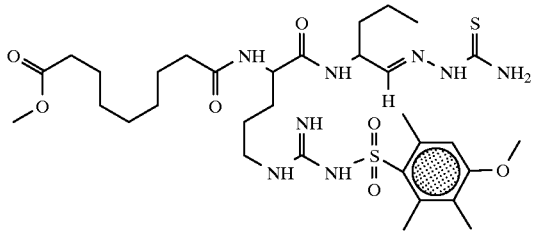

Following the same steps in Example 32, Compound 33 was made from the Compound of Example 34 (51 mg, 0.07 mmol) and thiosemicarbazide (7 mg, 0.07 mmol) in 2 mL of 90% EtOH.

EXAMPLE 34

Monomethylazelayl-N$^g$-(4-methoxy,2,3,6-trimethylbenzene-1-sulfonyl)-L-arginyl-L-leucinal

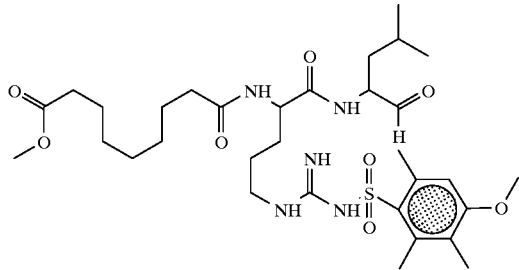

Step 1: Following method C (Example 9), 9-fluorenylmethyloxycarbonyl-N$^g$(4-methoxy-2,3,6-trimethylbenzene-1-sulfonyl)-L-arginyl-L-leucinal diethyl acetal was prepared from 9-fluorenylmethyloxycarbonyl-N$^g$-(4-methoxy-2,3,6-trimethylbenzene-1-sulfonyl)-L-arginine and L-leucinal diethyl acetal.
Step 2: Monomethylazelayl-N$^g$-(4-methoxy-2,3,6-trimethylbenzenesulfonyl)-L-arginyl-L-leucinal.

Following Method C (Example 9), monomethylazelate (6 mmol) was coupled with N$^g$-(4-methoxy-2,5,6-trimethylbenzene-1-sulfonyl)-L-arginyl-L-leucinal diethylacetal (5 mmol, obtained from step 1 using Method B, Example 8), and the peptide was isolated as an amorphous solid (3.3 g).
Step 3: Methoxyazelayl-N$^g$-(4-methoxy-2,3,6-trimethylbenzene-1-sulfonyl)-L-arginyl-L-leucinal.

The product from step 2 (0.5 g) was converted to Compound 34 (0.36 g) according to method E, Example 11. $^1$H NMR (300 MHz, CDCl$_2$) δ: 9.54 (s, 1H), 7.51 (s, 1H), 6.74(d, 1H), 6.57 (s, H), 6.40(s, 2H), 6.31 (s, 1H), 4.66 (m, 1H),4.41 (m, 1H), 3.87 (s, 3H), 3.70 (s, 3H), 3.33(m, 2H), 2.73 (s, 3H), 2.66 (s, 3H), 2.33 (t, 2H), 2.26 (t, 2H), 2.17 (s, 3H), 2.00–1.26 (m, 17H), 0.96 (dd, 6H).

EXAMPLE 35

Methoxyazelayl-N$^g$-(2,4,6-trimethylbenzene-1-sulfonyl)-L-arginyl-L-leucinal

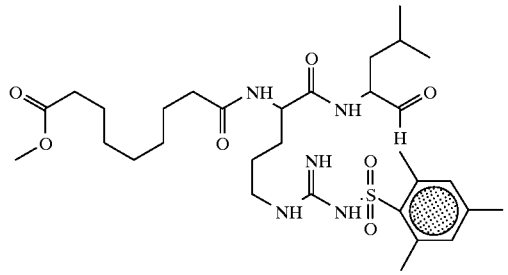

Step 1: Fmoc-N$^g$-(2,4,6-trimethylbenzene-1-sulfonyl)-L-arginyl-L-leucinal diethylacetal.

A solution of 4M HCl in dioxane (10 mL) was added to a solution of Boc-Arg(MTS)-OH (6 mmol) in 10 ml, of dioxane. After 30 minutes, the solvent was removed and ether was added, the precipitate was collected and dried (3.21 g, 9 mmol). The Arg-MTS-OH hydrochloride was converted to Fmoc-Arg(MTS)-OH following the procedure as described for the preparation of the tosyl derivative (Example 31) to yield the title compound as a white solid (2.09 g).
Step 2: Fmoc-Arg(MTS)-Leu-acetal.

Following Method C (Example 9), Fmoc-Arg(MTS)-OH (3.361 mmol) was coupled with leucinal diethylacetal (4 mmol) using HBTU (4 mmol), HOBt (4 mmol) and NMM (10( mmol) in 15 mL of DMF to yield the title peptide (1.05 g)
Step 3: MeOAz-Arg(MTS)-Leu-acetal.

Using Method C, monomethyl azelate (1.2 mmol) was coupled with Arg (MTS)-Leu-acetal (0.85 mmol, obtained from step 2 following Method B, Example 8) using BOP (1.2 mmol), HOBt (1.2 mmol) and NMM (3.6 mmol) in 3 mL of DMF and stirred overnight to give the title peptide as a semi-solid (0.59 g).
Step 4: Methoxyazelaoyl-N$^g$-(2,4,6-trimethylbenzene-1-sulfonyl)-L-arginyl-L-leucinal.

According to Method E (Example 11), the product (0.59 g) of step 3 was converted to Compound 35 (0.54 g) and purified by HPLC. $^1$H NMR (300 MHz, CDCl3) δ: 9.49(s, 1H), 7.53 (s, 1H), 6.90 (s, 2H), 6.81 (d, 1H), 6.40 (bs, 3H), 4.61 (m, 1H), 4.38 (m, 1H), 3.67 (s, 3H), 2.67 (s, 6H), 2.29 (t, 2H), 2.20 (t, 2H), 2.0–1.20 (m, 19H), 0.91 (dd, 6H)

EXAMPLE 36

6-Cyano-hexane-1-sulfonyl-N$^g$-(2,2,5,7,8-pentamethylchroman-6-sulfonyl)-L-arginyl-L-leucinal Step 1: 6-Cyano-hexane-1-sulfonyl-N$^g$-(2,2,5,7,8-pentamethylchroman-6-sulfonyl)-L-arginyl-L-leucinal diethylacetal.

6-cyano-hexane-1-sulfonyl chloride (0.19g, 0.89 mmol) from step 14 in Method G (Example 13) was added to a solution of the product (0.55 g, 0.899 mmol) from step 2 in Example 20, in 1 mL of DMF and the pH of the solution was adjusted to 8 using NMM. After 4 hours of stirring, the reaction mixture was worked up as described in Method A (Example 7), to obtain the title compound (0.466 g).

Step 2: 6-Cyano-hexane-1-sulfonyl-$N^g$-(2,2,5,7,8-pentamethylchroman-6-sulfonyl)-L-arginyl-L-leucinal.

Using method E (Example 11), the product (0.297 g) from step 1 was converted to Compound 36 (0.22 g) and purified by HPLC as described in the Table 6: $^1$H NMR(300 MHz, DMSO-$d_6$) δ: 9.37 (s, 1H), 6.83 (b, 1H), 6.43 (b, 1H), 3.88 (m, 1H), 3.77 (m, 1H), 3.01 (m, 2H), 2.80 (m, 2H), 2.55 (t, 2H), 2.46 (s, 6H), 2.0 (s, 3H), 1.75 (m, 5H), 1.6–1.3 (m, 15H), 1.23 (s, 6H), 0.84 (dd, 6H)

EXAMPLE 37

2-Naphthoyl-$N^g$-nitro-L-arginyl-L-leucinal

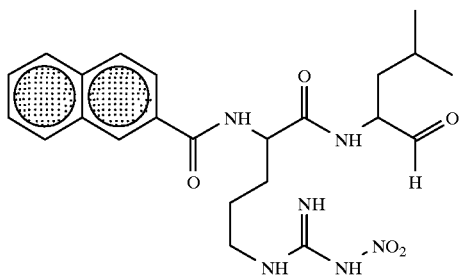

Step 1: 2-Naphthoyl-$N^g$-nitro-L-arginyl-L-leucinal diethylacetal.

2-Naphthoylchloride (0.104 g, 0.55 mmol) was added to a solution of the product from step 2 in Example 14 in 2 mL of DMF and NMM (0.18 mL) and the title product was worked up to obtain the title compound as a solid (22 g). $^1$H NMR (300 MHz, CDCl3) δ: 8.92 (b, 1H), 8.0–7.91 (mm, 10H), 6.93 (d, 1H), 5.07 (m, 1H), 4.37 (d, 1H ), 4.17 (m, 1H), 3.69 (m, 3H), 3.53 (m, 3H), 3.38 (m, 2H) 1.77, 1.58, 1.4 (mm, 5H), 0.83 (dd, 6H).

Step 2: 2-Naphthoyl-$N^g$-nitro-L-arginyl-L-leucinal.

Using Method E (Example 11), the product (0.1 g) from step 1 was converted to the Compound 37 (60 mg). $^1$H NMR (300 MHz, DMSO-$d_6$) δ: 9.43 (s, 1H), 8.72 (d, 1H), 8.53 (m, 2H), 8.0 (m, 6H),7.6 (m, 2H),6.20 (m, 1H), 4.57 (m, 1H), 4.14 (m, 1H), 3.92 (m, 1H), 3.2 (m, 2H), 3.0 (d, 1H), 1.77 (m, 5H), 0.86 (m, 6H).

EXAMPLE 38

CBZ-7-aminoheptanoyl-$N^g$-nitro-L-arginyl-L-leucinal

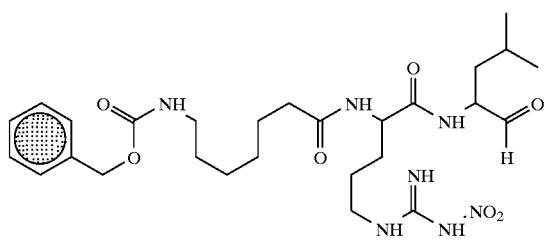

Step 1: CBZ-7-aminoheptanoyl-$N^g$-nitro-L-arginyl-L-leucinal diethyl acetal.

Following Method C (Example 9), CBZ-7-aminoheptanoic acid (0.7 g, 2.5 mmol) was coupled with the product of step 2 in Example 14 (0.78 g, 2.0 mmol) using BOP (1.1 g, 2.5 mmol), HOBt (0.34 g, 2.5 mmol) and NMM (0.253 mL, 2.5 mmol) to yield the peptide as a semi-solid, which was used directly in the next step.

Step 2: CBZ-7-aminoheptanoyl-$N^g$-nitro-L-arginyl-L-leucinal.

Following Method E (Example 11), the acetal from step 1 was converted to Compound 38 (0.8 g) after stirring the reaction for 5 h. $^1$H (300 MHz, DMSO-$d_6$) δ 9.30 (s, 1H), 8.47 (s, 1H), 8.46 (s, 1H), 8.29 (d, 1H), 8.11 (t, 1H), 7.80 (s, 1H), 7.64 (d, 1H), 7.31 (s, 1H), 7.23 (s, 1H), 4.91 (s, 2H), 4.23 (m, 1H), 4.00 (m, 1H), 3.51 (q, 2H), 3.27 (m, 2H), 2.89 (q, 2H), 2.11 (t, 2H), 2.03 (t, 2H), 1.7–1.00 (m, 10H), 0.77 (dd, 6H)

Examples 39–42 describe the syntheses of the MCP inhibitors listed in Table 7.

TABLE 7

| Example No. | % Inhibition (1 μM) | IC$_{50}$ nM |
| --- | --- | --- |
| 39 (Isomer a) | 31 | >1000 |
| 39 (Isomer b) | 21 | >1000 |
| 40 | 100 | 6 |
| 41 (Isomer a) | 99 | 22 |
| 41 (Isomer b) | 98 | 13 |
| 42 | 15 | >1000 |

EXAMPLE 39

10-Cyano-2-cyclopentyl-decanoyl-$N^g$-nitro-L-arginyl-L-leucine chloromethylketone

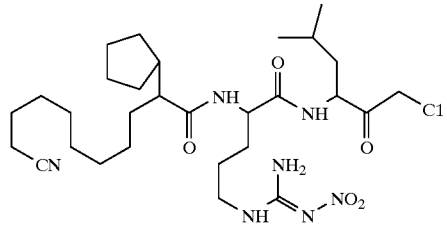

In this and in the following three examples, the inhibitors of the invention are prepared by Coupling Procedure II. In each case, 10-cyano-2-cyclopentyl-decanoyl-$N^g$-nitro-L-arginine prepared as herein described is coupled to an enzyme-reactive amino acid derivative to produce the inhibitor. These inhibitors are obtained as a mixture of two or more diastereoisomers which in some cases may be separable by HPLC.

A) 10-Cyano-2-cyclopentyl-decanoyl-$N^g$-nitro-L-arginine methyl ester

Following the procedure of Method C (Example 9), 10-cyano-2-cyclopentyl-decanoic acid (2.4 g; 11 mmol) from Example 13 Step 5, in 26 mL of DMF was stirred with $N^g$-nitro-L-arginine methyl ester dihydrochloride (2.86 g, 11 mmol), BOP (6.6 g, 15 mmol), HOBt (1.62 g, 12 mmol) and 3.6 mL of NMM (33 mmol) to yield 4.8 g of the methyl ester as a foamy solid. $^1$H NMR: (300 MHz, CDCl$_3$) δ 8.75 (bs, 1H), 7.81 (bs, 2H), 6.42 (d, 1H), 4.67 (t, 1H), 3.82 (s, 3H), 3.75 (m, 1H), 3.32 (m, 1H), 2.15 (t, 2H), 2.05–1.12 (m, 28H)

B) 10-Cyano-2-cyclopentyl-decanoyl-$N^g$-nitro-L-arginine

A solution of 5.5 g of the methyl ester from part "A" above in 30 mL of methanol was treated with 24 mL of 1.00N aqueous sodium hydroxide. After 2 hours, 100 mL of 2% aqueous sodium bicarbonate solution was added, and the resulting solution was extracted with 100 mL of ether. The aqueous layer was separated and acidified with 3% aqueous citric acid and extracted with 250 mL of ethyl acetate. The resulting organic layer was separated, dried over anhydrous $MgSO_4$ and evaporated to yield a colorless gum which on trituration with petroleum ether solidified to a fine white powder weighing 4.4 g. $^1$H-NMR (300 MHz, $CDCl_3$) δ 10.6 (bs, 1H), 8.75 (bs, 1H), 7.82 (bs, 2H), 6.41 (d, 1H), 4.67 (t, 1H), 3.71 (m, 1H), 3.32 (m, 1H), 2.15 (t, 2H), 2.04–1.12 (m, 30H).

C) 10-Cyano-2-cyclopentyl-decanoyl-$N^g$-nitro-L-arginyl-L-leucine chloromethyl ketone.

A mixture of 467 mg (1.0 mmol) of the product from part "B" above and 270 mg (1.0 mmol) of leucine chloromethyl ketone hydrochloride (Bachem Biosciences, Inc., King of Prussia, Pennsylvania), 440 mg (1.0 mmol) of BOP and 135 mg (1 mmol) of HOBt in 4.0 mL of DMF was treated with 0.33 mL (3 mmol) of NMM. After 4 hours. the mixture was diluted with 75 mL of ethyl acetate, washed with 2% aqueous $NaHCO_3$, water, 3% aqueous citric acid and finally with water. The organic layer was separated and dried ($MgSO_4$) and finally evaporated to give a pale yellow, viscous oil. This compound was purified by flash chromatography through a 9×½ inch column of silica gel 60-H using ethyl acetate for elution. The resulting solution was evaporated to give a colorless gum which solidified on standing in 1:1 ethyl acetate/ether to give 198 mg of colorless solid chloromethyl ketone. HPLC indicated the presence of two diastereoisomers which were separated by preparative RP-HPLC. In a water-acetonitrile solvent gradient (30–80% of acetonitrile in 40 min.) the peaks at 22.58 min.(diastereoisomer a) and 23.7 min. (diastereoisomer b) were isolated.

Diastereoisomer a: $^1$H-NMR (300 MHz, $CDCl_3$) δ 8.53 (bs, 1H), 7.61 (bs, 2H), 7.31 (bs, 1H), 6.69 (d, 1H), 4.73 (m, 1H), 4.65 (m, 1H), 4.28 (q, 2H), 3.53 (m, 1H), 3.31 (t, 1H ), 2.32 (t, 2H), 1.90–1.11 (m, 31H), 0.93 (q, 6H).

Diastereoisomer b: $^1$H-NMR (300 MHz, $CDCl_3$) δ 8.53 (bs, 1H), 7.61 (bs, 2H), 7.31 (bs, 1H), 6.79 (d, 1H), 4.73 (m, 1H), 4.65 (m, 1H), 4.28 (q, 2H), 3.53 (m, 1H), 3.31 (t, 1H), 2.32 (t, 2H), 1.90–1.11 (m, 31H), 0.93 (q, 6H).

EXAMPLE 40

10-Cyano-2-cyclopentyl-decanoyl-$N^g$-nitro-L-arginyl-boroleucine pinacol ester

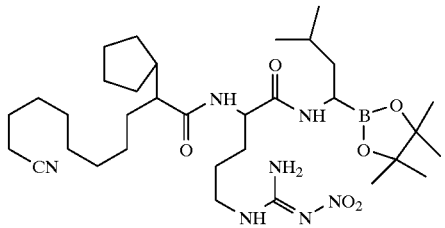

A solution of 467 mg (1.0 ml of 10-cyano-2-cyclopentyl-decanoyl-$N^g$-nitro-L-arginine (Example 39, part "B" above) and 264 mg (1.0 mmol) of boroleucine pinacol ester hydrochloride prepared by the method of Shenvi, U.S. Pat. No. 4,537,773, 440 mg (1.0 mmol) of BOP and 135 mg (1.0 mmol) of HOBt in 5.0 mL of DMF was treated with 0.33 mL (3 mmol) of NMM. After 2 hours, the mixture was diluted with 75 mL of ethyl acetate and washed with 2% aqueous $NaHCO_3$ and water, and the organic layer was separated, dried ($MgSO_4$) and evaporated to yield 410 mg of a pale brown powder. This solid was washed with chloroform to give 290 mg of product as an off-white solid which exhibited a single peak in the HPLC. $^1$H-NMR (300 MHz, $CDCl_3$) δ 8.53 (bs, 1H), 7.65 (bs, 2H), 6.71 (t, 1H), 4.61 (m, 1H), 3.52 (m, 1H), 3.31 (m, 2H), 3.05 (m, 1H), 2.82 (m, 1H), 2.38 (t, 2H), 2.06–1.42 (m, 28H), 1.22 (s, 12H), 1.15 (m, 2H), 0.92 (m, 6H).

EXAMPLE 41

10-Cyano-2-Cyclopentyl-decanoyl-$N^g$-nitro-L-arginyl-L-leucine alpha-ketoethylamide

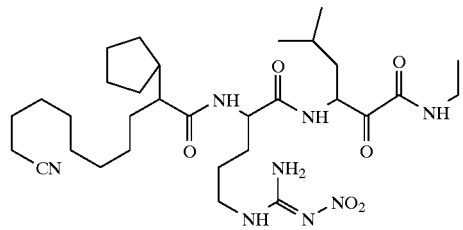

A) 10-Cyano-2-cyclopentyl-decanoyl-$N^g$-nitro-L-arginyl-(1-ethylaminocarbonyl 1-hydroxy-4-methyl)-2-pentylamide A solution of 467 mg (1.0 mmol) of 10-cyano-2-cyclopentyl-decanoyl-$N^g$-nitro-L-arginine and 225 mg of 3-amino-2-hydroxy-5-methyl-hexanoic acid N-ethylamide hydrochloride (prepared by the method of Harbeson et al, *J.Med.Chem.* 37, 2918-29 (1994)) in 5.0 mL of DMF was treated with 440 mg (1 mmol) of BOP, 135 mg (1 mmol) of HOBt and 0.33 mL (3 mmol) of NMM. After stirring for 2 hours., the solution was diluted with 75 mL of ethyl acetate and washed with 2% aqueous $NaHCO_3$, water, 3% aqueous citric acid, water and dried ($MgSO_4$) to yield, after evaporation, 540 mg of the hydroxy compound as an off-white solid. $^1$H-NMR. (300 MHz, $CDCl_3$) δ 8.53 (bs, 1H), 7.73 (bs, 2H), 7.04 (bm, 1H), 6.83 (t, 1H), 4.52 (m, 1H), 4.19 (m, 1H), 4.11 (q, 2H), 3.46 (q, 2H), 3.26 (m, 2H), 2.35 (t, 2H), 1.91 (m, 2H), 1.83 (m, 2H), 1.8–1.2 (m, 28H), 1.13 (t, 3H), 0.88 (m, 6H).

B) 10-Cyano-2-cyclopentyl-decanoyl-$N^g$-nitro-L-arginyl-L-leucine alpha-ketoethylamide A solution of 250 mg of the hydroxy compound from part "A" above in 6.0 mL of dry dichloromethane was cooled to 0° C. and stirred with 225 mg (ca. 0.5 mmol) of Dess-Martin reagent (D.B.Dess and J.C.Martin, *J. Org. Chem.* 48, 4156–4158 (1983)).

The reaction was allowed to warm to room temperature and was stirred for 2 hours. The cloudy suspension was diluted with 50 mL of ethyl acetate and filtered through a fine sintered-glass filter. The filtrate was washed with 10% aqueous $Na_2S_2O_3$ and then with saturated NaCl. It was dried ($MgSO_4$) and evaporated to give 180 mg of white solid ketoamide product. It was purified by preparative RP-HPLC using a water-acetonitrile gradient system (40–70% acetonitrile in 40 min.). The peaks at 18.07 min. (diastereoisomer a) and 19.54 min. (diastereoisomer b) were collected.

Diastereoisomer a: $^1$H-NMR: (300 MHz, $CDCl_3$) δ 8.45 (bs, 1H), 7.58 (bs, 2H), 7.04 (bm, 2H), 6.57 (t, 1H), 5.33 (t, 1H), 4.60 (m, 1H), 3.51 (m, 1H), 3.33 (m, 3H), 2.35 (t, 2H), 1.91–1.11 (m, 34H), 0.94 (m, 6H).

Diastereoisomer b: $^1$H-NMR (300 MHz, $CDCl_3$) δ 8.45 (bs, 1H), 7.48 (bs, 2H), 7.25 (m, 1H), 7.04 (t, 1H), 6.85 (m, 1H), 6.62 (d, 1H), 5.32 (t, 1H), 4.81 (m, 1H), 4.58 (m, 1H), 3.51 (m, 1H), 3.35 (m, 3H), 2.35 (t, 2H), 1.95–1.11 (m, 32H), 0.98 (m, 6H).

EXAMPLE 42

10-Cyano-2-cyclopentyl-decanoyl-N$^g$-nitro-L-arginyl-phenylalanine fluoromethylketone

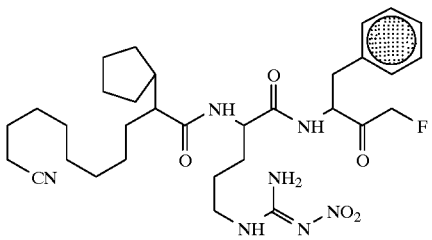

A) Synthesis of 1-Nitro-2-phenylethane

To a stirring mixture of trans-β-nitrostyrene (5.25 g, 0.035 mol) and silica gel (10 g, 230–400 mesh) in chloroform (400 mL) and isopropanol (75 mL) at room temperature, was slowly added sodium borohydride (5.50 g, 0.145 mol) over a period of 45 min. The reaction mixture was stirred for an additional 15 min and then carefully quenched with 10% hydrochloric acid (20 mL). Separated solid wins filtered and washed with chloroform (50 mL). Combined filtrate and washing was washed with water (1×20 mL), brine (1×20 mL) and dried over anhydrous sodium sulfate. Solvent evaporation at reduced pressure gave a crude material which was purified by flash chromatography (silica gel, 8% ethyl acetate-hexane) to give 2.86 g of 1-nitro-2-phenylethane as a colorless oil (spicy odor); Rf (10% ethyl acetate in hexane): 0.40; $^1$H-NMR (300 MHz, CDCl$_3$) 7.40–7.20 (m, 5H), 4.60 (t, 2H), 3.30 (t, 2H).

B) Synthesis of 1-Fluoro-2-hydroxy-3-nitro-4-phenylbutane

To a cooled (−78° C.) solution of oxalyl chloride (2M) in methylene chloride (11.60 mL, 0.0232mol) was added slowly dimethyl sulfoxide (3.65 g, 3.32 mL, 0.0467 mol). The reaction mixture was stirred for 15 min. A solution of 2-fluoroethanol (1.16 g, 0.0181 mol) in methylene chloride (10 mL) was then slowly introduced into the reaction flask. After stirring for another 15 min, the reaction mixture was diluted with anhydrous methylene chloride (180 mL), and triethylamine (9.20 g, 12.63 mL, 0.090 mol) was added to it. Stirring was continued for another 2 h by which time the temperature had risen to room temperature. At this time, a solution of 1-nitro-2-phenylethane (2.74 g, 0.0181 mol) in anhydrous methylene chloride (10 mL) was added to the reaction mixture and stirring was continued overnight. The mixture was then washed with water (1×30 mL), 4% hydrochloric acid (3×20 mL), water (1×20 mL), saturated sodium bicarbonate solution (2×20 mL) and brine (1×20 mL). Drying over anhydrous sodium sulfate and solvent evaporation gave a crude material which was purified by flash chromatography (silica gel, 25% ethyl acetate-hexane) to give the product as erythro and threo isomers. Combined yield was 3.01 g. A general description of this procedure can be found in Imperiali, B., et al., *Tetrahedron Lett.* 27 (2), 135 (1986) and in Revesz, L., et al., *Tetrahedron Lett.* 35 (52), 9693 (1994).

Isomer a was a white solid, mp 71–73° C.; R$_f$ (30% ethyl acetate in hexane): 0.46; $^1$H-NMR (300 MHz, CDCl$_3$) δ 7.40–7.10 (m, 5H), 4.90 (m, 1H), 4.60 (m, 1H), 4.50–4.30 (m, 2H), 3.45–3.25 (m, 2H), 2.70 (d, 1H).

Isomer b was a colorless oil; R$_f$ (30% ethyl acetate in hexane): 0.42; $^1$H-NMR (300 MHz, CDCl$_3$) δ 7.40–7.15 (m, 5H), 4.90 (m, 1H), 4.65 (m, 1H), 4.50 (m, 1H), 4.20 (m, 1H), 3.40–3.30 (m, 2H), 2.90 (d, 1H).

C) Synthesis of 3-Amino-1-fluoro-2-hydroxy-4-phenylbutane

A mixture of the above isomer a (0.48 g, 2.25 mmol), absolute ethanol (20 mL) and Raney-Nickel (catalytic) was hydrogenated (60 psi) in a Parr apparatus for 5 hours. Filtration through a Celite pad and solvent evaporation gave 410 mg of amine isomer a. Similar treatment of the above isomer b (800 mg, 3.75 mmol) gave 510 mg of amine isomer b.

Amine isomer a was a white solid, mp 64–67° C.; $^1$H-NMR (300 MHz, CDCl$_3$) δ 7.40–7.10 (m, 5H), 4.70 (d, 1H), 4.50 (d, 1H), 3.90–3.70 (m, 1H), 3.30–3.10 (m, 1H), 2.95 (dd, 1H), 2.60–2.45 (q, 1H), 2.20–1.70 (broad, 3H).

Amine isomer b was a white solid, mp 67–70° C.; $^1$H-NMR (300 MHz, CDCl$_3$) δ 7.40–7.10 (m, 5H), 4.70 (d, 1H), 4.55 (d, 1H), 3.70–3.50 (m, 1H), 3.20–3.00 (m, 1H), 2.95 (dd, 1H), 2.60–2.45 (q, 1H), 2.20–1.65 (broad, 3H).

D) 10-Cyano-2-cyclopentyl-decanoyl-N$^g$-nitro-L-arginyl-(4-fluoro-3-hydroxy-1-phenyl)-2-butylamide A solution of 467 mg (1.0 mmol) of 10-cyano-2-cyclopentyl-decanoyl-N$^g$-nitro-L-arginine and 183 mg (1.0 mmol) of 3-amino-1-fluoro-2-hydroxy-4-phenyl-butane in 5.0 mL of DMF was treated with 440 mg (1.0 mmol) of BOP, 135 mg (1.0 mmol) of HOBt and 0.33 mL (3 mmol) of NMM. After stirring for 2 hours., the solution was diluted with 75 mL of ethyl acetate and washed with 2% aqueous NaHCO$_3$, water, 3% aqueous citric acid, water and dried (MgSO$_4$) to yield after evaporation 480 mg of the hydroxy compound as an off-white solid. $^1$H-NMR (300 MHz, CDCl$_3$ +d$_6$-DMSO) δ 8.15 (bs, 1H), 7.82 (bs, 2H), 7.21 (m, 6H), 5.05 (t, 1H), 4.51 (m, 1H), 4.22 (m, 1H), 3.82 (m, 1H), 3.75 (m, 2H), 2.95 (q, 2H), 2.35 (t, 2H), 2.04–1.13 (m, 31H).

E) 10-Cyano-2-cyclopentyl-1-decanoyl-N$^g$-nitro-L-arginyl-phenylalanine fluoromethylketone A solution of 250 mg of the hydroxy compound from part "C" above in 6.0 mL of anhydrous dichloromethane was cooled to 0° and stirred with 225 mg (ca. 0.5 mmol) of Dess-Martin reagent. The reaction was allowed to warm to room temperature and was stirred for 2 hours. The cloudy suspension was diluted with 50 mL of ethyl acetate and filtered through a fine sintered glass filter. The filtrate was washed with 10% aqueous Na$_2$S$_2$O$_3$ and then with saturated NaCl. It was dried (MgSO$_4$) and evaporated to give 180 mg of white solid. After HPLC purification, 42 mg of pure fluoromethyl ketone product was obtained. $^1$H-NMR: (300 MHz, CDCl$_3$) δ 8.56 (bs, 1H), 7.62 (bs, 2H), 7.42 (t, 1H), 7.21 (m, 5H), 6.63 (m, 1H), 5.05–4.53(m, 4H), 3.46 (m, 1H), 3.18 (m, 2H), 2.98 (q, 2H), 2.33 (t, 2H), 2.04–1.13 (m, 27H).

Each of the published documents referred to in this specification is herein incorporated by reference in its entirety.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

What is claimed is:

1. A composition for the reduction of Cu/Zn superoxide dismutase-1 enzyme degradation comprising an inhibitor of multicatalytic protease and a pharmaceutically acceptable carrier.

2. The composition of claim 1 wherein the inhibitor of multicatalytic protease is a compound of formula:

$$R_1-(CH_2)_n-CH(R_2)-C(=O)-NH-CH(R_3)-C(=O)-NH-R_4$$

wherein:

$R_1$ is selected from the group consisting of —C≡N, —C(=O)OR$_9$, phthalimido, —NH—SO$_2$R$_9$, and —NH—J;

$R_2$ is selected from the group consisting of H, hydroxyl, alkyl having from one to ten carbons, and cycloalkyl having from three to seven carbons;

$R_3$ is selected from the group consisting of —(CH$_2$)$_m$—NH—C(=N—R$_5$)—NH$_2$, —R$_6$—NO$_2$, —R$_6$—J, and —R$_6$—CN;

$R_4$ is —CH(CH$_2$—R$_7$)—Q;

Q is selected from the group consisting of —CH—R$_8$, —C(=O)CH$_3$, —C(=O)CH$_2$Cl, —C(=O)CH$_2$Br, —C(=O)CH$_2$F, —C(=O)CHF$_2$, —C(=O)CF$_3$, —C(=O)C(=O)R$_7$, —C(=O)C(=O)NH—R$_7$, —C(=O)CO$_2$—R$_7$, —C(=O)CO$_2$H, —B(OH)$_2$, $$-B(-O-C(CH_3)_2-C(CH_3)_2-O-)$$

$$-B(-O-(CH_2)_p-O-)$$

-continued

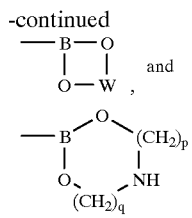

where p and q, independently, are 2 or 3;
W is cycloalkyl;
$R_5$ is selected from the group consisting of —$NO_2$, —CN, and —J;
$R_6$ is —$(CH_2)_m$—NH—C(=NH)—NH—;
$R_7$ is selected from the group consisting of phenyl, and alkyl having from one to eight carbons, said alkyl group being optionally substituted with one or more halogen atoms, aryl, or heteroaryl groups;
$R_8$ is selected from the group consisting of =O, =N—NHC(=O)—$NH_2$, =N—OH, =N—$OCH_3$, =N—O—$CH_2$—$C_6H_5$, =NNH—C(=S)—$NH_2$ and =N—NH—J;
$R_9$ is selected from the group consisting of hydrogen, and alkyl having from one to six carbons, said alkyl group being optionally substituted with one or more halogen atoms, aryl or heteroaryl groups;
J is a protecting group;
n is an integer from 3 to 10; and
m is an integer from 2 to 5.

3. A composition for the alleviation of symptoms of a disorder characterized by a reduction in Cu/Zn superoxide dismutase-1 enzyme activity comprising an inhibitor of multicatalytic protease and a pharmaceutically acceptable carrier.

4. The composition of claim 3 wherein the inhibitor of multicatalytic protease is a compound of formula:

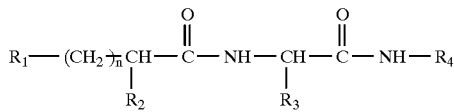

wherein:
$R_1$ is selected from the group consisting of —C≡N, —C(=O)$OR_9$, phthalimido, —NH—$SO_2R_9$, and —NH—J;
$R_2$ is selected from the group consisting of H, hydroxyl, alkyl having from one to ten carbons, and cycloalkyl having from three to seven carbons;
$R_3$ is selected from the group consisting of —$(CH_2)_m$—NH—C(=N—$R_5$)—$NH_2$, —$R_6$—$NO_2$, —$R_6$—J, and —$R_6$—CN;
$R_4$ is —CH($CH_2$—$R_7$)—Q;
Q is selected from the group consisting of —CH—$R_8$, —C(=O)$CH_3$, —C(=O)$CH_2Cl$, —C(=O)$CH_2Br$, —C(=O)$CH_2F$, —C(=O)$CHF_2$, —C(=O)$CF_3$, —C(=O)C(=O)$R_7$, —C(=O)C(=O)NH—$R_7$, —C(=O)$CO_2$—$R_7$, —C(=O)$CO_2H$, —B(OH)$_2$,

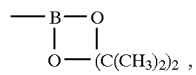

-continued

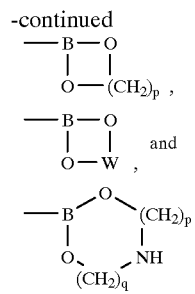

where p and q, independently, are 2 or 3;
W is cycloalkyl;
$R_5$ is selected from the group consisting of —$NO_2$, —CN, and —J;
$R_6$ is —$(CH_2)_m$—NH—C(=NH)—NH—;
$R_7$ is selected from the group consisting of phenyl, and alkyl having from one to eight carbons, said alkyl group being optionally substituted with one or more halogen atoms, aryl, or heteroaryl groups;
$R_8$ is selected from the group consisting of =O, =N—NHC(=O)—$NH_2$, =N—OH, =N—$OCH_3$, =N—O—$CH_2$—$C_6H_5$, =NNH—C(=S)—$NH_2$ and =N—NH—J;
$R_9$ is selected from the group consisting of hydrogen, and alkyl having from one to six carbons, said alkyl group being optionally substituted with one or more halogen atoms, aryl or heteroaryl groups;
J is a protecting group;
n is an integer from 3 to 10; and
m is an integer from 2 to 5.

5. The composition of claim 3 wherein the disorder is selected from the group consisting of amyotrophic lateral sclerosis, Parkinson's disease, Alzheimers's disease, Huntington's disease, stroke, trauma, and ischemia.

6. A method for reducing the degradation of Cu/Zn superoxide dismutase-1 enzyme in a mammal wherein said degradation is a symptom associated with a disease or disorder comprising administering to a patient a therapeutically effective amount of an inhibitor of multicatalytic protease.

7. The method of claim 6 wherein the inhibitor of multicatalytic protease is a compound of formula:

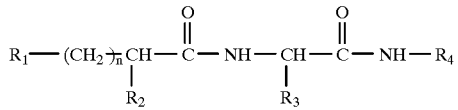

wherein:
$R_1$ is selected from the group consisting of —C≡N, —C(=O)$OR_9$, phthalimido, —NH—$SO_2R_9$, and —NH—J;
$R_2$ is selected from the group consisting of H, hydroxyl, alkyl having from one to ten carbons, and cycloalkyl having from three to seven carbons;
$R_3$ is selected from the group consisting of —$(CH_2)_m$—NH—C(=N—$R_5$)—$NH_2$, —$R_6$—$NO_2$, —$R_6$—J, and —$R_6$—CN;
$R_4$ is —CH($CH_2$—$R_7$)—Q;
Q is selected from the group consisting of —CH—$R_8$, —C(=O)$CH_3$, —C(=O)$CH_2Cl$, —C(=O)$CH_2Br$, —C(=O)$CH_2F$, —C(=O)$CHF_2$, —C(=O)$CF_3$, —C(=O)C(=O)R$_7$, —C(=O)C(=O)NH—R$_7$,
—C(=O)CO$_2$—R$_7$, —C(=O)CO$_2$H, —B(OH)$_2$,

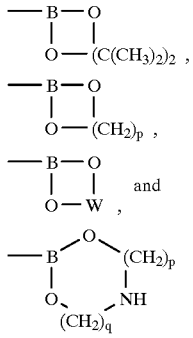

where p and q, independently, are 2 or 3;
W is cycloalkyl;
R$_5$ is selected from the group consisting of —NO$_2$, —CN, and —J;
R$_6$ is —(CH$_2$)$_m$—NH—C(=NH)—NH—;
R$_7$ is selected from the group consisting of phenyl, and alkyl having from one to eight carbons, said alkyl group being optionally substituted with one or more halogen atoms, aryl, or heteroaryl groups;
R$_8$ is selected from the group consisting of =O, =N—NHC(=O)—NH$_2$, =N—OH, =N—OCH$_3$, =N—O—CH$_2$—C$_6$H$_5$, =NNH—C(=S)—NH$_2$ and =N—NH—J;
R$_9$ is selected from the group consisting of hydrogen, and alkyl having from one to six carbons, said alkyl group being optionally substituted with one or more halogen atoms, aryl or heteroaryl groups;
J is a protecting group;
n is an integer from 3 to 10; and
m is an integer from 2 to 5.

8. A method for alleviating a symptom characteristic of a disorder characterized by a reduction in Cu/Zn superoxide dismutase-1 enzyme activity comprising administering to a patient an inhibitor of multicatalytic protease.

9. The method of claim 8 wherein the inhibitor of multicatalytic protease is a compound of formula:

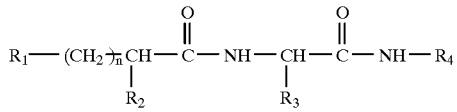

wherein:
R$_1$ is selected from the group consisting of —C≡N, —C(=O)OR$_9$, phthalimido, —NH—SO$_2$R$_9$, and —NH—J;
R$_2$ is selected from the group consisting of H, hydroxyl, alkyl having from one to ten carbons, and cycloalkyl having from three to seven carbons;
R$_3$ is selected from the group consisting of —(CH$_2$)$_m$—NH—C(=N—R$_5$)—NH$_2$, —R$_6$—NO$_2$, —R$_6$—J, and —R$_6$—CN;
R$_4$ is —CH(CH$_2$—R$_7$)—Q;
Q is selected from the group consisting of —CH—R$_8$, —C(=O)CH$_3$, —C(=O)CH$_2$Cl, —C(=O)CH$_2$Br, —C(=O)CH$_2$F, —C(=O)CHF$_2$, —C(=O)CF$_3$, —C(=O)C(=O)R$_7$, —C(=O)C(=O)NH—R$_7$,
—C(=O)CO$_2$—R$_7$, —C(=O)CO$_2$H, —B(OH)$_2$,

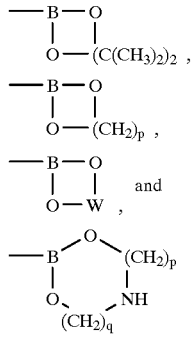

where p and q, independently, are 2 or 3;
W is cycloalkyl;
R$_5$ is selected from the group consisting of —NO$_2$, —CN, and —J;
R$_6$ is —(CH$_2$)$_m$—NH—C(=NH)—NH—;
R$_7$ is selected from the group consisting of phenyl, and alkyl having from one to eight carbons, said alkyl group being optionally substituted with one or more halogen atoms, aryl, or heteroaryl groups;
R$_8$ is selected from the group consisting of =O, =N—NHC(=O)—NH$_2$, =N—OH, =N—OCH$_3$, =N—O—CH$_2$—C$_6$H$_5$, =NNH—C(=S)—NH$_2$ and =N—NH—J;
R$_9$ is selected from the group consisting of hydrogen, and alkyl having from one to six carbons, said alkyl group being optionally substituted with one or more halogen atoms, aryl or heteroaryl groups;
J is a protecting group;
n is an integer from 3 to 10; and
m is an integer from 2 to 5.

10. A composition for inhibiting multicatalytic protease comprising a pharmaceutically acceptable carrier and a compound of formula:

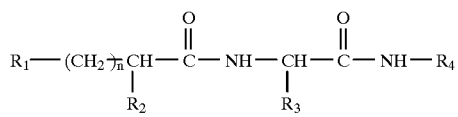

wherein:
R$_1$ is selected from the group consisting of —C≡N, —C(=O)OR$_9$, phthalimido, —NH—SO$_2$R$_9$, and —NH—J;
R$_2$ is selected from the group consisting of H, hydroxyl, alkyl having from one to ten carbons, and cycloalkyl having from three to seven carbons;
R$_3$ is selected from the group consisting of —(CH$_2$)$_m$—NH—C(=N—R$_5$)—NH$_2$, —R$_6$—NO$_2$, —R$_6$—J, and —R$_6$—CN;
R$_4$ is —CH(CH$_2$—R$_7$)—Q;
Q is selected from the group consisting of —CH—R$_8$, —C(=O)CH$_3$, —C(=O)CH$_2$Cl, —C(=O)CH$_2$Br, —C(=O)CH$_2$F, —C(=O)CHF$_2$, —C(=O)CF$_3$, —C(=O)C(=O)R$_7$,

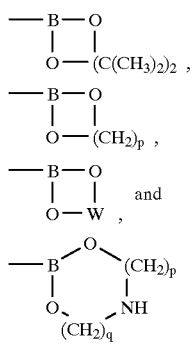

—C(=O)C(=O)NH—R$_7$, —C(=O)CO$_2$—R$_7$,
—C(=O)CO$_2$H, —B(OH)$_2$, where p and q, independently, are 2 or 3;

W is cycloalkyl;

R$_5$ is selected from the group consisting of —NO$_2$, —CN, and —J;

R$_6$ is —(CH$_2$)$_m$—NH—C(=NH)—NH—;

R$_7$ is selected from the group consisting of phenyl, and alkyl having from one to eight carbons, said alkyl group being optionally substituted with one or more halogen atoms, aryl, or heteroaryl groups;

R$_8$ is selected from the group consisting of =O, =N—NHC(=O)—NH$_2$, =N—OH, =N—OCH$_3$, =N—O—CH$_2$—C$_6$H$_5$, =NNH—C(=S)—NH$_2$ and =N—NH—J;

R$_9$ is selected from the group consisting of hydrogen, and alkyl having from one to six carbons, said alkyl group being optionally substituted with one or more halogen atoms, aryl or heteroaryl groups;

J is a protecting group;

n is an integer from 3 to 10; and m is an integer from 2 to 5.

11. A method for inhibiting multicatalytic protease comprising contacting a multicatalytic protease with an inhibitory amount of a compound of formula:

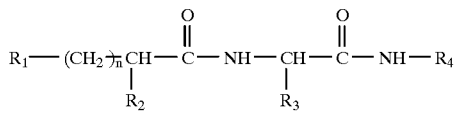

wherein:

R$_1$ is selected from the group consisting of —C≡N, —C(=O)OR$_9$, phthalimido, —NH—SO$_2$R$_9$, and —NH—J;

R$_2$ is selected from the group consisting of H, hydroxyl, alkyl having from one to ten carbons, and cycloalkyl having from three to seven carbons;

R$_3$ is selected from the group consisting of —(CH$_2$)$_m$—NH—C(=N—R$_5$)—NH$_2$, —R$_6$—NO$_2$, —R$_6$—J, and —R$_6$—CN;

R$_4$ is —CH(CH$_2$—R$_7$)—Q;

Q is selected from the group consisting of —CH—R$_8$, —C(=O)CH$_3$, —C(=O)CH$_2$Cl, —C(=O)CH$_2$Br, —C(=O)CH$_2$F, —C(=O)CHF$_2$, —C(=O)CF$_3$, —C(=O)C(=O)R$_7$,

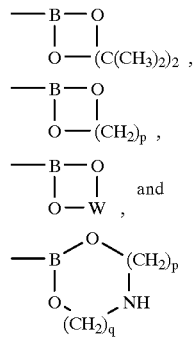

—C(=O)C(=O)NH—R$_7$, —C(=O)CO$_2$—R$_7$,
—C(=O)CO$_2$H, —B(OH)$_2$, where p and q, independently, are 2 or 3;

W is cycloalkyl;

R$_5$ is selected from the group consisting of —NO$_2$, —CN, and —J;

R$_6$ is —(CH$_2$)$_m$—NH—C(=NH)—NH—;

R$_7$ is selected from the group consisting of phenyl, and alkyl having from one to eight carbons, said alkyl group being optionally substituted with one or more halogen atoms, aryl, or heteroaryl groups;

R$_8$ is selected from the group consisting of =O, =N—NHC(=O)—NH$_2$, =N—OH, =N—OCH$_3$, =N—O—CH$_2$—C$_6$H$_5$, =NNH—C(=S)—NH$_2$ and =N—NH—J;

R$_9$ is selected from the group consisting of hydrogen, and alkyl having from one to six carbons, said alkyl group being optionally substituted with one or more halogen atoms, aryl or heteroaryl groups;

J is a protecting group;

n is an integer from 3 to 10; and m is an integer from 2 to 5.

* * * * *

UNITED STATES PATENT AND TRADEMARK OFFICE
CERTIFICATE OF CORRECTION

PATENT NO. : 5,990,083
DATED : November 23, 1999
INVENTOR(S) : Iqbal et al.

It is certified that error appears in the above-identified patent and that said Letters Patent is hereby corrected as shown below:

Title page,
Under "OTHER PUBLICATIONS,"
First column,
At Baldwin, J., second line thereof, please delete "chymotripsin" and insert -- chymotrypsin -- therefor.

Page 2,
First column,
At Ciechanover and Schwartz, please delete "ubiquitin-mediasted" and insert -- ubiquitin-mediated -- therefor.
At Dreschsel, D., third line thereof, please delete "Analytical" and insert -- Analytical -- therefor.
At Driscoll and Goldberg, please delete "can" and insert -- can -- therefor.

Second column,
At Fruh, Klaus, second line thereof, please delete "comoplex-encoded" and insert -- complex-encoded -- therefor.
At Fruh, Klaus, third line thereof, please delete "Biiological" and insert -- Biological -- therefor.

Page 3,
First column,
At Haas, third line thereof, please delete "chemistry" and insert -- Chemistry -- therefor.
At Hoffman, L., third line thereof, please insert -- Biological Chem., 267(31) 22362-22368 (1992) -- after "The J. of".

Second column,
At Jaspers and Tischler, second line thereof, please delete "Hindlng" and insert -- Hin Limb -- therefor.
At Kidd and Woo, third line thereof, please insert -- pp. 421-440 -- after "Elsevier".
At Kojima and Omori, second line thereof, please delete precursos" and insert -- precursors -- therefor.
At Laskowski and Kato, please delete "proteinaseses" and insert -- proteinases -- therefor.
Lucas, J., second line, thereof, please delete "Endproteinase and insert -- Endoprotenase -- therefor.

UNITED STATES PATENT AND TRADEMARK OFFICE
CERTIFICATE OF CORRECTION

PATENT NO. : 5,990,083
DATED : November 23, 1999
INVENTOR(S) : Iqbal et al.

It is certified that error appears in the above-identified patent and that said Letters Patent is hereby corrected as shown below:

"OTHER PUBLICATIONS," contd.
Page 4,
First column,
At McDermott, J.R., please delete "High-M$^{4r}$" and insert -- High-M$^r$ -- therefor.
At Pappolla, M.A., second line thereof, please delete "ubiquitinilated" and insert
-- ubiquitinated -- therefor.

Page 5,
First column,
At Weitman and Etlinger, third line thereof, please add -- Chem, 267(10) 6977-6982
(1992). -- after "The J. of Biol."

Second column,
At Theobald, P., third line thereof, please add --, 2395-2402 -- after "J. Med. Chem,
1991, 34"
At Imperiali, B., second line thereof, please delete "Fluormethyl" and insert
-- Fluoromethyl -- therefor.

Column 1,
Line 22, please delete "hasting" and insert -- having -- therefor.
Line 44, please delete "chirmotrypsin-like" and insert -- chymotrypsin-like -- therefor.

Column 4,
Line 20, please delete "=CO" and insert -- =O --therefor.
Line 24, please delete "s elected" and insert -- selected -- therefor.
Lines 47-48, please delete "=NNH—C(=OS)—NH$_2$" and insert --
=NNH—C(=S)—NH$_2$ -- therefor.

Column 5,
Line 8, please delete "thae" and insert -- the -- therefor.
Lines 48-54, please delete 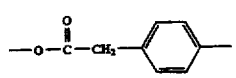 "

and insert 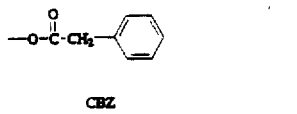 therefor.

UNITED STATES PATENT AND TRADEMARK OFFICE
CERTIFICATE OF CORRECTION

PATENT NO. : 5,990,083
DATED : November 23, 1999
INVENTOR(S) : Iqbal et al.

It is certified that error appears in the above-identified patent and that said Letters Patent is hereby corrected as shown below:

Column 7,
Line 12, please delete "leacine" and insert -- leucine -- therefor.
Line 42, please delete "boded" and insert -- body -- therefor.

Column 9,
Line 17, please delete "SDD-1" and insert -- SOD-1 -- therefor.

Column 10,
Line 66, please delete "rates" and insert -- rats -- therefor.
Line 66, please delete "Jetspers" and insert --Jaspers -- therefor.

Column 12,
Line 31, please delete "*Meatbolism*" and insert -- *Metabolism* -- therefor.

Column 13, Table 3,
Line 39, please delete "<0.95" and insert -- <0.05 -- therefor.

Column 14,
Line 39, please delete "2x105" and insert -- $2 \times 10^5$ -- therefor.
Line 44, please delete "*J. Imunol.*" and insert -- *J. Immunol.* -- thereof.

Column 15,
Line 17, please delete "E.H78" and insert -- EH78 -- therefor.
Line 55, please delete "matant" and insert -- mutant -- therefor.
Line 56, please delete "describes" and insert -- described -- therefor.
Line 66, please delete "CDNA" and insert -- cDNA -- therefor.

Column 16,
Line 44, please delete "geol" and insert -- gel -- therefor.
Line 44, please delete "1x0 TBS" and insert -- 1xTBS -- therefor.

Column 18,
Line 15, please delete "thee" and insert -- the -- therefor.

Column 19,
Line 9, please delete "monofluoromethyl ketonet" and insert -- monofluoromethylketone -- therefor.
Line 12, please delete "Falmer" and insert -- Palmer -- therefor.
Line 27, please delete "alp;ha-keto" and insert -- alpha-keto -- therefor.
Line 31, please delete "alpha-kimto" and insert -- alpha-keto -- therefor.

UNITED STATES PATENT AND TRADEMARK OFFICE
CERTIFICATE OF CORRECTION

PATENT NO. : 5,990,083
DATED : November 23, 1999
INVENTOR(S) : Iqbal et al.

It is certified that error appears in the above-identified patent and that said Letters Patent is hereby corrected as shown below:

Column 19,
Lines 55-56, please delete

" $R_1$-$CH_2$)—$CHR_2$—CONH—CH($R_3$)—CONH—CH ($CH_2R_7$)— "

and insert

-- $R_1$-$(CH_2)_a$-$CHR_2$-CONH-CH($R_3$)-CONH-CH9$CH_2R_7$)-CH(OH)-CONH$R_7$ ---> -- therefor.

Column 20,
Line 33, please delete "1 nmol" and insert -- 4 mmol -- thereof.

Column 21,
Line 3, please delete "Celitee" and insert -- Celite® -- therefor.

Column 23,
Line 61, please delete "70-750" and insert -- 70-75° -- therefor.
Line 63, please delete "as washed" and insert -- was washed -- therefor.

Column 24,
Line 27, please delete " 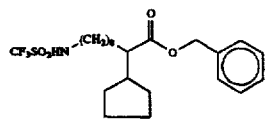 "

Column 24,
Lines 31-37, please delete "  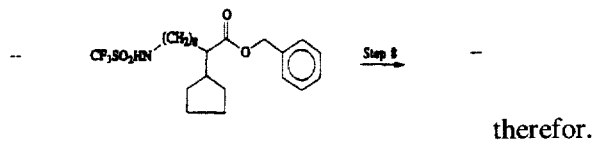  "

and insert

-- 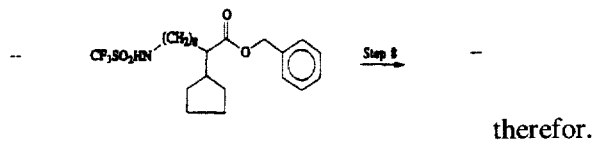 -- therefor.

UNITED STATES PATENT AND TRADEMARK OFFICE
CERTIFICATE OF CORRECTION

PATENT NO.    : 5,990,083
DATED         : November 23, 1999
INVENTOR(S)   : Iqbal et al.

It is certified that error appears in the above-identified patent and that said Letters Patent is hereby corrected as shown below:

Column 26,
Line 16, please delete "CDC13" and insert -- CDC13 -- therefor.

Column 27-28, Table 5,
At line beginning with "Example No.", please delete "a", in third column, and insert -- n -- therefor.

Column 27-28, Table 5,
Please delete

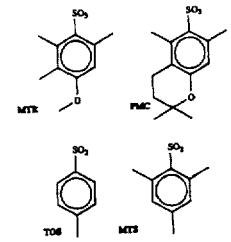

and insert

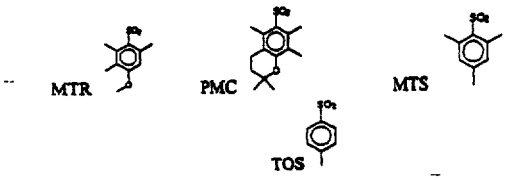

Column 29-30, Table 5,
Please delete

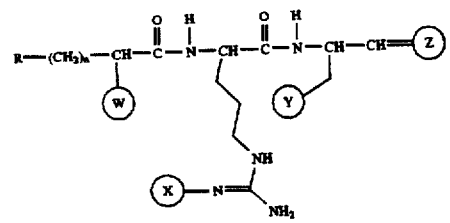

UNITED STATES PATENT AND TRADEMARK OFFICE
CERTIFICATE OF CORRECTION

PATENT NO. : 5,990,083
DATED : November 23, 1999
INVENTOR(S) : Iqbal et al.

It is certified that error appears in the above-identified patent and that said Letters Patent is hereby corrected as shown below:

Columns 29-30, Table 5,
At line beginning with "Example No.", last column, please delete "$IC_{50}nm$" and insert -- $IC_{50}nM$ -- therefor.

Column 33,
Line 44, please delete "-N g-nitro-L-" and insert -- $-N^g$-nitro-L- -- therefor.

Column 41,
Line 11, please delete "-nonainoyl-" and insert -- nonanoyl- -- therefor.
Line 51, please delete "azetal" and insert -- acetal -- therefor.

Column 44,
Line 32, please delete "(10( mmol)" and insert -- (10 mmol) -- therefor.

Column 49,
Line 29, please delete "Rf" and insert -- $R_f$ -- therefor.

Signed and Sealed this

Fourth Day of December, 2001

*Attest:*

NICHOLAS P. GODICI
*Attesting Officer*  Acting Director of the United States Patent and Trademark Office